US011344662B2

(12) United States Patent
Spearman et al.

(10) Patent No.: US 11,344,662 B2
(45) Date of Patent: May 31, 2022

(54) SYSTEMS AND METHODS FOR TREATING BLOOD

(71) Applicant: Humanity Life Extension LLC, Saint Paul, MN (US)

(72) Inventors: Patrick Richard Spearman, The Woodlands, TX (US); Alexander Patrick Spearman, The Woodlands, TX (US)

(73) Assignee: HUMANITY LIFE EXTENSION LLC, Saint Paul, MN (US)

( * ) Notice: Subject to any disclaimer, the term of this patent is extended or adjusted under 35 U.S.C. 154(b) by 260 days.

(21) Appl. No.: 14/623,455

(22) Filed: Feb. 16, 2015

(65) Prior Publication Data

US 2015/0231323 A1 Aug. 20, 2015

Related U.S. Application Data

(60) Provisional application No. 62/011,451, filed on Jun. 12, 2014, provisional application No. 61/983,752, (Continued)

(51) Int. Cl.
*A61M 1/16* (2006.01)
*A61M 1/36* (2006.01)
(Continued)

(52) U.S. Cl.
CPC ............. *A61M 1/369* (2013.01); *A61M 1/14* (2013.01); *A61M 1/16* (2013.01); *A61M 1/1698* (2013.01);
(Continued)

(58) Field of Classification Search
CPC ........ A61M 1/14; A61M 1/16; A61M 1/1698; A61M 1/3621; A61M 1/3687;
(Continued)

(56) References Cited

U.S. PATENT DOCUMENTS 3,107,642 A 10/1963 Lakin
3,768,977 A 10/1973 Brumfield
(Continued)

FOREIGN PATENT DOCUMENTS

DE 44 06 106 A1 8/1995
WO WO 2018/144970 A1 8/2018

OTHER PUBLICATIONS

PCT—*Notification of Transmittal of the International Search Report and the Written Opinion of the Int'l Searching Authority, or the Declaration*, for Int'l Appl. No. PCT/US15/16064, Int'l filing dated Feb. 16, 2015.
(Continued)

*Primary Examiner* — Kai H Weng
(74) *Attorney, Agent, or Firm* — Bakek Botts, LLP

(57) ABSTRACT

According to some embodiments, a system may treat blood outside the body of a patient. The system may include one or more pumps configured to draw blood from a patient into a fluid flow path at a rate, for example, of 5-7 liters per minute. The system may include one or more heat exchangers coupled to the fluid flow path and configured to heat the blood, for example, to a temperature above 42 degrees Celsius and below 43.2 degrees Celsius.

17 Claims, 15 Drawing Sheets

Related U.S. Application Data filed on Apr. 24, 2014, provisional application No. 61/940,628, filed on Feb. 17, 2014.

(51) Int. Cl.
| | |
|---|---|
| *A61M 1/32* | (2006.01) |
| *A61M 1/34* | (2006.01) |
| *A61M 1/14* | (2006.01) |
| *A61M 5/44* | (2006.01) |
| *A61F 7/00* | (2006.01) |

(52) U.S. Cl.
CPC ............. *A61M 1/32* (2013.01); *A61M 1/341* (2014.02); *A61M 1/36* (2013.01); *A61M 1/3607* (2014.02); *A61M 1/3621* (2013.01); *A61M 5/44* (2013.01); *A61F 2007/0054* (2013.01); *A61F 2007/0089* (2013.01); *A61M 2202/00* (2013.01); *A61M 2202/0208* (2013.01); *A61M 2202/0216* (2013.01); *A61M 2205/3331* (2013.01); *A61M 2205/3334* (2013.01); *A61M 2205/3368* (2013.01); *A61M 2205/366* (2013.01); *A61M 2210/12* (2013.01)

(58) Field of Classification Search
CPC ............. A61M 1/369; A61M 2202/00; A61M 2202/0208; A61M 2202/0216; A61M 2205/366; A61M 2210/12; A61M 5/44
See application file for complete search history.

(56) References Cited

U.S. PATENT DOCUMENTS

| | | | | |
|---|---|---|---|---|
| 5,217,689 | A | * | 6/1993 | Raible .................... B01D 63/02 422/46 |
| 5,476,444 | A | | 12/1995 | Keeling et al. |
| 5,647,984 | A | * | 7/1997 | Hovland ............. A61M 1/1686 210/175 |
| 5,725,776 | A | | 3/1998 | Kenley |
| 5,730,720 | A | | 3/1998 | Sites et al. |
| 6,117,390 | A | * | 9/2000 | Corey, Jr. ........... A61M 1/1629 422/45 |
| 6,156,007 | A | | 12/2000 | Ash |
| 6,579,496 | B1 | | 6/2003 | Fausset et al. |
| 6,827,898 | B1 | | 12/2004 | Fausset et al. |
| 7,819,835 | B2 | | 10/2010 | Landy et al. |
| 7,998,101 | B2 | | 8/2011 | Ash |
| 8,496,874 | B2 | | 7/2013 | Gellman et al. |
| 9,555,184 | B2 | | 1/2017 | Spearman |
| 10,773,012 | B2 | | 9/2020 | Spearman |
| 10,946,134 | B2 | | 3/2021 | Spearman |
| 11,033,673 | B2 | | 6/2021 | Spearman |
| 2001/0039441 | A1 | | 11/2001 | Ash |
| 2003/0163183 | A1 | * | 8/2003 | Carson .................. A61F 7/0085 607/108 |
| 2004/0102732 | A1 | | 5/2004 | Naghavi et al. |
| 2008/0199357 | A1 | * | 8/2008 | Gellman ............. A61M 1/1698 422/48 |
| 2010/0198132 | A1 | | 8/2010 | Pesenti |
| 2010/0326916 | A1 | * | 12/2010 | Wrazel .................... A61M 1/16 210/646 |
| 2012/0189711 | A1 | * | 7/2012 | Greenberg .......... A61M 1/3672 424/618 |
| 2012/0296253 | A1 | | 11/2012 | Mathews et al. |
| 2015/0231322 | A1 | | 8/2015 | Spearman |
| 2015/0231324 | A1 | | 8/2015 | Spearman |
| 2017/0246375 | A1 | | 8/2017 | Spearman |
| 2019/0175813 | A1 | | 6/2019 | Spearman |
| 2020/0179586 | A1 | | 6/2020 | Spearman et al. |
| 2021/0069402 | A1 | | 3/2021 | Spearman |

OTHER PUBLICATIONS

PCT Recordation of Search History, Ref. Appl. PCT/US15/16064; CL1N Number/Technical Field of PCT Application: 0002 Life Sciences, dated Jun. 14, 2015.

Rehydration Project, "Unit 5—Treatment of Dehydrated Patients Medical Education: Teaching Medical Students about Diarrhoeal Diseases", Meded, Aug. 2, 2013; pp. 4-5; downloaded from Internet via internet archive—waybackmachine: https://web.archive.org/web/20140129091451http://www.rehydrate.org/diarrhoea/tmsdd/5med.htm.

Forster et al., "Low-flow $CO_2$ removal integrated into a renal-replacement circuit can reduce acidosis and decrease vasopressor requirements", Critical Care 2013, 17:R154, p. 1, results [downloaded from Internet: http://www.ncbi.nim.nih.gov/pmc/articles/PMC4056563/pdf/cc12833.pdf on Jun. 20, 2015], 2013

European Patent Office Communication, pursuant to Rule 62 EPC, the supplementary European search report (Art. 153(7) EPC) and the European search opinion, Application No. 15749068.1-1651/3107642 PCT/US2015016064; Ref. P12027WE, dated Sep. 29, 2017.

Joseph B. Zwischenberger, et al. "Percutaneous Venovenous Perfusion-Induced Systemic Hyperthermia for Lung Cancer: A Phase I Safety Study", *Ann Thorac Surg 2004*; 77:1916-1925, 2004.

European Patent office, Commmunication pursuant to Article 94(3) EPC, Application No. 15 749 068.1-1115, dated Jul. 8, 2018.

Communication from European Patent Office re Application No. 18748028.0-1113/3648814; PCT/US2018016797, dated Mar. 9, 2021.

P. R. Spearman, U.S. Appl. No. 15/425,494 Non-final Office Action, dated May 1, 2020.

P. R. Spearman, U.S. Appl. No. 15/425,494 Response to Non-final Office Action, dated Aug. 3, 2020.

P. R. Spearman, U.S. Appl. No. 15/425,494 Final Office Action, dated Aug. 20, 2020.

P. R. Spearman, U.S. Appl. No. 15/425,494 Response to Final Office Action, dated Oct. 22, 2020.

P. R. Spearman, U.S. Appl. No. 16/214,728 Non-final Office Action, dated Nov. 13, 2020.

P. R. Spearman, U.S. Appl. No. 16/214,807 Non-final Office Action, dated Aug. 20, 2020.

P. R. Spearman, U.S. Appl. No. 16/214,807 Response to Non-final Office Action, dated Nov. 18, 2020.

EP Search Report, Communication re Application #19209281.5-1115, dated Mar. 11, 2020.

EP Search Report, Communication re Application #19214811.2-1115, dated Apr. 20, 2020.

EP Search Report, Communication re Application #19214823.7-1115, dated Apr. 23, 2020.

Communication from Intellectual Property India re Application No. 201627028750, dated Oct. 26, 2020.

Spearman, U.S. Appl. No. 14/623,447, Non-final Office Action, dated Apr. 4, 2018.

Spearman, U.S. Appl. No. 14/623,477, Response to Non-final Office Action, dated Aug. 3, 2018.

Spearman, U.S. Appl. No. 14/623,477, Non-final Office Action, dated Mar. 4, 2019.

Patent Cooperation Treaty, PCT, International Search Report and Written Opinion of the International Searching Authority (PCT Rule 43 bis. 1), (PCT Article 18 and Rules 43 and 44), Intl. Appln. No. PCT/US 18/16797, dated Apr. 12, 2018.

U.S. Appl. No. 16/214,728, filed Dec. 10, 2018, P. R. Spearman.
U.S. Appl. No. 16/214,807, filed Dec. 10, 2018, P. R. Spearman.
U.S. Appl. No. 16/214,840, filed Dec. 10, 2018, P. R. Spearman.

* cited by examiner

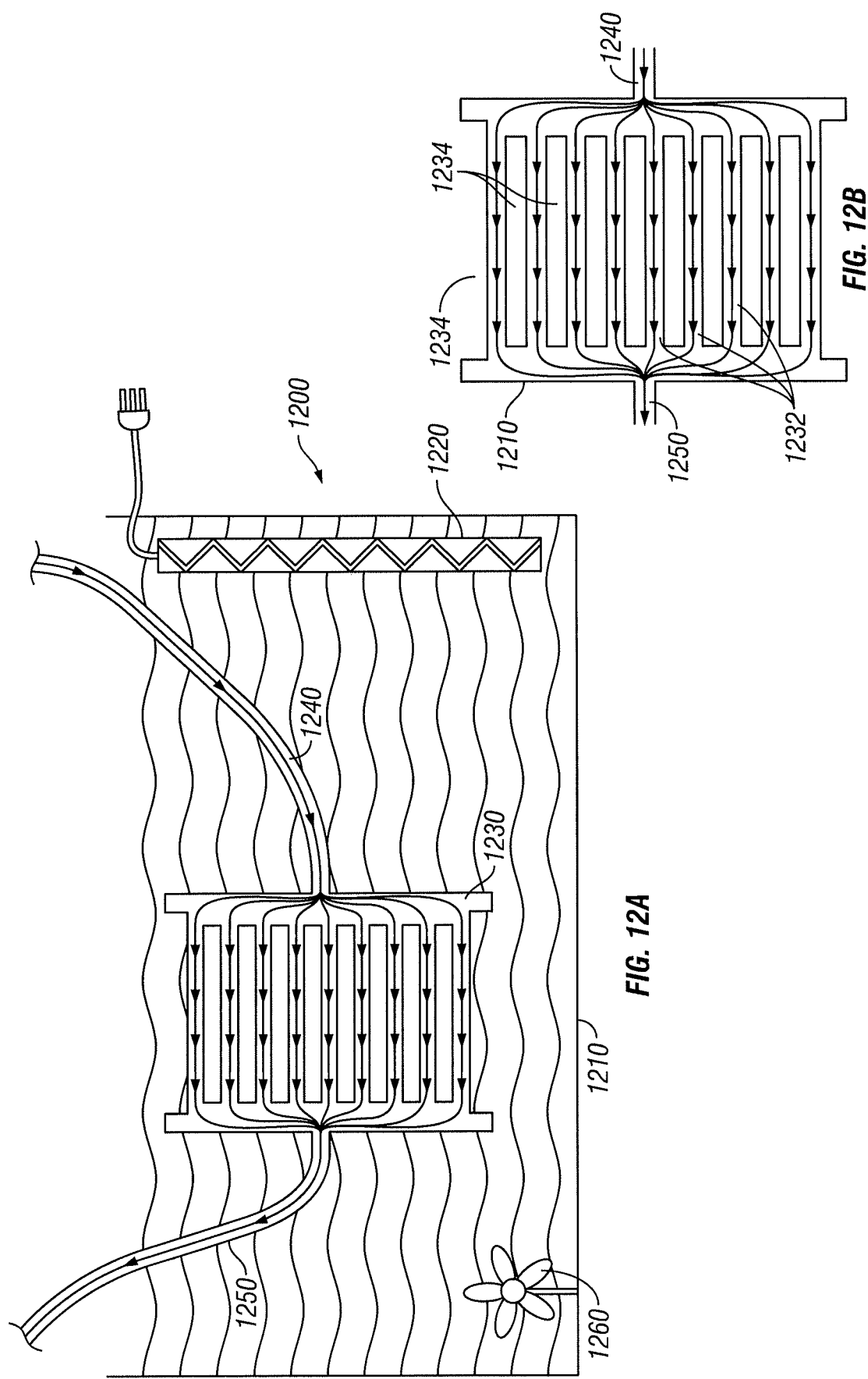

SYSTEMS AND METHODS FOR TREATING BLOOD

RELATED APPLICATIONS

This application claims priority to U.S. Provisional Application Ser. No. 61/940,628, entitled "A System For Induced Hyperthermia," filed Feb. 17, 2014; U.S. Provisional Application Ser. No. 61/983,752 entitled "A System For Induced Hyperthermia," filed Apr. 24, 2014; and U.S. Provisional Application Ser. No. 62/011,451, entitled "A System For Induced Hyperthermia," filed Jun. 12, 2014.

TECHNICAL FIELD

This disclosure relates to systems and methods for treating blood.

BACKGROUND

Hyperthermia has been used to treat certain maladies, including killing cancer cells. Certain methods and procedures have had limited and poor results in extending patient life and/or their quality of living. For example, certain therapies only target a certain area of the body. As another example, blood removed from the body is heated to higher than a desired temperature and then returned back to the body (in some cases cooled to a lower temperature than desired).

Suggested forms of induced hyperthermia suffer from the need of major advancements and significant changes in order to have meaningful results and thus cannot be used as a standard of care for treating cancers by various medical and scientific communities.

SUMMARY

According to some embodiments, a system may be used to induce hyperthermia in a patient. The system may include one or more pumps configured to draw blood, for example from a patient, into a path at a rate, for example, above 4 liters per minute. The system may include one or more heat exchangers coupled to the path and configured to heat the blood to a temperature, for example, above 42 degrees Celsius and below 43.2 degrees Celsius. Or, in other embodiments the temperature may be above 42 degrees and below 43.8 degrees or below, for example, 43.5 degrees Celsius.

According to some embodiments, a system may be used to treat blood outside of a body of a patient. The system may include a path located outside of a body of a patient. The system may further include one or more pumps configured to circulate the blood in the path at a rate, for example, above 4 liters per minute. The system may further include one or more heat exchangers coupled to the path and configured to heat the blood to a temperature, for example, above 42 degrees Celsius and below 43.2 degrees Celsius. Or, in other embodiments the temperature may be above 42 degrees Celsius and below 43.8 degrees Celsius or below, for example, 43.5 degrees Celsius. The system may further include one or more modules configured to administer a substance (e.g., ozone or Freon) to the blood that facilitates the production of reactive oxygen species within the blood. The substance may include any element or composition of matter that constitutes a free radical or that is an unstable substance (e.g. ozone) that reacts with some substance in the body (e.g. oxygen) to form a free radical. The system may further include one or more dialysis modules configured to perform dialysis (e.g., convection dialysis or diffusion dialysis) on the blood. The system may further include a venting system to remove carbon dioxide from the blood. The venting system can add oxygen to the blood, in some embodiments. The system may also include an oxygenator to add oxygen to the blood.

According to some embodiments, a method may induce hyperthermia in a patient. The method may include drawing blood from a patient into a path at a rate, for example, above 4 liters per minute. The method may further include heating the blood to a temperature, for example, above 42 degrees Celsius and below 43.2 degrees Celsius. Or, in other embodiments the temperature may be above 42 degrees Celsius and below 43.8 degrees Celsius or below, for example, 43.5 degrees Celsius. The method may further include adding the heated blood back into the patient.

According to some embodiments, a method may treat blood outside of a body of a patient. The method may include circulating blood through a path at a rate, for example above 4 liters per minute. The method may further include heating the blood to a temperature above 42 degrees Celsius and below 42.9 degrees Celsius to provide treated blood. Or, in other embodiments the temperature may be above 42 degrees Celsius and below 43.8 degrees Celsius or below, for example, 43.5 degrees Celsius. The method may further include performing dialysis (e.g., convection dialysis or diffusion dialysis) on the blood. The method may further include removing carbon dioxide from the blood. The method may also include adding oxygen to the blood.

According to some embodiments, a method may treat blood outside of a body of a patient. The method may further include heating the blood to a temperature above 42 degrees Celsius and below 43.2 degrees Celsius. Or, in other embodiments the temperature may be above 42 degrees Celsius and below 43.8 degrees Celsius or below, for example, 43.5 degrees Celsius. The method may also include adding a substance to the blood that facilitates the production of reactive oxygen species within the blood as discussed above.

In various embodiments, some, none, or all of the following advantages can be present. Induced hyperthermia can be applied to the entire body. Blood can be maintained at a temperature between 42 and 43.2 degrees Celsius (or at any of the temperature ranges or temperatures discussed herein) while being removed and pumped into the body. Or, in other embodiments the temperature may be above 42 degrees Celsius and below 43.8 degrees Celsius or below, for example, 43.5 degrees Celsius. Induced hyperthermia can be accomplished in some cases without the need of a heat chamber. One or more of the embodiments described above may be used as a standard of care and treatment for various cancers or other maladies and can reduce or avoid the need of further treatment (e.g., surgical removal of tumor or cancer cells). One or more of the techniques discussed above may enable induced hyperthermia such that: a temperature of 42 degrees Celsius or slightly higher (e.g., such as any of the temperature ranges or temperatures discussed herein) is applied to all, or substantially all, or a majority of the cancer cells in a body for an appropriate duration of time (such as any of the ranges of time discussed herein); the entire body (or the important parts of the body) can be heated substantially consistently throughout the treatment; the core body (or the important parts of the body) temperature, including the brain's temperature, can be accurately monitored. A precise, body-wide, controllable hyperthermia method can be achieved that can kill all, nearly all, or a substantial number of the cancer cells in a patient over their entire body or substantially their entire body without harming (or severely harming) or damaging the patient either during the procedure, hours after the procedure, or one or more days after the procedure. A high blood flow rate may be enabled so that induced hyperthermia can raise the core body temperature to the range of 42 to 43.2 degrees Celsius (or any of the temperature ranges or temperatures discussed herein) within 45 minutes (or any of the time ranges discussed herein) without raising the temperature of the blood to 44 to 48 degrees Celsius, which has a greater potential to kill the patient's good cells. Or, in other embodiments the temperature may be above 42 degrees Celsius and below 43.8 degrees Celsius or below, for example, 43.5 degrees Celsius. Convection dialysis can be employed to remove toxins and/or pro inflammatory mediators created by full body induced hyperthermia that are in the range of 1-50,000 Daltons or above; dialysis (convection or diffusion) can be performed during the induced hyperthermia and after the induced hyperthermia (e.g., up to 48 hours after induced hyperthermia, or any of the time durations discussed above) to better remove toxins and/or pro inflammatory mediators. Pro inflammatory mediators, toxins, and/or plasma water can be removed using dialysis; these can be placed in a suitable location (e.g., a waste container). The amount of plasma water removed using dialysis can be measured and this measurement can be used to determine an amount of fluid to introduce to the blood. The fluid can be plasma water is electrolyte-balanced and/or acid-balanced. The fluid can be returned to the blood just prior to entering back into the patient's body. The fluid can help maintain physiological homeostasis and proper fluid balance.

Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

Reference is now made to the following description taken in conjunction with the accompanying drawings, wherein like reference numbers represent like parts.

FIGS. 12A-12C illustrate embodiments of heat exchanging systems.

DETAILED DESCRIPTION

Figure 1:
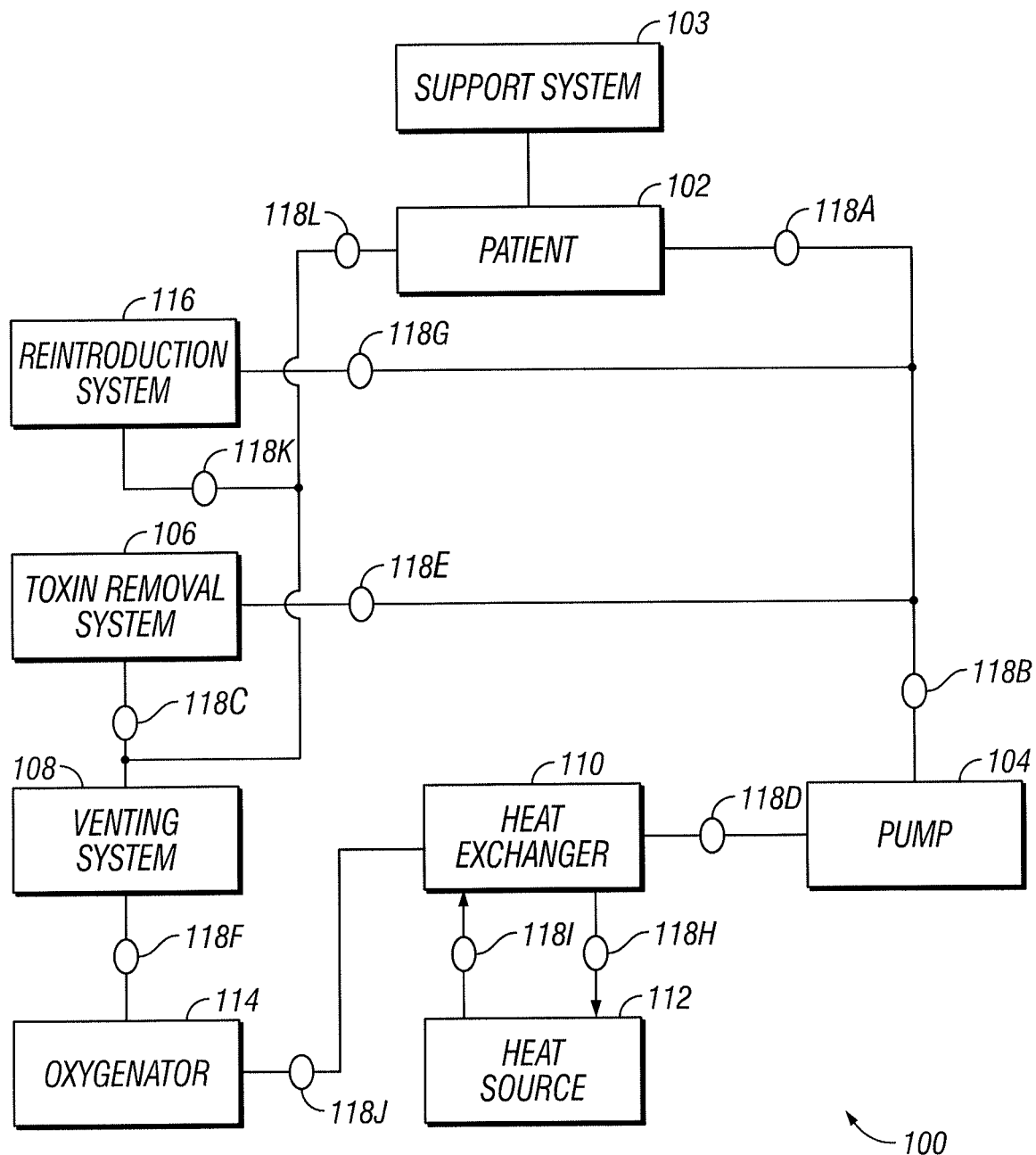
FIG. 1 illustrates one embodiment of a system for inducing hyperthermia.

FIG. 1 illustrates an embodiment of system 100 that may be used to induce hyperthermia in patient 102. The system 100 may be used to treat blood outside of the body of the patient 102. The block diagram of FIG. 1 illustrates a blood path where blood from patient 102 may be drawn by pump 104. On the other side of pump 104 blood may be pushed to other components of FIG. 1 (e.g., downstream from pump 104). The blood may be directed to heat exchanger 110 that may heat the blood using heat source 112. After being heated, the blood may be sent to oxygenator 114 which can be configured to add oxygen to the blood (and/or remove carbon dioxide from the blood). In some embodiments, oxygenator 114 can be placed in the path such that blood reaches it prior to reaching heat exchanger 110. The blood may be directed to venting system 108 (which can vent carbon dioxide from the blood). After, the blood may be sent to patient 102. Separate streams may be sent to toxin removal system 106 and reintroduction system 116. Reintroduction system 116 can add pharmaceuticals, vitamins, and/or nutritional elements (e.g., liquid food and/or glucose) to the blood before sending the blood to the path in which pump 104 draws blood from patient 102 (e.g., upstream from pump 104). After being treated by toxin removal system 106, the blood can be sent to the path in which pump 104 draws blood from patient 102 (e.g., upstream from pump 104). Furthermore, temperature probes 118a-l may be included in system 100 to monitor the temperature of the blood throughout the path. Other temperature probes (not explicitly shown) may be used to measure the temperature of the patient in various locations, and may include a measurement or estimate of core temperature. Also, system 100 may further include support system 103, which can be used to provide chemicals or other support to patient 102 to facilitate the health of patient 102.

In some embodiments, system 100 can be used to induce hyperthermia in patient 102 between 42 and 43.9 degrees Celsius, and more preferably between 42 and 43.2 degrees. Or, in other embodiments the temperature may be above 42 degrees Celsius and below 43.8 degrees Celsius or below, for example, 43.5 degrees Celsius. In some embodiments, the induced hyperthermia can be maintained for a duration in a range of, for example, 15 minutes to 6 hours. In some embodiments, to induce hyperthermia and/or maintain the induced hyperthermia, blood of the patient may be withdrawn from the patient and/or returned to the patient at a rate of, for example 5-7 liters per minute. Furthermore, the techniques described herein regarding induced hyperthermia can be used to treat various maladies, in some embodiments. As examples, various types of cancer, bacterial infections, viral infections, meningitis, Hepatitis C, Ebola, AIDS, staph infections, and pneumonia (viral or bacterial) may be treated using the induced hyperthermia techniques discussed herein.

In particular, according to some embodiments, system 100 can be used to induce hyperthermia in patient 102 between 42 and 43.9 degrees Celsius, and more preferably between 42 and 43.2 degrees Celsius, in order to treat various types of cancers. Or, in other embodiments the temperature may be above 42 degrees Celsius and below 43.8 degrees Celsius or below, for example, 43.5 degrees Celsius. Various types of cancer cells die at temperatures of approximately 42 degrees Celsius and above if they are subjected to that temperature or slightly above for a proper length of time. Furthermore, because there is a differential thermal response between normal cells and cancerous tissue as well as certain viruses and bacteria, induced systemic hyperthermia at 42 degrees Celsius and higher (within a range of tolerance) can cause death of cancer cells, viruses, and/or bacteria with a lesser impact on the body's healthy cells. At the molecular level, hyperthermia can be a stimulus for apoptotic cell death in cancer cells. At the cellular level, effects of hyperthermia can include: damage caused by heat-induced lipid peroxidation, reduction of the mitotic rate, destabilization of cellular membranes, and/or an increase in tumor necrosis factor-a and IL-1B. In some embodiments, within a tumor, hyperthermia can cause decreased blood flow, an elevated rate of glycolysis, acidosis, and/or oxygen utilization. Heat can have a stimulatory effect on the immune system, e.g., potentially causing increases in the production of interferon-y and/or increased immune surveillance.

In some embodiments, induced hyperthermia using system 100 may be accomplished by removing and heating the patient's blood and then returning the blood to the patient. The procedure may increase the core temperature of all, or substantially all, of the patient's body to a temperature in the range of 42 to 43.2 degrees Celsius, and sometimes up to 43.9 degrees Celsius. Or, in other embodiments the temperature may be above 42 degrees Celsius and below 43.8 degrees Celsius or below, for example, 43.5 degrees Celsius. Furthermore, the procedure may increase the core temperature of all, or substantially all, of the patient's body to a temperature in any other suitable range for treating particular maladies, such as, for example, a range of 42 to 43.9 degrees Celsius, a range of 42.1 to 43.9 degrees Celsius, a range of 42.2 to 43.9 degrees Celsius, a range of 42.3 to 43.9 degrees Celsius, a range of 42.4 to 43.9 degrees Celsius, a range of 42.5 to 43.9 degrees Celsius, a range of 42.6 to 43.9 degrees Celsius, a range of 42.7 to 43.9 degrees Celsius, a range of 42.8 to 43.9 degrees Celsius, a range of 42.9 to 43.9 degrees Celsius, a range of 43.0 to 43.9 degrees Celsius, a range of 43.1 to 43.9 degrees Celsius, a range of 43.2 to 43.9 degrees Celsius, a range of 43.3 to 43.9 degrees Celsius, a range of 43.4 to 43.9 degrees Celsius, a range of 43.5 to 43.9 degrees Celsius, a range of 43.6 to 43.9 degrees Celsius, a range of 43.7 to 43.9 degrees Celsius, a range of 43.8 to 43.9 degrees Celsius, a range of 42 to 43.8 degrees Celsius a range of 42 to 43.7 degrees Celsius, a range of 42 to 43.6 degrees Celsius, a range of 42 to 43.5 degrees Celsius, a range of 43 to 43.8 degrees Celsius, a range of 43.1 to 43.8 degrees Celsius, a range of 43.2 to 43.8 degrees Celsius, a range of 43.3 to 43.8 degrees Celsius, a range of 43.4 to 43.8 degrees Celsius, a range of 43.5 to 43.8 degrees Celsius, a range of 43.6 to 43.8 degrees Celsius, a range of 42 to 43.5 degrees Celsius, a range of 42.1 to 43.5 degrees Celsius, a range of 42.2 to 43.5 degrees Celsius, a range of 42.3 to 43.5 degrees Celsius, a range of 42.4 to 43.5 degrees Celsius, a range of 42.5 to 43.5 degrees Celsius, a range of 42.6 to 43.5 degrees Celsius, a range of 42.7 to 43.5 degrees Celsius, a range of 42.8 to 43.5 degrees Celsius, a range of 42.8 to 43.5 degrees Celsius, a range of 42.9 to 43.5 degrees Celsius, a range of 43.0 to 43.5 degrees Celsius, a range of 42 to 43.4 degrees Celsius, a range of 42 to 43.3 degrees Celsius, a range of 42 to 43.2 degrees Celsius, a range of 42 to 43.1 degrees Celsius, a range of 42 to 43.0 degrees Celsius, a range of 42 to 42.8 degrees Celsius, a range of 42 to 42.7 degrees Celsius, a range of 42 to 42.6 degrees Celsius, a range of 42 to 42.5 degrees Celsius, a range of 42 to 42.4 degrees Celsius, a range of 42 to 42.3 degrees Celsius, a range of 42 to 42.2 degrees Celsius, a range of 42 to 42.1 degrees Celsius, a range of 42.1 to 42.8 degrees Celsius, a range of 42.3 to 42.7 degrees Celsius, a range of 42.4 to 42.6 degrees Celsius, a range of 42.5 to 42.9 degrees Celsius, a range of 42.6 to 42.9 degrees Celsius, a range of 42.7 to 42.9 degrees Celsius, a range of 42.8 to 42.9 degrees Celsius, a range of 42.5 to 42.8 degrees Celsius, a range of 42.5 to 42.7 degrees Celsius, a range of 42.5 to 42.6 degrees Celsius, or any other range between 42 and 43.9 degrees Celsius. Additionally, the procedure may increase the core temperature or the temperature of all, or substantially all, of the patient's body to a temperature not above a particular temperature that may materially hurt the patient, such as, for example, a temperature not above 43.9 degrees Celsius, a temperature not above 43.8 degrees Celsius, a temperature not above 43.7 degrees Celsius, a temperature not above 43.6 degrees Celsius, a temperature not above 43.5 degrees Celsius, a temperature not above 43.4 degrees Celsius, a temperature not above 43.3 degrees Celsius, a temperature not above 43.2 degrees Celsius, a temperature not above 43.1 degrees Celsius, a temperature not above 43.0 degrees Celsius, a temperature not above 42.9 degrees Celsius, a temperature not above 42.8 degrees Celsius, a temperature not above 42.7 degrees Celsius, a temperature not above 42.6 degrees Celsius, a temperature not above 42.5 degrees Celsius, a temperature not above 42.4 degrees Celsius, a temperature not above 42.3 degrees Celsius, a temperature not above 42.2 degrees Celsius, a temperature not above 42.1 degrees Celsius, or a temperature not above 42.0 degrees Celsius.

The core temperature or the temperature of all, or substantially all, of the patient's body may be determined in any manner known in the medical field. For example, the core temperature or the temperature of all, or substantially all, of the patient's body may be determined based on a measurement taken at a single area of the patient's body or based on measurements taken at multiple areas of the patient's body. Examples of determining the core temperature or the temperature of all, or substantially all, of the patient's body are discussed below in further detail.

The time frame to raise the core temperature of the patient's body using the system 100 to the above-discussed range (or the above-discussed temperature) can be in the range of 20 minutes to 1 hour. In some embodiments, the time frame to raise the core temperature of the patient's body to the above-discussed range (or the above-discussed temperature) can be any other range, such as, 15 minutes to 25 minutes, 15 minutes to 30 minutes, 15 minutes to 35 minutes, 15 minutes to 40 minutes, 15 minutes to 45 minutes, 15 minutes to 50 minutes, 15 minutes to 1 hour, 30 minutes to 1 hour, 45 minutes to 1 hour, 15 minutes to 1.5 hours, 30 minutes to 1.5 hours, 45 minutes to 1.5 hours, 15 minutes to 2 hours, 30 minutes to 2 hours, 1 hour to 2 hours, or any other range of time. Furthermore, once the above-discussed temperature range (or the above-discussed temperature) of the body is reached, the temperature of the patient's body can be maintained (or intermittently maintained) within one or more of the above-discussed ranges (or maintained at one or more of the above-discussed temperatures) for a duration in a range of 15 minutes to 6 hours (e.g., more preferably 2-4 hours, or for 1, 1.5, 2, 3, 3.5, 4, 4.5, 5, or 5.5 hours). In some embodiments, the temperature of the patient's body can be maintained within one or more of the above-discussed ranges (or maintained at one or more of the above-discussed temperatures) for a duration in any other range, such as 15 minutes to 2 hours, 15 minutes to 3 hours, 15 minutes to 4 hours, 15 minutes to 5 hours, 15 minutes to 7 hours, 1 hour to 2 hours, 1 hour to 3 hours, 1 hour to 4 hours, 1 hour to 5 hours, 1 hour to 6 hours, 2 hours to 3 hours, 2 hours to 4 hours, 2 hours to 5 hours, 2 hours to 6 hours, 3 hours to 4 hours, 3 hours to 5 hours, 3 hours to 6 hours, or any other range.

In some embodiments, the body's healthy cells can be maintained safely at a temperature in the range of 42 to 42.9 degrees Celsius for up to 4 hours. Or, in other embodiments the temperature may be above 42 degrees Celsius and below 43.8 degrees Celsius or below, for example, 43.5 degrees Celsius. This can avoid damage to the body's healthy cells, organs, and physiological functions. The induced hyperthermia discussed herein can be accomplished without heating the blood or the body's healthy cells to more than a desired maximum temperature. For example, the maximum temperature can be any temperature in the range of 42.0 to 43.9 degrees Celsius, such as, for example 42.0, 42.1, 42.2, 42.3, 42.4, 42.5, 42.6, 42.7, 42.8, 42.9, 43.0, 43.1, 43.2, 43.3, 43.4, 43.5, 43.6, 43.7, 43.8, 43.9 degrees Celsius. In some situations, temperatures above the desired maximum temperature can result in damage to the patient's blood or to healthy cells. Optionally, fluids (such as saline and/or acid-balanced and electrolyte-balanced fluids) can be administered to the patient that are heated to between 42 and 43.9 degrees Celsius (e.g., 42.5 degrees Celsius, or any of the temperature ranges or temperatures discussed above); this may facilitate heating the core temperature of the patient to between 42 and 43.9 degrees Celsius (or any of the temperature ranges or temperatures discussed above) at a faster rate than without administering such fluids in various embodiments. Such fluids can be administered in the path where the blood flows to components of system 100 and/or into a patient directly.

In some embodiments, maintaining the temperature of the patient's body for a particular duration of time may include maintaining the temperature of the patient's body at the above-discussed ranges (or temperatures) throughout the entire duration of time, or throughout a substantial portion of the duration of time. For example, the temperature of the patient's body may increase above (or decrease below) the above-discussed ranges (or temperatures) for short periods during the duration of time. However, the average temperature of the patient's body during the duration of time may be at the above-discussed ranges (or temperatures). Or, the temperature of the patient's body can be at the above-discussed ranges (or temperatures) for any of the above discussed amounts of time during a longer hyperthermia procedure. For example, the body could be maintained within a range of 42.5-43.2 degrees Celsius for one hour of a two hour hyperthermia procedure and that hour could be the total time of intermittent time periods (e.g. two half hour periods) where the temperature was in that range.

In various embodiments, system 100 may include other various materials and structures to facilitate the operations discussed herein. For example, catheters and/or cannulas, which may be placed on patient 102 to remove and/or return blood (e.g., a minimally invasive long venous catheter and a minimally invasive short arterial cannula). As another example, the system may further include tubing used to connect one or more components of the system 100 (e.g., the connector between heat exchanger 110 and oxygenator 114, etc.) may be high-grade PVC. As a further example, pump 104 can be centrifugal and resistant dependent with a flow range of 0.5 to 15 liters per minute (or any of the flow rates discussed below). Various connectors with luer locks can be incorporated in the path to allow for the addition of a toxin removal system path (e.g., a convection dialysis path) and for drawing any samples useful for laboratory analysis in various embodiments. Any suitable techniques or equipment can be used to implement the path depicted in FIG. 1. The path is generally a fluid flow path though other types of paths may be used in various embodiments. The path may be configured to allow fluids (e.g., liquids) to and from the various components of system 100. Valves, tubes, locks, or other suitable equipment may be used to implement the path of system 100.

In some embodiments, system 100 can be used in a veno-veno system. For example, system 100 may be used to cause blood from patient 102 to be extracted, heated, and then returned to patient 102 via the top right atrium of the heart using a cannula (or other device) in the jugular vein. This is where the heart pumps the heated blood to the body of patient 102. Causing the heart to distribute the heated blood can facilitate the body reaching an equilibrium temperature of 42.0-43.9 (but more preferably between 42.5 and 43.8) degrees Celsius (or any of the ranges or temperatures discussed above). As another example, system 100 can be used to cause blood from patient 102 to be extracted, heated, and then returned to patient 102 using a cannula (or other device) in any other vein of the patient's body, or in any combination of one or more veins in the patient's body. Furthermore, system 100 may be used to cause blood from patient 102 to be extracted from a different vein (or veins) than the vein (or veins) where the blood is returned to patient 102. System 100 may be used to deliver the heated blood to the patient (or the heart of the patient) at 4-7 liters per minute (or any of the other flow rates discussed below) on average.

In some embodiments, system 100 can be used in a veno-arterial system. Blood taken from a vein of patient 102 may be treated by the system 100 and the heated blood can be returned back into the body of patient 102 using an artery. Furthermore, blood taken from one or more veins of patient may be treated by the system 100 and the heated blood can be returned back into the body of patient 102 using one or more arteries (or vice versa). In some embodiments, this configuration can mostly bypass the heart. System 100 can deliver the heated blood to the patient at 4-7 liters per minute (or any of the other flow rates discussed below) on average. While the above options are preferable, any combination of extraction from veins or arteries and return of the blood to any combination of veins or arteries could be used without departing from the scope of the invention.

According to the illustrated embodiment, system 100 may include pump 104. In some embodiments, pump 104 can be configured to use flow rates in the range of 4 to 7 liters per minute. For example, pump 104 may be configured to cause the blood flow rate to be between 4.1 and 7 liters per minute, between 4.2 and 7 liters per minute, between 4.3 and 7 liters per minute, between 4.4 and 7 liters per minute, between 4.5 and 7 liters per minute, between 4.6 and 7 liters per minute, between 4.7 and 7 liters per minute, between 4.8 and 7 liters per minute, between 4.9 and 7 liters per minute, between 5 and 7 liters per minute, between 5.1 and 7 liters per minute, between 5.5 and 7 liters per minute, between 6 and 7 liters per minute, between 6.5 and 7 liters per minute, between 5 and 6.5 liters per minute, between 5 and 6 liters per minute, between 5 and 5.5 liters per minute, or any other range between 4-7 liters per minute. In other embodiments, average flow rates of 8 liters, 9 liters, or 10 liters per minute can be used. Flow rates above 4 liters per minute can provide advantages. One example is that flow rates above 4 liters per minute can facilitate even distribution of the heated blood throughout the body. Another example is that flow rates above 4 liters per minute can avoid subjecting the body's blood to temperatures that can destroy a substantial amount of good blood cells. For example, in one embodiment, the blood is not subjected to temperatures at or higher than 43.9 degrees Celsius (or higher than any of the above-discussed ranges or temperatures). Faster flowing blood may also facilitate more rapid heating of the body to achieve hyperthermia. Faster flow rates may allow for certain rates disclosed herein of operation of one or more components of FIG. 1 (such as reintroduction system 116, oxygenator 114, venting system 108, and toxin removal system 106) Note that the above flow rates could all be instantaneous flow rates or average flow rates over time.

In some embodiments, the flow rate of the blood may be determined in any manner known in the medical field. For example, the flow rate of the blood may be determined based on a measurement taken at a single area of the patient's body, based on measurements taken at multiple areas of the patient's body, based on measurements takes at a single area of the path of system 100 (e.g., a measurement taken when the blood exits pump 104), based on measurements taken at more than one area of the path of system 100 (e.g., an average of a measurement taken when the blood enters pump 104 and a measurement taken when the blood exits pump 104), or any combination of the preceding (e.g., an average of measurements taken at one or more areas of the patient's body and one or more areas of the path of system 100).

Furthermore, in some embodiments, the flow rate of the blood may include a flow rate that is maintained during all, or substantially all, of the procedure. For example, the flow rate of the blood may be maintained while the core temperature of the patient's body is raised to the above-discussed ranges or temperatures (e.g., 20 minutes to 1 hour, or any of the durations discussed below) and while the temperature of the patient's body is maintained within one or more of the above-discussed ranges or temperatures (e.g., 15 minutes to 6 hours, or any of the durations discussed below). Additionally, maintaining the flow rate of the blood during all, or substantially all, of the procedure may include maintaining the flow rate of the blood at the above-discussed flow rate ranges throughout the entire duration of all, or substantially all, of the procedure, or throughout a substantial portion of all, or substantially all, of the procedure. For example, the flow rate of the blood may increase above (or decrease below) the above-discussed flow rate ranges for short periods during all, or substantially all, of the procedure. However, the average flow rate of the blood during all, or substantially all, of the procedure (or for a specific time period of the procedure such as 15 minutes, 30 minutes, 45 minutes, 1 hour, 1.5 hours, 2 hours, 2.5 hours, 3 hours, 3.5 hours, 4 hours, 4.5 hours, 5 hours, 5.5 hours, or any fraction of one of these time periods) may be at the above-discussed flow rate ranges. Furthermore, maintaining the flow rate of the blood during all, or substantially all, of the procedure may include causing pump 104 to pump the blood at any flow rate that causes the flow rate of the blood to be maintained. For example, in order to maintain the flow rate of the blood, the pump 104 may pump the blood at an increased or decreased rate (or may not pump the blood at all) for short periods.

Using the above-discussed flow rate ranges, system 100 may be used to raise the core body temperature to at least 42 degrees Celsius (or any of the other temperatures set forth above) within 45 minutes. Certain previous methods of induced hyperthermia utilize blood flows between 1 to 1.35 liters per minute. Due to these rates, achieving a core body temperature that is at or above 42 degrees Celsius within 45 minutes required subjecting the blood from the patient to temperatures between 44-48 degrees Celsius for a portion of time. Unfortunately, heating the blood to 44-48 degrees Celsius can harm the blood, kill healthy cells (including red and white cells), damage plasma, and cause other potential damage.

System 100 can cause blood flow rates greater than 4 or 5 liters (or greater than the other flow rates set forth above) per minute and heat the patient's blood to a temperature of between 42 and 43.2 degrees Celsius (or any of the other ranges above) to cause the core body temperature (or substantially all of the body's temperature) to be raised to 42 degrees Celsius or above (e.g., to 42.5 degrees Celsius) within 45 minutes. Or, in other embodiments the temperature may be above 42 degrees Celsius and below 43.8 degrees Celsius or below, for example, 43.5 degrees Celsius. Thus, system 100 can be used to heat the body up to a temperature of 42.5 degrees Celsius in all, substantially all, a majority of, or in the core of the body and to maintain that temperature for a period of 2 hours or up to, e.g., 6 hours (or any of the above time ranges). The temperature that system 100 heats the body to can range from 42 to 43.9 degrees Celsius, or any of the temperature ranges or temperatures discussed above. In so doing, system 100 may facilitate the death of cancer cells while healthy cells may continue to live. System 100 can thus enable induced hyperthermia in a safer manner than previous techniques. The core temperature can be measured in the stomach. Other methods of measuring the temperature of the body to determine if it has been raised to the desired range include measuring the temperature anally, in the tympanic membrane, in the esophagus, in the blood exiting the body into the path, or in any other suitable location.

Although system 100 is illustrated as only including a single pump 104, system 100 may include more than one pump 104, such as 2 pumps 104, 3 pumps 104, 4 pumps 104, 5 pumps 104, or any other number of pumps 104. Furthermore, although system 100 illustrates pump 104 as being located in a particular area of system 100, pump(s) 104 may be located at any area of system 100, such as immediately before and/or after toxin removal system 106, venting system 108, heat exchanger 110, oxygenator 114, and/or reintroduction system 116. Additionally, pump(s) 104 may be integrated with (or otherwise included with) one or more of toxin removal system 106, venting system 108, heat exchanger 110, oxygenator 114, and reintroduction system 116.

According to the illustrated embodiment, system 100 may include toxin removal system 106. In some embodiments, toxin removal system 106 removes certain toxins from the blood before, during, or after hyperthermia. As an example, such toxins can be created during the induced hyperthermia caused by system 100 due to the death of cancer cells; in some situations, it can be damaging to the body if such toxins are not removed. The induced hyperthermia can cause destruction and death of all, substantially all, or a significant amount (e.g., greater than 5%, 10%, 20%, 30%, 40%, 50%, 60%, 70%, 80%, or 90%) of cancer tissue in tumors as well as of cancer cells themselves. This can cause an increased amount of toxins in the body. Toxin removal system 106 may perform (or otherwise implement) dialysis (e.g., diffusion dialysis and convection dialysis) or any other toxin removal procedure to remove these toxins. Dialysis can be configured in accordance with various considerations such as the sizes and molecular weights of the toxins, the methods to remove the toxins, and the ability of the dialysis process to maintain the body with PH balanced electrolyte homeostasis. The dialysis process can assist in maintaining balanced chemistry in the patient's body during the procedure. This can increase safety of the patient and avoid harm or even death. For example, some toxins (e.g., pro inflammatory mediators like Interlukin and Cytokines) can be in the range of 12,000 to 30,000 Daltons. In some embodiments, toxins created by cancer cell death can be in that range and some may be even greater (e.g., 40,000 to 50,000 Daltons or higher). In various embodiments, the amount of toxins and pro inflammatory mediators created by cancer cell death can vary from patient to patient, by type of cancer, by number of cancer cells, and by mass of cancer tissue. Other factors can also affect the amount of toxins and pro inflammatory mediators created by cancer cell death. Toxin removal system 106 can also add fluid (e.g., electrolyte-balanced and acid-balanced plasma water) to the blood to facilitate physiological homeostasis. Toxin removal system 106 can add fluid after filtration of blood but prior to the blood returning to the path of system 100. Toxin removal system 106 can include suitable structures configured to add the fluid, such as pumps, containers, tubes, and valves. Such structures can be part of or separate from the portions of toxin removal system 106 that filter substances out of the blood.

Toxin removal system 106 may, as an example, comprise a diffusion dialysis system that utilizes an ultrafiltration membrane cartridge with an effective removal ability of 0.01 to 5,000 or 6,000 Daltons. Maintenance of electrolyte homeostasis can be achieved using PH-balanced replacement fluids (e.g., sodium chloride, potassium chloride, bi-carb and calcium). In some embodiments, toxin removal system 106 can use convection dialysis in addition to, or as an alternative to, diffusion dialysis; convection dialysis can better remove toxins in the range of 1 to 50,000 Daltons or higher. One example of convection dialysis is Continuous Veno Veno Hemofiltration (CVVH). CVVH has been FDA approved for maintaining physiological homeostasis. In some embodiments, convection dialysis uses a pressure gradient (e.g., between the blood and a solution separated by a filter medium) to force plasma water that contains the toxins and other undesirable inflammatory mediators through a filter medium and into a waste container. Simultaneously or at substantially the same time, plasma water that is electrolyte- and acid-balanced can be returned to the blood after filtration. This can assist in maintaining physiologic homeostasis and proper fluid balance. Fluids removed from the blood using toxin removal system 106 may be analyzed with sensing equipment. The fluid returned to the blood can have ingredients added based upon the sensing of the extracted fluid in order for a physiologic homeostasis and proper fluid balance to be facilitated.

As an example, blood flow rates in the convection dialysis used in toxin removal system 106 can range between 200 and 7,000 milliliters per minute (or any of the flow rate ranges discussed above). In some embodiments, toxin removal system 106 can cause a convection dialysis flow rate, taken as a slip stream from the full flow of blood from patient 102, of, as examples, 600-900 milliliters per minute, 0.7 liters per minute, 0.8 liters per minute, 0.9 liters per minute, 1 liter per minute, 1.1 liters per minute, 1.2 liters per minute, 1.3 liters per minute, 1.4 liters per minute, 1.5 liters per minute, 1.6 liters per minute, 1.7 liters per minute, 1.8 liters per minute, 1.9 liters per minute, 2 liters per minute, 2.1 liters per minute, 2.2 liters per minute, 2.3 liters per minute, 2.4 liters per minute, 2.5 liters per minute, 2.6 liters per minute, 2.7 liters per minute, 2.8 liters per minute, 2.9 liters per minute, and 3 liters per minute. The flow of blood caused by pump(s) 104 (e.g., at or above 4 liters per minute) can, in various embodiments, enable flow rates in toxin removal system 106. In some embodiments, convection dialysis can better remove toxins than diffusion dialysis; for example, diffusion dialysis may not effectively remove the sizes of the pro inflammatory mediators and toxins created by the death of the cancer cells during induced hyperthermia (e.g., sizes over 5,000 or 6,000 Daltons). One or more monitors can be used as part of toxin removal system 106 to determine what is being removed from the blood (e.g., both toxins and beneficial matter). Blood gas analyzers are examples of such monitors. As other examples, blood liquid analyzers can be used to monitor one or more physiological functions of the patient during various times of the procedure.

In some embodiments, toxin removal system 106 may be enclosed in an insulative cover. As an example, a cover made of Styrofoam or other suitable insulative material may be placed over and/or around toxin removal system 106. This may help reduce the amount of heat dissipated from the blood as it passes through toxin removal system 106. Ports or other suitable access points may be included in the insulative cover to allow access to toxin removal system 106. For example, plastic doors can be used in the insulative cover to allow viewing and/or access to toxin removal system 106.

In some embodiments, toxin removal system 106 can be a single device. For example, toxin removal system 106 can be a single dialysis machine. In some embodiments, toxin removal system 106 can be multiple devices. For example, toxin removal system 106 can be multiple dialysis machines used in parallel. In some embodiments (as illustrated in FIG. 1), blood provided to toxin removal system 106 can be taken as a slip stream from the full flow of blood from patient 102. In some embodiments, one or more pumps 104 may provide blood directly (or indirectly) to toxin removal system 106. As such, all (or substantially all) of the blood removed from the patient 102 may be provided to toxin removal system 106, rather than sending some to that system and some through pump 104. In such a system, toxin removal system 106 would be inline with the rest of the path at some point. Furthermore, in some embodiments, one or more units of blood (and/or saline) may be injected (or otherwise added) into the path and/or patient 102 to make up for the amount of blood being provided to toxin removal system (and/or other components of system 100). These injections of blood (and/or saline) may be provided at any area of system 100, such as into patient 102, immediately before and/or after toxin removal system 106, or any other area. Alternatively, they could be provided to the patient directly.

Like the location of pump 104, toxin removal system 106 could be placed anywhere within the path, in a separate path (e.g., loop) branched off of the path such that a portion of the blood flowing in the path is branched to toxin removal system 106, or omitted from the path. Toxin removal system 106 could also have one or more apparatuses within it to heat the blood to any of the ranges set forth above. For example, it might have heated tubing of one of the types discussed herein. Toxin removal system 106 may also include one or more pumps. It is also possible to have multiple toxin removal systems either within the path or coupled to the path. Where multiple toxin removal systems are used, they could be coupled to the path in the same location or in multiple locations and could form one loop or a separate loop.

In some embodiments, toxin removal system 106 can be configured to operate after system 100 has completed causing blood of patient 102 to be at a temperature high enough to induce hyperthermia in patient 102. For example, toxin removal system 106 can continue to operate for, e.g., 15 minutes to 48 hours on blood in the path external to patient 102 after system 100 has ceased heating the blood of patient 102 to a sufficient degree to induce hyperthermia (e.g., during a cool down period). The blood in the path can, in some embodiments, continue to be heated while toxin removal system 106 continues its operation. For example, instead of heating the blood to between, e.g., 42-43.9 degrees Celsius (in order to induce hyperthermia), the blood can be heated to, e.g., between 36.5 to 37.5 degrees Celsius. Heating blanket(s) can be used to help reduce or prevent the chance of hypothermia.

In some embodiments, toxin removal system 106 can be used to facilitate treatment of patients undergoing various procedures that do not necessarily involve inducing hyperthermia, including chemotherapy. Toxin removal system 106, e.g., can remove the toxins that could otherwise harm or kill a patient undergoing such procedures. As an example, by removing such toxins kidney poisoning can be reduced or prevented; such poisoning can, in certain situations, lead to kidneys shutting down temporarily or permanently. Toxin removal system 106 can, in some embodiments, reduce or prevent damage to bone marrow due to toxins; damage to bone marrow can impede or stop the production of blood platelets temporarily or permanently. This can lead to harm to the patient that can culminate in death. For example, toxin removal system 106 can prevent or reduce the chances of a patient's relative platelet number dropping below 25,000 (e.g., at, near, or below 10,000). In some embodiments, system 100 can include toxin removal system 106 but not include other components such as heat exchanger 110 and heat source 112 and thus provide treatment to the blood of a patient without substantially heating the blood of the patient. As an example, system 100 can be configured to treat the blood of a patient undergoing chemotherapy; the blood of the patient can be treated using toxin removal system 106. This can remove toxins in the blood caused by the chemotherapy and improve a patient's chances of not being damaged from, or dying from, chemotherapy treatment (e.g., such as if the patient is undergoing heavy dosages of chemotherapy or fast-acting chemotherapy). In a similar manner, toxin removal system 106 can be used with treatments other than chemotherapy that also cause toxins to increase in the blood, such as radiation treatment, proton therapy, treatments for Ebola, Hepatitis C, viruses, bacteria, and diseases (such as staph infections). In some embodiments, one or more of the flow rates associated with toxin removal system 106 discussed herein. The blood of the patient can optionally be treated by other aspects of system 100 discussed herein.

In some embodiments, venting system 108 is included in system 100 and configured to vent undesirable gases (e.g., carbon dioxide and/or carbon monoxide) from the blood in the path. As an example, venting system 108 may include a filter that facilitates venting of carbon dioxide and/or carbon monoxide. Suitable filters include (as examples): membrane filters (e.g., an oxygenator in line with a vent), adsorptive filters, and absorptive filters. The filter may have a cross-flowing (or reverse-flowing) flow of a fluid (e.g., a gas or a liquid such as oxygen or ozone) on the other side from the blood. The cross-flow may be, for example, 0.01-8 liters per minute; examples of gases used in the cross-flow include nitrogen and oxygen (e.g., medical grade nitrogen and oxygen). This may facilitate the venting of carbon dioxide (and/or carbon monoxide) from the blood by facilitating the flow of carbon dioxide (and/or carbon monoxide) across the membrane of the filter. Furthermore, this cross-flowing (or reverse-flowing) flow of fluid may be generated according to any known technique. An example of venting system 108 is described further in FIG. 7.

Venting the carbon dioxide from the blood may be advantageous in various embodiments. During induced hyperthermia, in some embodiments, the cardiovascular output and respiratory output of patient 102 is increased. The death of cancer cells and the stress put on all cells can cause a buildup of carbon dioxide in the blood. In some situations, giving patient 102 100% oxygen and increasing the ventilator to full capacity is not sufficient to treat the excess carbon dioxide. Removing the carbon dioxide can prevent a cardiac arrhythmia, a heart failure, or other health failure of patient 102. Hence, venting the carbon dioxide in the path can be advantageous. In some embodiments, venting system 108 can be included as part of (or integrated with) other components of system 100 (e.g., heat exchanger 110).

In some embodiments, venting the carbon dioxide from the blood may include lowering and/or maintaining the amount of carbon dioxide in the patient (and/or in the blood) to a measurement in the range of 35 to 60 Millimeters of Mercury (mmHg), and preferably to 35 to 45 mmHg. In some embodiments, venting the carbon dioxide from the blood may include lowering and/or maintaining the amount of carbon dioxide in the patient (and/or in the blood) to other suitable ranges, such as 35 to 100 mmHg, 40 to 100 mmHg, 45 to 100 mmHg, 50 to 100 mmHg, 55 to 100 mmHg, 60 to 100 mmHg, 65 to 100 mmHg, 70 to 100 mmHg, 75 to 100 mmHg, 80 to 100 mmHg, 85 to 100 mmHg, 90 to 100 mmHg, 95 to 100 mmHg, 35 to 95 mmHg, 35 to 90 mmHg, 35 to 85 mmHg, 35 to 80 mmHg, 35 to 75 mmHg, 35 to 70 mmHg, 35 to 65 mmHg, 35 to 55 mmHg, 35 to 50 mmHg, 40 to 60 mmHg, 45 to 60 mmHg, 50 to 60 mmHg, 55 to 60 mmHg, or any other range between 35 to 100 mmHg. In some embodiments, venting the carbon dioxide from the blood may include lowering and/or maintaining the amount of carbon dioxide in the patient (and/or in the blood) to any measurement below 150 mmHg, any measurement below 140 mmHg, any measurement below 130 mmHg, any measurement below 120 mmHg, any measurement below 110 mmHg, any measurement below 100 mmHg, any measurement below 95 mmHg, any measurement below 90 mmHg, any measurement below 85 mmHg, any measurement below 80 mmHg, any measurement below 75 mmHg, any measurement below 70 mmHg, any measurement below 65 mmHg, any measurement below 60 mmHg, any measurement below 55 mmHg, any measurement below 50 mmHg, any measurement below 45 mmHg, or any measurement below 40 mmHg. Blood can flow through venting system 108 at any suitable rate, including in the range of 4-7 liters per minute.

In some embodiments, a measurement of the amount of carbon dioxide in the patient (and/or in the blood) may be taken in any suitable manner known in the medical field such as blood analyzers, gas analyzers, and liquid analyzers. As an example, the measurement may be taken based on air breathed out or expelled by the patient into equipment configured to measure carbon dioxide.

Like the other components of the path, venting system 108 can be located anywhere within the path, in a separate path (e.g., loop) branched off of the path such that a portion of the blood flowing in the path is branched to venting system 108, or omitted from the path. Venting system 108 could also have one or more apparatuses within it to heat the blood to any of the ranges set forth above. For example, it might have heated tubing of one of the types discussed herein. Venting system 108 may also include one or more pumps. Venting system 108 could also have a way to heat the filter such that blood is heated while it is filtered. It is also possible to have multiple venting systems either within the path or coupled to the path. Where multiple venting systems are used, they could be coupled to the path in the same location or in multiple locations and could form one loop or a separate loop.

In some embodiments, venting system 108 can be used to facilitate treatment of patients undergoing various procedures, including chemotherapy. Venting system 108. e.g., can remove carbon dioxide from the blood that could otherwise harm or kill a patient undergoing such procedures.

According to the illustrated embodiment, system 100 may include heat exchanger 110. In some embodiments, heat exchanger 110 may be configured to heat the blood removed and returned to patient 102. For example, heat exchanger 110 may be configured to heat the blood to a temperature that raises and/or maintains (or helps raise and/or maintain) the core temperature of all, or substantially all, of the patient's body to (or at) the above-discussed temperature ranges or temperatures (e.g., a range of 42 to 43.9 degrees Celsius, and more preferably 42.5-43.8 degrees Celsius). In some embodiments, this may cause the blood to be heated to between 43 and 44 degrees Celsius, to between 42 to 43.9 degrees Celsius, or to any of the above-discussed temperature ranges or temperatures.

Any of the above discussed temperature ranges, times, flow rates, average flow rates, etc. can be used in combination with one another without departing from the scope of the invention.

Heat exchanger 110 may utilize any suitable technique for heating blood. As an example, exchanger 110 may cause the blood to pass through tubes in contact with heated water that has been heated by heat source 112. Heat source 112 may control the water temperature and cause the heated water to flow from a reservoir (e.g., between 1 and 200 gallons in size), across or counter currently, around the tubes in the heat exchanger that carry the blood at rate in the range, e.g., of 1 liter per minute to 250 gallons per minute. Such a reservoir may be part of heat source 112 in various embodiments. The heated water, in some embodiments, may be heated to any temperature suitable for heating the blood to a temperature that raises and/or maintains (or helps raise and/or maintain) the core temperature of all, or substantially all, of the patient's body to (or at) the above-discussed temperature ranges or temperatures (e.g., a range of 42 to 43.9 degrees Celsius). Thus, the heat exchanger 110 could use heated water heated to any of the above temperatures or temperature ranges to which or within which it is desired to heat the blood. Heat exchanger 110 and/or heat source 112 may use a gas or a liquid of any suitable type as a medium for carrying heat that will be used to heat blood. The higher the viscosity of the fluid, or the higher the density of the fluid, the greater and faster the heat transfer occurs in various embodiments. Higher flow rates of the fluid will also increase the heat exchanged with the blood. While heating the blood to the desired temperature, the temperature of the fluid in contact with the heat exchanger can be configured, in some embodiments, to not exceed 43.2 degrees Celsius (or to not exceed any of the above-discussed temperature ranges or temperatures). In some embodiments, using flow rates of the fluid in the range of 1, 2, 4, 7, 9, or 10 gallons per minute (or higher such as 10, 20, 30, 50, 100, 150, or 250 gallons per minute) can facilitate heat exchange such that blood can be heated to a temperature above 42 degrees Celsius but below 43 degrees Celsius in a suitable and/or advantageous amount of time without heating the fluid above 43.2 degrees Celsius. Heat exchanger 110 can use any suitable form of heating elements to transfer heat from the gas or liquid to the blood, such as: stainless steel tubes, plates, and pleated steel plates. Examples of heat exchanger 110 are described further in FIGS. 3-4.

In some embodiments, heat exchanger 110 and/or heat source 112 can be controlled automatically to facilitate the appropriate heating of the blood using one or more of temperature probes 118*a-l* and/or heat-sensing cameras as discussed herein. For example, heat exchanger 110 and/or heat source 112 can be controlled to be set at 42.8 or 42.9 degrees Celsius; in various embodiments other suitable temperatures may be used such as those in the range of 41 to 45 degrees Celsius, or to be set to achieve heating of the blood within any of the temperature ranges or temperatures set forth above. As another example, heat exchanger 110 and/or heat source 112 can be controlled to be set between 42 and 43.9 degrees Celsius, or any of the above-discussed temperature ranges or temperatures. Temperature sensors can be placed, for example, within a water tank that supplies water to heat exchanger 110, within the tubing of heat exchanger 110 where the water flows, or within tubing of heat exchanger 110 where the blood flows. Electronic circuitry can control the temperature in response to the sensed temperature. The heat exchanger 110 does not necessarily need to use liquids or gases to heat the blood. Heating elements could heat tubes where blood is flowing using conduction or convection.

In some embodiments, heat exchanger 110 may be configured to heat the blood throughout all, or substantially all, of the procedure. For example, heat exchanger 110 may heat the blood while the core temperature of the patient's body is raised to the above-discussed temperature ranges or temperatures (e.g., 20 minutes to 1 hour, or any of the above-discussed time ranges) and while the temperature of the patient's body is maintained within one or more of the above-discussed temperature ranges or temperatures (e.g., 15 minutes to 6 hours, or any of the above-discussed time ranges). In some embodiments, heating the blood throughout all, or substantially all, of the procedure may include heating the blood throughout the entire duration of all, or substantially all, of the procedure, or throughout a substantial portion of all, or substantially all, of the procedure. For example, the heat exchanger may not heat (or may increase or decrease how much it heats) the blood for short periods during all, or substantially all, of the procedure. However, the core temperature of the patient's body may be raised to and maintained at the above-discussed temperature ranges or temperatures during all, or substantially all, of the procedure.

Although heat exchanger 110 is illustrated as being located in a particular area of the path of system 100, in some embodiments, heat exchanger may be located in any area of the path. For example, heat exchanger 110 can be located in an area immediately before and/or after patient 102, immediately before and/or after pump 104, immediately before and/or after toxin removal system 106, immediately before and/or after venting system 108, immediately before and/or after oxygenator 114, and/or immediately before and/or after reintroduction system 116. Heat exchanger 110 may include one or more pumps 104 to pump blood and/or one or more pumps to pump water through tubes in the heat exchanger.

Furthermore, although system 100 is described above as including heat exchanger 110 and/or heat source 112, in some embodiments, system 100 may alternatively (or additionally) include other components for heating the blood of the patient. For example, in some embodiments, some or all of the lines carrying the blood in the path of system 100 between components can be enclosed in one or more heated tubes. In such an example, the line(s) carrying the blood can be enclosed in a tube that has heated water (or other suitable liquid or gas) flowing across it. The tube can be heated to a temperature in the range of 42-43.9 degrees Celsius, or to any of the temperature ranges or temperatures discussed above. A temperature probe can be used to verify that the water (or other suitable liquid or gas) used to heat the heated tube is not above 43.2 degrees Celsius, or not above any of the temperature ranges or temperatures discussed above. The water can be heated using heat exchanger 110 (and/or heat source 112) or a separate heat exchanger (and/or heat source), or both. Heated tubes may also be within any of the components of the path.

According to the illustrated embodiment, system 100 may include oxygenator 114. In some embodiments, oxygenator 114 is configured to introduce oxygen into the blood (and/or remove carbon dioxide from the blood). Oxygenator 114 can be implemented using a microporous membrane made of hollow fibers that are permeable to gas but impermeable to blood. In some embodiments, blood may flow on the outside of the hollow fibers, and oxygen may flow in an opposite direction on the inside of the fibers. For example, the oxygen may flow at a rate of 0.1 to 10 liters per minute. This may allow the blood cells in the blood to absorb oxygen molecules directly. The use of oxygenator 114 can be useful due to, e.g.: pulmonary complications, cardiac de-compensation, a patient's need for oxygen to reduce the risk of damage above the amount that can be administered by a ventilator (e.g., a patient with damaged lungs, such as one experiencing lung cancer, may need more oxygen), or other conditions. The blood can be flowing through oxygenator 114 at speeds including 4-7 liters per minute (or any of the above-discussed blood flow rates). The oxygenator can introduce between 0.2 to 5 liters per minute of oxygen into the blood (e.g., 1 liter per minute). Administration of oxygen may assist healthy cells and/or may facilitate killing of unhealthy cells (e.g., cancer cells or other cells deleterious to the body). In some embodiments, an electromagnetic flow probe can be placed on the return line distal to heat exchanger 110 and/or oxygenator 114 to measure flow being delivered back to patient 102 from the path. In some embodiments, oxygenator 114 can be incorporated into heat exchanger 110. Oxygenator 114 can be placed anywhere within the path, in a separate path (e.g., loop) branched off of the path such that a portion of the blood flowing in the path is branched to oxygenator 114, or omitted from the path. It is also possible to have multiple oxygenators either within the path or coupled to the path. Where multiple oxygenators are used, they could be coupled to the path in the same location or in multiple locations and could form one loop or a separate loop.

In various embodiments, oxygenator 114 can be operating in different manners during some or all of the time that blood is being pumped from, and delivered to, patient 102. Oxygenator 114 may be configured to add oxygen and/or ozone (or a free radical or substance that reacts with some other substance to form a free radical) at one rate during one portion of the time that blood is being pumped from, and delivered to, patient 102 and at another rate during a different portion of that time. For example, during the first 90 minutes of heating the blood of patient 102 as described above, oxygenator 114 can be configured to deliver 0.05 liters per minute of oxygen to the blood. After those 90 minutes, oxygenator 114 can be configured to deliver 3 liters per minute of oxygen to the blood for a desired length of time (e.g., and not by way of limitation, up to 5 hours). Oxygenator 114 can be configured to deliver any suitable amount of oxygen during any suitable time periods. In various embodiments, oxygenator 114 can be configured to deliver, as an example, between 0.01 and 0.1 liters per minute of oxygen during a first time period in the range of 30-120 minutes and 0.1-10 liters per minute of oxygen during a second time period in the range of 30-360 minutes that occurs after the first time period. In some embodiments, delivering a greater amount of oxygen after a period of time wherein the blood of patient 102 is heated may facilitate the death of unhealthy cells (e.g., causing reperfusion injury). In some embodiments, venting system 108 may be used with oxygenator 114 or in place of oxygenator 114; venting system 108 can be configured to deliver oxygen in the same variety of manners as discussed above with respect to oxygenator 114.

According to the illustrated embodiment, system 100 may include reintroduction system 116. Reintroduction system 116 could be placed anywhere within the path, in a separate path (e.g., loop) branched off of the path such that a portion of the blood flowing in the path is branched to reintroduction system 116, or omitted from the path. It is also possible to have multiple reintroduction systems either within the path or coupled to the path. Where multiple reintroduction systems are used, they could be coupled to the path in the same location or in multiple locations and could form one loop or a separate loop.

In some embodiments, reintroduction system 116 may be used to introduce chemicals or nutrients into the blood. As an example, suitable pharmaceuticals, vitamins (in liquid form), and/or nutritional elements (e.g., liquid food and/or glucose) may be introduced into the blood. Examples of suitable nutrients that may be introduced into the blood may include total parenteral nutrition (TPN), total nutrient admixture (TNA), parenteral nutrient (PN), and/or peripheral parenteral nutrient (PPN). Other suitable chemical or nutrients that may be introduced into the blood may include glucose, amino acids, lipids, vitamins, minerals, sodium, chloride, potassium, bicarbonate, calcium, magnesium, -balanced fluids, acid-balanced fluids, or any combination of the preceding. Administration of such pharmaceuticals, vitamins, and/or nutritional elements may assist healthy cells and/or may facilitate killing of unhealthy cells (e.g., cancer cells or other cells deleterious to the body). Reintroduction system 116 may operate at any suitable rate, including between 6.5 to 26 liters per hour. As examples, reintroduction system 116 can operate at 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, 20, 20.1, 20.2, 20.3, 20.4, 20.5, 20.6, 20.7, 20.8, 20.9, 21, 21.1, 21.2, 21.3, 21.4, 21.5, 21.6, 21.7, 21.8, 21.9, 22, 22.1, 22.2, 22.3, 22.4, 22.5, 22.6, 22.7, 22.8, 22.9, 23, 23.1, 23.2, 23.3, 23.4, 23.5, 23.6, 23.7, 23.8, 23.9, 24, 24.1, 24.2, 24.3, 24.4, 24.5, 24.6, 24.7, 24.8, 24.9, 25, 25.1, 25.2, 25.3, 25.4, 25.5, 25.6, 25.7, 25.8, 25.9, and/or 26 liters per hour.

In some embodiments, reintroduction system 116 may be composed of one or more reintroduction modules. For example, a reintroduction module can include a suitable combination of one or more pumps (e.g., which can be implemented using the teachings discussed herein with respect to pumps 104), tubing, interfaces, valves, and locks. In some embodiments, one or more aspects of reintroduction system 116 (e.g., one or more reintroduction modules) can be included in other aspects of system 100 such as oxygenator 114, venting system 108, pump 104, and toxin removal system 106. Reintroduction system 116 may include one or more pumps 104 and/or heated tubing or another apparatus for heating blood or other fluids introduced by reintroduction system 116. Examples of suitable temperatures that the material being introduced by reintroduction system 116 are: 35, 35.5, 36, 36.5, 37, or 37.5 degrees Celsius. In some embodiments, external heating sources can be applied to patient 102 in conjunction with introducing material into the blood using reintroduction system 116. For example, one or more water heating blankets can be placed on patient 102 (e.g., 2, 3, 4, 5, or 6 blankets may be used). Such heating blankets can be in temperature range of, e.g., 40 to 43.5 degrees Celsius. In some embodiments, reintroduction system 116 can be configured to provide such chemicals and/or nutrients at rate that is less than, equal to, or greater than the rate at which toxin removal system 106 removes material from the blood of patient 102. Examples of rates at which reintroduction system 116 operates are within the range of 200 to 5000 milligrams per minute. Examples of the rates at which reintroduction system 116 operates in terms of volume include between 1 and 30 liters per hour (e.g., 8, 9, 20, 21, 22, 23, 24, 25, 26, 27, 28, 29, and 30 liters per hour); note that the volumetric rate of reintroduction system 116 can be configured to correspond to the rate volumetric removal rate of toxin removal system 106 (e.g., it can be configured to be the same as, nearly the same as, a suitable fraction of, or a suitable multiple of the volumetric removal rate of toxin removal system 106). In some embodiments, reintroduction system 116 can be configured to provide such chemicals and/or nutrients such that the pH level of the blood is directed towards a desirable range (e.g., 7.35+/−0.01).

In some embodiments, reintroduction system 116 can be used to introduce blood or platelets. Such blood can be selected so as to have a type and RH factor that matches the blood of patient 102 or O-negative blood can be used. Platelets can be added, e.g., if platelet levels fall below 50,000 platelets per microliter (or other suitable amount). Such introduction of blood can provide one or more benefits. As examples, it can benefit: an anemic patient, a patient with a reduced amount of healthy blood (e.g., due to cancer or therapies), a patient whose blood is traveling through other components of system 100 (e.g., oxygenator 114, heat exchanger 110, and toxin removal system 106) by supplementing the amount of blood available to the patient, system 100 by charging or priming certain components (e.g., oxygenator 114, heat exchanger 110, and toxin removal system 106).

According to the illustrated embodiment, system 100 may include support system 103. In some embodiments, support system 103 can be used to sedate patient 102 and can include a ventilator. Patient 102 may be injected with 2 liters (or other suitable amount) of heated water or saline water at 43.2 degrees Celsius (or with a heated range of 42-43.9 degrees Celsius, or any of the above-discussed temperature ranges or temperatures). This can be injected into the body via one or more veins and/or arteries and can facilitate raising the core temperature of the body. Support system 103 can be used to administer anesthesia (e.g., sevoflurane) to patient 102. The anesthesia can be general anesthesia. The anesthesia can cause the hypothalamus to stop controlling (or reduce its capability to control, or substantially prevent its ability to control) the temperature of the patient's body. As such, system 100 may be used to raise the temperature of the patient's body without interference from the hypothalamus, thereby allowing for an even (or substantially even) distribution of temperature throughout all, or substantially all, of the patient's body. Examples of the anesthesia may include one or more barbiturates (e.g., sodium pentothal), hypnotics (e.g., propofol, ketamine, and etomidate), anesthetic gases (e.g., isoflurane, sevoflurane, desflurane, nitrous oxide) and/or narcotics (e.g., fentanyl, alfentanil, sufentanil, meperedine, morphine, hydromorphone). The anesthesia may be administered in a sufficient medically safe dosage to prevent or substantially prevent the hypothalamus from controlling the temperature of the patient's body, as would be understood by an anesthesiologist. Additionally, one or more preparations can be performed on the patient such as intubating the patient and using a ventilator. Support system 103 can also be used to administer other substances, such as medications. For example, edema (such as cerebral edema) can occur in patient 102 as a result of treating (e.g., brain cancer) using system 100. Support system 103 can be configured to administer medications to counteract bad effects of edema; such medications include albumin (e.g., which can be used to prevent or reduce edema generally) and Mannitol (e.g., which can be used to prevent or reduce cerebral edema).

If the patient is using a ventilator, heated air may be used in the ventilator (e.g., air heated to between 42 and 43 degrees Celsius, or any of the above-discussed temperature ranges or temperatures to which the blood can be heated). For example, support system 103 can include monitoring devices for monitoring vital signs or other aspects of patient 102 (e.g., blood pressure).

In some embodiments, support system 103, reintroduction system 116, oxygenator 114, and/or venting system 108 may be used to introduce one more free radical or unstable substances that facilitate or increase the production of reactive oxygen species within the blood of patient 102. For example, such a substance could be an unstable substance such as ozone that reacts with oxygen to form a free radical. Radiation therapy can be used along with or as an alternative to introducing such substances to facilitate or increase the production of reactive oxygen species within the blood of patient 102. As an example, introducing such substances or employing radiation this can occur once or after the temperature of one or more aspects of patient 102 has reached a temperature of 42 degrees Celsius or higher (or above 42.1, 42.2, 42.3, 42.4, 42.5, 42.6, 42.7, 42.8, 42.9, 43, 43.1, 43.2, 43.3, 43.4, 43.5, 43.6, 43.7, or 43.8 degrees Celsius); as another example, adding the substance(s) can occur at any time during the procedure described herein. It is believed that any of the above techniques that increase the amount of reactive oxygen species during the procedure can facilitate the death of, or damage to, harmful cells such as cancer cells when those cells are under stress due to the temperature at which the procedure is performed. The increased activity regarding reactive oxygen species can be sustained using substances introduced via support system 103 and/or reintroduction system 116 as well as the heating of the blood of patient 102 by system 100. Examples of such substances include: ozone, Freon, copper (e.g., copper ions), iron (e.g., iron ions), chemotherapeutic agents (such as alkylating agents, anti-metabolites, anti-microtubule agents, topoisomerase inhibitors, and cytotoxic antibiotics), iron, oxidized iron, an oxidized metallic substance, any suitable substance (including medicinal drugs) that includes, or promotes the development of, free radicals, or any suitable substance (including medicinal drugs) that includes, or promotes the development of unstable molecules (e.g., molecules that are prone to take electron(s) from other molecules) such as, for example, unstable molecules that cause the formation of free radicals. These substances, when in solid or liquid form, can be introduced into patient 102 through a port, directly into a vein or artery with a syringe, using support system 103, using reintroduction system 116, or other suitable method. In some embodiments, the use of substances that cause increased activity regarding reactive oxygen species (e.g., iron gluconate and chemotherapeutic agents) in system 100 can cause greater beneficial effects than if such substances were to be used without system 100. For example, the heating treatment provided for by system 100 can enhance the effect of such substances (e.g., the rate at which such substances cause increased activity regarding reactive oxygen species can be greater when used within system 100).

For example, an iron preparation (e.g., one or more of iron sucrose, iron gluconate, and iron dextran) can be administered intravenously during a suitable number of hours (e.g., 2, 3, 4, 5, or more hours). A preparation of FERRLECIT can be administered in a dose of, e.g., 30 milligrams at time and a total of, e.g., 500 milligrams during the course of the procedure in various embodiments. As another example, a preparation of FERRLECIT can be administered in a dose of, e.g., 60 milligrams at time and a total of, e.g., 500 milligrams during the course of the procedure. As another example, a preparation of FERRLECIT can be administered in a dose of, e.g., 125 milligrams one hour into the procedure and a total of, e.g., 500 milligrams during the course of the procedure. In various embodiments, iron preparations can be administered such that a total of between 60 and 500 milligrams is administered over a period of, e.g., three hours during the procedure; for example, a range of 125 to 375 milligrams of an iron preparation may be administered to the patient during the procedure itself.

In some embodiments, it is believed that the introduction of one more free radical or unstable substances into the blood of patient 102 can facilitate excessive levels of reactive oxygen species. For example, if ozone is introduced into the blood, it can react with oxygen in the blood and release one or more electrons from one or more of its molecules. Such molecules may become unstable and seek one or more electrons from other molecules. These other molecules can include molecules in harmful cells such as cancer cells. In some situations, the electron(s) are more likely to come from harmful cells (e.g., cancer cells) because of the temperature of patient 102 being raised to, e.g., 42 degrees Celsius or higher. The molecules in harmful cells that have given up electron(s) will seek it from other molecules, and a likely source of such electrons are other molecules in the same harmful cell. As this process of taking electrons from other molecules within harmful cells repeats itself, the harmful cells become damaged and this damage can, in some embodiments, facilitate their death. Note that, in various embodiments, ozone and other free radical or unstable substances can operate in different manners than the preceding description to facilitate or increase the production of reactive oxygen species, and, in turn, to facilitate the damage or death of cancer cells.

As another example, it is believed that elemental iron can facilitate generation of hydroxyl by, e.g., facilitating transfer of electrons between molecules in the blood of a patient. In some embodiments, elemental iron can also facilitate transfer of electrons by taking electrons from other molecules to facilitate an increase in reactive oxygen species in the blood of a patient. Note that, in various embodiments, iron and other substances can operate in different manners than the preceding description to facilitate or increase the production of reactive oxygen species, and, in turn, to facilitate the damage or death of cancer cells.

In various embodiments, the amount of free radical or unstable substance(s) that facilitate or increase the production of reactive oxygen species within the blood of patient 102 introduced to patient 102 can be varied depending on the substance(s) used, condition(s) or characteristics of patient 102, the amount of time the blood of patient 102 has been heated, absorption rates, and the amount of time desired for administering the substance(s). Other suitable factors may also be taken into account. The amount of substance(s) to be added can be determined, in some embodiments, by seeking an amount that will cause damage or death to harmful cells (such as cancer cells) but not to healthy cells (or an amount that will cause damage or death to healthy cells up to an acceptable amount). For example, 0.1 to 1.25 (e.g., 0.45) grams of ozone may be introduced to patient 102 using diffusion (e.g., this can be implemented using oxygenator 114 and/or venting system 108). Other pharmacologically effective amounts may be used. This dosage can be applied at one or more times during the procedure. In some embodiments, a suitable dosage of ozone at can be: any amount below 0.1 grams, any amount below 0.2 grams, any amount below 0.3 grams, any amount below 0.4 grams, any amount below 0.5 grams, any amount below 0.6 grams, any amount below 0.7 grams, any amount below 0.8 grams, any amount below 0.9 grams, any amount below 1.0 grams, any amount below 1.1 grams, any amount below 1.2 grams, or any amount below 1.3 grams.

In some embodiments, one or more of free radical substances, unstable substances, or chemotherapeutic agents can be introduced to facilitate or increase the production of reactive oxygen species within the blood of patient 102. For example, ozone and iron (e.g., iron ions such as iron(II) or iron(III)) or ozone and copper (e.g., copper ions such as copper(I) or copper(II)) may be introduced into patient 102. Adding such combinations can result in the development of reactive oxygen species in the blood of patient 102. For example, hydroxyl radicals can be produced in the blood of patient 102 as a result of adding a combination of ozone and iron ions or ozone and copper ions. In various embodiments, other suitable transition metals can be combined with free radical or unstable substances (e.g., ozone) to facilitate or increase the production of reactive oxygen species within the blood of patient 102. More than two substances can be combined.

In some embodiments, system 100 can be used to increase the effectiveness of other treatments. System 100 can be used to heat the blood of a patient and be used to administer other treatments in smaller dosages or for shorter periods of time than would otherwise be used if the blood were not heated to any of the temperature ranges disclosed herein with system 100. For example, chemotherapy dosages can be reduced and/or given for a shorter period of time (e.g., instead of giving chemotherapy treatments for weeks it can be given for hours or days) when used within system 100 or along with system 100 due to, e.g., system 100 heating the blood of a patient to any of the temperature ranges disclosed herein.

In some embodiments, system 100 can provide precise temperature control. System 100 can use the following six temperature probe locations to obtain an average core body temperature: rectal, esophagus, bi-lateral auditory canal, bladder, and pulmonary artery blood. In some embodiments, system 100 may utilize different temperature probe locations (e.g., stomach, etc.), less than six temperature probe locations (e.g., only one location), and/or more than six temperature probe locations (e.g., eight locations). System 100 can also use additional temperature monitoring and control techniques. For example, system 100 can precisely measure brain temperature. System 100 may utilize multiple infrared cameras that monitor the brain during operation; as an example, three cameras can be measuring three points on the head of the patient (e.g., neck, eyes, ears, face, etc.). System 100 can use any other alternative or additional means known in the medical field for precisely monitoring the brain temperature. Using such techniques, system 100 can monitor the brain temperature to within one-tenth of one degree Celsius (as an example). This can enhance patient safety. As an example, temperature probes 118a-l can be accurate to within one-tenth or one-hundredth of one degree Celsius and such temperature probes can be used in the esophagus, bladder, rectum, tympanic membrane(s), femoral venus catheter/cannula, and femoral superior vena cava cannula/catheter. Examples of other suitable locations for temperature probes 118a-l are illustrated in FIG. 1 and include: heat source 112, heat exchanger 110 (prior to entry of blood), heat exchanger 110 (at exit of blood), at or near where the heated blood enters patient 102, at or near where the blood exits patient 102, on a water-heated blanket, at or near where blood enters toxin removal system 106, and at or near where blood exits toxin removal system 106. System 100 can use infrared cameras, or other suitable devices, pointed to the central body as well the bottom of a patient's foot. Using one or more of these techniques, system 100 can precisely monitor body temperature.

In some embodiments, the techniques disclosed herein, including the use of temperature probes 118a-l, may allow for maintaining the body to a precise, desired temperature (e.g., between 42 and 43.9 degrees Celsius, or any of the above-discussed temperature ranges or temperatures) as well as precisely measuring the core body temperature and monitoring the patient's brain temperature during all, or substantially all, of the operation of system 100. Consistent temperature distribution over all, or substantially all, of the body (including cancer cells in all, or substantially all, of the body) can be facilitated. Such precision of measurements and of monitoring can lead to: precisely determining whether the core body temperature is at the desired temperature, determining the length of time taken to achieve the desired core body temperature, precisely monitoring the temperature that the blood and cells are being raised to throughout the procedure, and precisely monitoring the amount of time the blood and cells are being kept at the desired temperature. This can allow for increasing or maximizing the effectiveness of the treatment and avoid adverse effects of hyperthermia.

In some embodiments, one or more of the temperature probes 118a-l (or other temperature measurement devices) may communicate with a heat control system (not shown). The heat control system may be configured to increase or decrease the temperature of one or more heating components of system 100. For example, heat control system may increase or decrease the temperature of heat source 112, heat exchanger 110, one or more heated tubes, or any other heating components. The heat control system may control all (or two or more) of the heating components simultaneously, or may control each of the components separately. For example, the heat control system may decrease the temperature of the heat source 112 and all of the heated tubes simultaneously, or the heat control system may turn off the heat source 112 while keeping one or more of the heated tubes at the same temperature.

In some embodiments, one or more aspects of system 100 and/or patient 102 can be placed in a room that is at a temperature above, e.g., 77-85 degrees Fahrenheit. This can reduce the difference in temperature between patient 102 and the air temperature in the room. In some embodiments, this can result in patient 102 having its core temperature heat up faster.

The following are examples of operating configurations of system 100. These examples are not limiting to the present disclosure; rather, they serve to present the teachings discussed herein in another format to aid in understanding the teachings of the present disclosure. One example configuration is: blood may be pumped in the path at a rate between 4 and 7 liters per minute; convection dialysis at a rate between 0.6 and 2 liters per minute may be performed on the blood; blood may flow through a venting system that includes a membrane to remove carbon dioxide from, and/or add oxygen to, the blood; the blood may be heated to a temperature between 42 and 43.2 degrees Celsius for 1-3 hours and then to 35-37.5 degrees Celsius after the induction of hyperthermia is complete; 6.5-26 liters per hour of electrolyte-balanced and acid-balanced fluids may be added to the blood Modifications, additions, or omissions may be made to the system 100 without departing from the scope of the invention. For example, one or more of the support system 103, pump 104, toxin removal system 106, venting system 108, heat exchanger 110, heat source 112, oxygenator 114, and reintroduction system 116 may be optional in system 100. In such an example, system 100 may not include oxygenator 114, and/or one or more of the other components illustrated in FIG. 1 or described above. As another example, the components of system 100 may be re-arranged in any manner in system 100. In such an example, the toxin removal system 106 may be located immediately before patient 102, or at any other location. Additionally, one or more of the support system 103, pump 104, toxin removal system 106, venting system 108, heat exchanger 110, heat source 112, oxygenator 114, and reintroduction system 116 may be integrated or separated. For example, the heat exchanger 110 and the oxygenator 114 may be the same component. As another example, the reintroduction system 116 may be two separate components. Moreover, the operations of the system 100 may be performed by more, fewer, or other components. Furthermore, a single device could perform the operations of two or more of the components of system 100. For example, a single device may perform the operations of each of the support system 103, pump 104, toxin removal system 106, venting system 108, heat exchanger 110, heat source 112, oxygenator 114, and reintroduction system 116.

Figure 2:
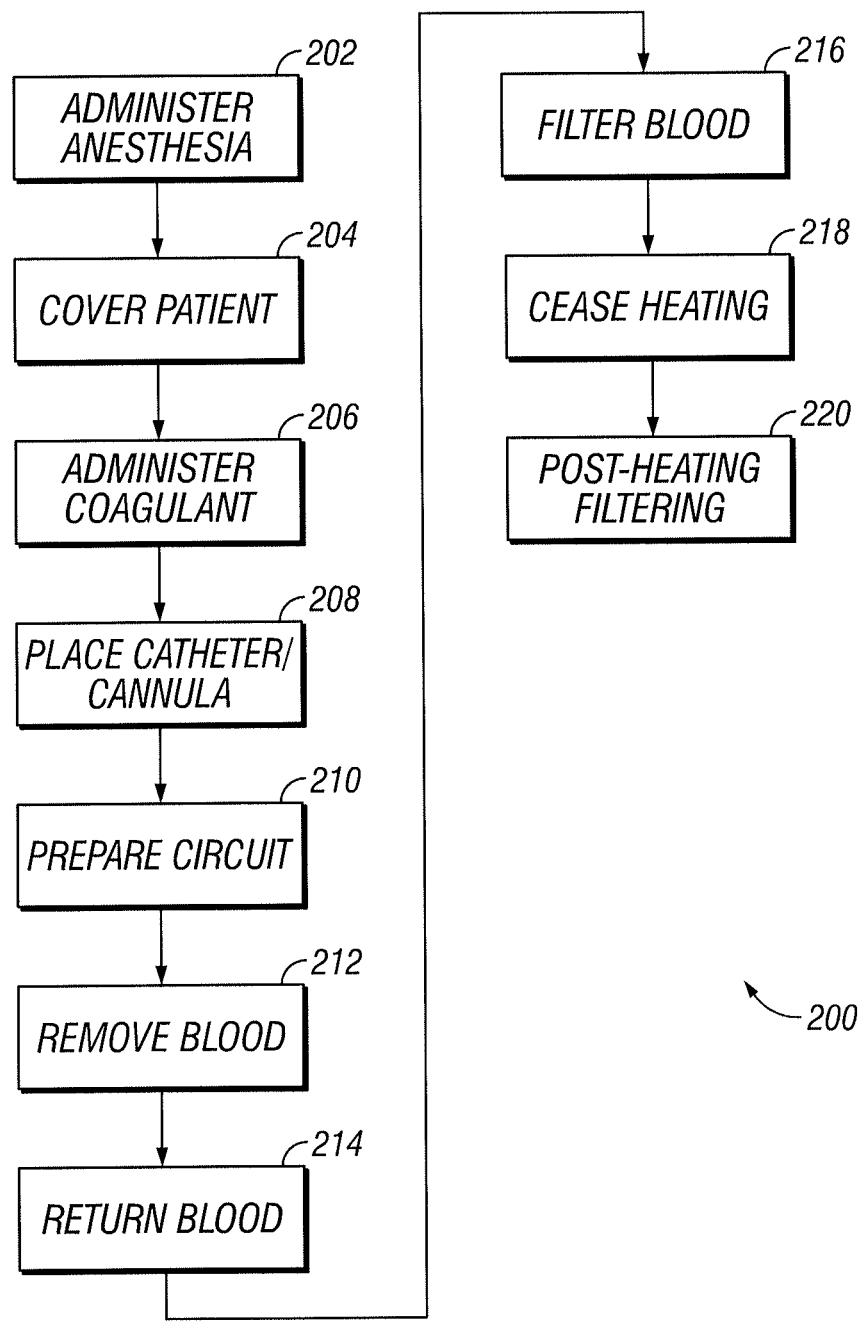
FIG. 2 illustrates one embodiment of a method for inducing hyperthermia.

FIG. 2 illustrates one embodiment of a method for inducing hyperthermia. In some embodiments, one or more steps of method 200 may be performed using one or more components of FIG. 1.

At step 202, in some embodiments, anesthesia (e.g., any of the anesthesia discussed above in FIG. 1) is administered to the patient (e.g., using support system 103 of FIG. 1). The patient can be prepared and draped in a sterile manner for the procedure. The anesthesia can be general anesthesia. The anesthesia can cause the hypothalamus to stop controlling (or substantially reduce its capability to control) the temperature of the patient's body, as is discussed above with regard to FIG. 1. One or more preparations can be performed on the patient such as intubating the patient and using a ventilator.

At step 204, in some embodiments, the patient may be covered by an insulating material. For example, water-heated blankets (e.g., including water heated to between 42 and 43.2 degrees Celsius, or to any of the temperature ranges or temperatures discussed above) and/or heat-insulating (and/or reflecting) foil can be situated on the patient. This can assist in preventing heat loss from the patient. (The blankets could be treated by another method as well.)

At step 206, in some embodiments, an anticoagulant is administered (e.g., using support system 103). For example, 10.000 units of sodium heparin can be administered intravenously. After 3 minutes of circulation time, an activated clotting time (ACT) can be determined to determine the adequacy of anticoagulation. This step can be performed throughout the procedure. ACTs can be maintained at between 200 and 300 seconds for the procedure and can be measured at, e.g., 30-minute increments. Additional heparin can be given as needed. In addition to or as an alternative, at this step, heated water (or heated blood) may be administered to the patient's bloodstream (e.g., two liters of water or blood heated to 42.9 degrees Celsius, or to any of the above-discussed temperature ranges or temperatures). This can promote hydration, faster heating of the core body temperature, and may act as an anticoagulant.

At step 208, in some embodiments, a catheter or cannula is placed into the patient's femoral vein. A standard French Femoral vena catheter or cannula (common size 22) can be used. The catheter/cannula can withdraw blood from the inferior vena cava while in a position 10 or more inches into the vein toward the heart. As another example, an Avalon double Lumen catheter/cannula can be inserted into the right jugular vein as a single catheter/cannula technique to both extract blood from the patient and return heated blood. In some embodiments, more than one vein (or one or more arteries, or both) can be used. In some embodiment, a different vein (or veins) may be used. Blood taken from the multiple veins is combined in the path. In some embodiments, it may be beneficial to use two or more veins (or arteries, or a combination) combined into one stream going into the pump. This can facilitate, in various embodiments, flow rates of, e.g., 4-7 liters per minute (or any of the flow rates ranges discussed above) of blood flow during the procedure. Any of the above options for blood vessels and/or arteries can be used that were discussed in connection with FIG. 1.

At step 208, in some embodiments, an arterial cannula/catheter is placed into the right internal jugular vein. It can be advanced into the lower portion of the superior vena cava. In some embodiments, more than one vein (or one or more arteries, or both) can be used. In some embodiment, a different vein (or veins) may be used. Catheter and cannula sizes can be determined by patient weight and blood flow requirements or desires. Ranges for these sizes can include: 18, 20, 22 and 24 French sizes for the venous catheter; and 18, 20 and 22 French sizes for the arterial cannula/catheter. Blood can be returned into a vein, such as the jugular vein.

At step 210, in some embodiments, the path can be primed and de-bubbled using a physiologic crystalloid fluid. This can be done, for example, while the cannulas/catheters are being placed. The path is then connected to the cannula and/or the catheter.

At step 212, in some embodiments, blood is drawn from the catheter by a centrifugal pump (or any other suitable pump(s)) into a heat exchanger (that may also oxygenate the blood) at approximately 4-7 liters per minute, or any of the flow rate ranges discussed above (e.g., this can be performed by pump 104, heat exchanger 110, and/or oxygenator 114 of FIG. 1). The blood flows through the heat exchanger and is heated to, e.g., 42.9 degrees Celsius (or any of the temperature ranges or temperatures discussed above). Tubes carrying the blood come into contact with heated water that has been heated by a temperature control unit (e.g., heat source 112 of FIG. 1). The temperature control unit controls the water temperature and causes heated water to flow, across or counter currently, around the tubes in the heat exchanger that carry the blood. The heated water, in some embodiments, does not exceed 43.2 degrees Celsius (or one or more of the temperature ranges or temperatures discussed above). Any of the above options for the heat exchanger (or alternatives to the heat exchanger) discussed in connection with FIG. 1 can be used.

At step 214, in some embodiments, the heated blood is sent back into the body via the patient's right internal Jugular vein using a cannula. For example, a standard French percutaneous femoral arterial cannula can be used. The heated blood can go into the right side of the upper heart (the atrium) where it is pumped and dispersed through and into the body at a speed of approximately 4-7 liters per minute (or any of the flow rate ranges discussed above). In some embodiments, more than one vein (or one or more arteries, or both) can be used. In some embodiment, a different vein (or veins) may be used. In some embodiments, medications can be used to constrict veins and/or arteries to assist in keeping the heart beating consistently (e.g., using support system 103 of FIG. 1).

At step 216, in some embodiments, at least a portion of the heated blood is sent into the toxin removal system (e.g., a convection dialysis process implemented using toxin removal system 106 of FIG. 1). For example, a slip stream of blood (heated or not) is diverted from entering into the body into the toxin removal system. This can be done at a flow rate of, e.g., 0.2 to 4.5 liters per minute (e.g., 0.9 liters per minute) or any other flow rate (such as the flow rate ranges discussed above in connection with the toxin removal system 106 of FIG. 1). After having toxins removed, this blood can be sent back to join the portion of the blood that was not diverted into the toxin removal system, as illustrated in FIG. 1. As another example, all of the heated blood can be sent into the toxin removal system (e.g., using one or more pumps 104).

Toxins and pro inflammatory mediators can be removed in this step. Removed toxins can be sent to a waste collection site where they can be discarded. Plasma water containing the toxins can pass through a filter medium into the waste collection site. Downstream of the filter medium, removed plasma that is electrolyte- and acid-balanced may be put back into the system prior to entering the body. Either after the filtration or elsewhere in the path, one or more of the following may be added: bicarbonates, potassium, sodium, chloride, glucose, calcium, phosphorous, and magnesium. Other suitable things can be added.

The toxin removal system can use a 50,000 Dalton cut-off filter or larger. Fluid replacement can occur with a bicarb-based, electrolyte-balanced solution. This can help maintain a zero-balanced, convective toxin clearance therapy. Ultrafiltration rates (the amount of plasma water removed from the blood) can range between 2 liters and 10 liters per hour and blood flow rates in the toxin removal system can be maintained at about 1 liter per minute (or any of the flow rates discussed above in connection with the toxin removal system 106 of FIG. 1). As an example, 2 to 10 liters per hour of ultrafiltration can translate to between 25 and 110 mL per kilogram per hour. The toxin removal system can be continued after the circulation is complete via a dialysis catheter placed in the right internal jugular or femoral vein (or any other vein(s) or arter(ies)). In some embodiments, this can assist in maintaining homeostasis and remove inflammatory mediators and other toxins that result from cell death.

At step 218, in some embodiments, the heating unit can be turned off. This can occur after total body hyperthermia has been achieved and maintained for two hours or, e.g., up to six hours or more. In some embodiments, this can occur after total body hyperthermia has been achieved and maintained for a duration in any other range, such as 15 minutes to 2 hours, 15 minutes to 3 hours, 15 minutes to 4 hours, 15 minutes to 5 hours, 15 minutes to 7 hours, 1 hour to 2 hours, 1 hour to 3 hours, 1 hour to 4 hours, 1 hour to 5 hours, 1 hour to 6 hours, 2 hours to 3 hours, 2 hours to 4 hours, 2 hours to 5 hours, 2 hours to 6 hours, 3 hours to 4 hours, 3 hours to 5 hours, 3 hours to 6 hours, or any other range. The patient's temperature can be allowed to drift to normal temperature levels. The patient can then be separated from the path. The cannulas can then be removed and vascular repairs can be performed.

At step 220, in some embodiments, dialysis (convection and/or diffusion) and/or any other toxin removal procedure can be performed (e.g., using toxin removal system 106 of FIG. 1) for a period of time after the induced hyperthermia is completed. This can assist in removing toxins or dead tissue. In various embodiments, the period of time can range from 15 minutes to 48 hours after the induced hyperthermia is completed. In some embodiments, other periods of time may be used, such as 1 to 12 hours, 5 to 12 hours, 10 to 12 hours, 1 to 24 hours, 5 to 24 hours, 10 to 24 hours, 12 to 24 hours, 1 to 48 hours, 5 to 48 hours, 10 to 48 hours, 24 hours to 48 hours, 1 to 72 hours, 5 to 72 hours, 10 to 72 hours, 24 to 72 hours, 48 to 72 hours, or any other time period. This can promote safety for the patient and can facilitate complete or nearly complete removal of pro inflammatory mediators or toxins. In some embodiments, the toxin removal system uses a pressure gradient to force plasma water that contains the toxins and other undesirable inflammatory mediators through the filter medium and into a waste container, while simultaneously or nearly simultaneously, plasma water that is electrolyte- and acid-balanced, is returned to the blood. Before the blood re-enters the body, it may be treated with heat, oxygen, and venting to maintain suitable carbon dioxide levels. After the induced hyperthermia portion of the procedure is complete, the rate at which blood is removed and reintroduced to the body may be reduced to between 1 and 5 liters per minute. In some embodiments, the rate may be reduced to any other range of flow rates, such as 1 to 4 liters per minute, 1 to 3 liters per minute, 1 to 2 liters per minute, 2 to 5 liters per minute, 2 to 4 liters per minute, 2 to 3 liters per minute, or any other flow rate range. Fluids at approximately normal body temperatures (such as saline and water) may be given to the patient after the induced hyperthermia portion of the procedure has been completed. In some embodiments, fluid that is electrolyte- and acid-balanced (e.g., plasma water) can be added to the blood after the induced hyperthermia portion of the procedure has been completed; this fluid can be heated or preheated to a suitable temperature (e.g., 34, 35, 36, 37.5 degrees Celsius). This can, in some embodiments, reduce or prevent the chance of hypothermia.

Although this disclosure describes and illustrates particular steps of the method of FIG. 2 as occurring in a particular order, this disclosure contemplates any suitable steps of the method of FIG. 2 occurring in any suitable order. For example, the blood of the patient can be sent to the toxin removal system any time after it is removed from the patient (e.g., before it is heated, before it is oxygenated, before it is vented, etc.). As other example, the blood may be vented, heated, oxygenated, pumped, and/or sent for fluid replacement any time after the blood is removed from the patient. Some embodiments may repeat the steps of FIG. 2, where appropriate. For example, blood may be sent to toxin clearance more than once, vented more than once, heated more than once, oxygenated more than once, pumped more than once, and/or sent for fluid replacement more than once. Some embodiments may not include one or more of the steps of FIG. 2. For example, one or more of oxygenation, toxin clearance, venting, and/or fluid replacement may be optional. Furthermore, although this disclosure describes and illustrates particular components, devices, or systems carrying out particular steps of the method of FIG. 2, this disclosure contemplates any suitable combination of any suitable components, devices, or systems carrying out any suitable steps of any of the method of FIG. 2.

Figure 3:
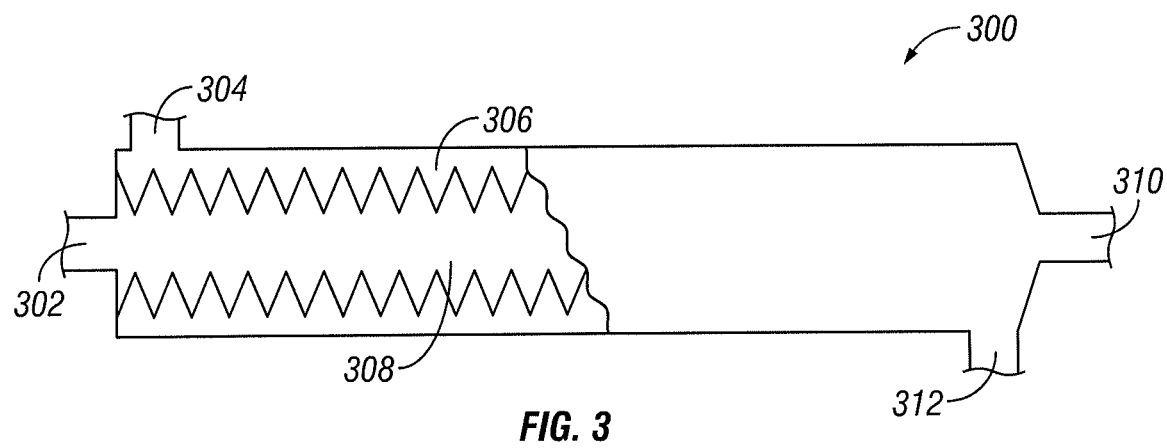
FIG. 3 illustrates one embodiment of a heat exchanger.

FIG. 3 illustrates one embodiment of heat exchanger 300. This is an example of an implementation of heat exchanger 110 of FIG. 1. Heat exchanger 300 comprises port 302 for blood to enter heat exchanger 300 and port 304 for the heated fluid (which can, e.g., come from a reservoir of 1-200 gallons in size). Heat exchanger 300 also includes external chamber 306 for holding the heated fluid and internal chamber 308 for holding the blood. As blood passes through internal chamber 308 it is heated through the heat radiating from external chamber 306. Chambers 306 and 308 prevent the blood from coming into physical contact with the heated fluid. Port 310 is where blood exits heat exchanger 300 and port 312 is where the heated fluid exits heat exchanger 300. The heated fluid can be any suitable liquid or gas and can be pumped through heat exchanger 300 at any suitable rate (e.g., at or above: 1 liter per minute, 5 liters per minute, 10 liters per minute, 0.5 gallons per minute, 1 gallon per minute, 5 gallons per minute, 10 gallons per minute, 15 gallons per minute, 30 gallons per minute, 50 gallons per minute, 100 gallons per minute, 150 gallons per minute, 200 gallons per minute, and/or 250 gallons per minute. Furthermore, the surface of external chamber 306 may include any type of surface (e.g., a smooth wall) instead of (or in addition) to the jagged structure illustrated in FIG. 3. An irregular structure like the one illustrated may promote more efficient heating.

Heat exchanger 300, as discussed above, may be controlled to maintain the temperature of the water or gas circulating through external chamber 306 within a temperature range (such as any of the temperature ranges discussed above for heating the blood). One or more temperature sensors may be present within a fluid bath or other chamber for heating the water, fluid, or gas that flows through external chamber 306. One or more temperature sensors may also be within internal chamber 308, on the outside of external chamber 306, or anywhere that the temperature correlates to or measures the temperature of the fluid or gas circulating through external chamber 306, the temperature within the heating chamber or fluid bath, or the temperature of the blood circulating through the heater. In addition, one or more of the temperature sensors 118a-l, as discussed above, could be used to control the temperature of the heat source 112. Based upon the feedback from one or more temperature sensors, heat source 112 can be controlled to become hotter or colder so as to maintain the blood within the desired temperature range or at the desired temperature.

Figure 4:
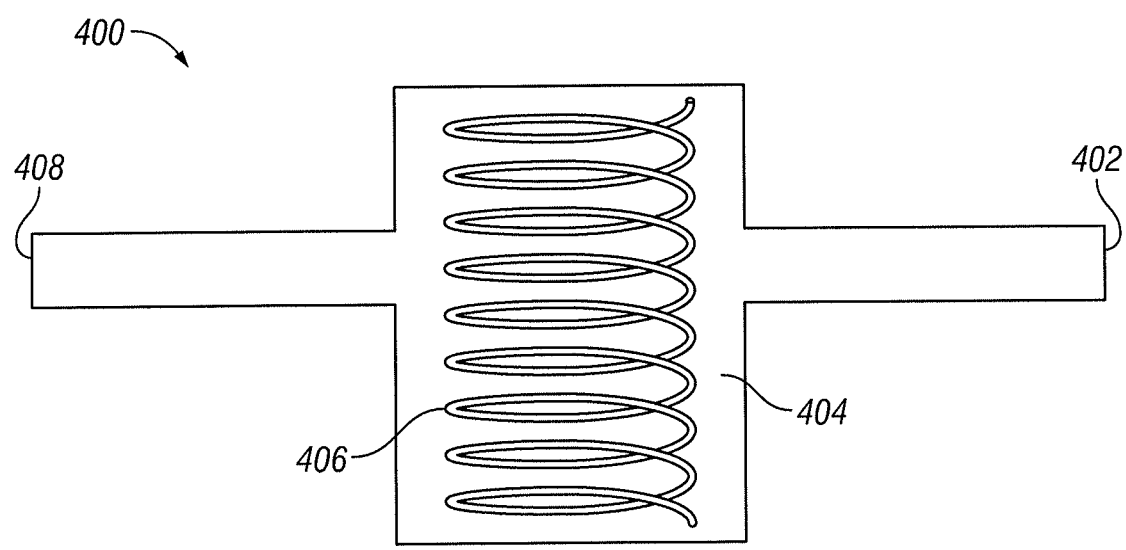
FIG. 4 illustrates one embodiment of an electrical heat exchanger.

FIG. 4 illustrates one embodiment of an electrical heat exchanger 400. This is an example of an implementation of heat exchanger 110 of FIG. 1. Heat exchanger 400 comprises port 402 for blood to enter heat exchanger 400. Heat exchanger 400 includes chamber 404 that also includes heating element 406. Blood passes through chamber 404 and it is heated using heating element 406. Port 408 is where blood exits heat exchanger 400. Like the embodiment in FIG. 3, one or more temperature sensors can be used to control the temperature of the blood by controlling heating element 406. In addition to sensors 118a-l, as discussed above, one or more temperature sensors could be placed in the inlet to chamber 404, the outlet to chamber 404, downstream from the outlet, or at one or more places within chamber 404.

Figure 5:
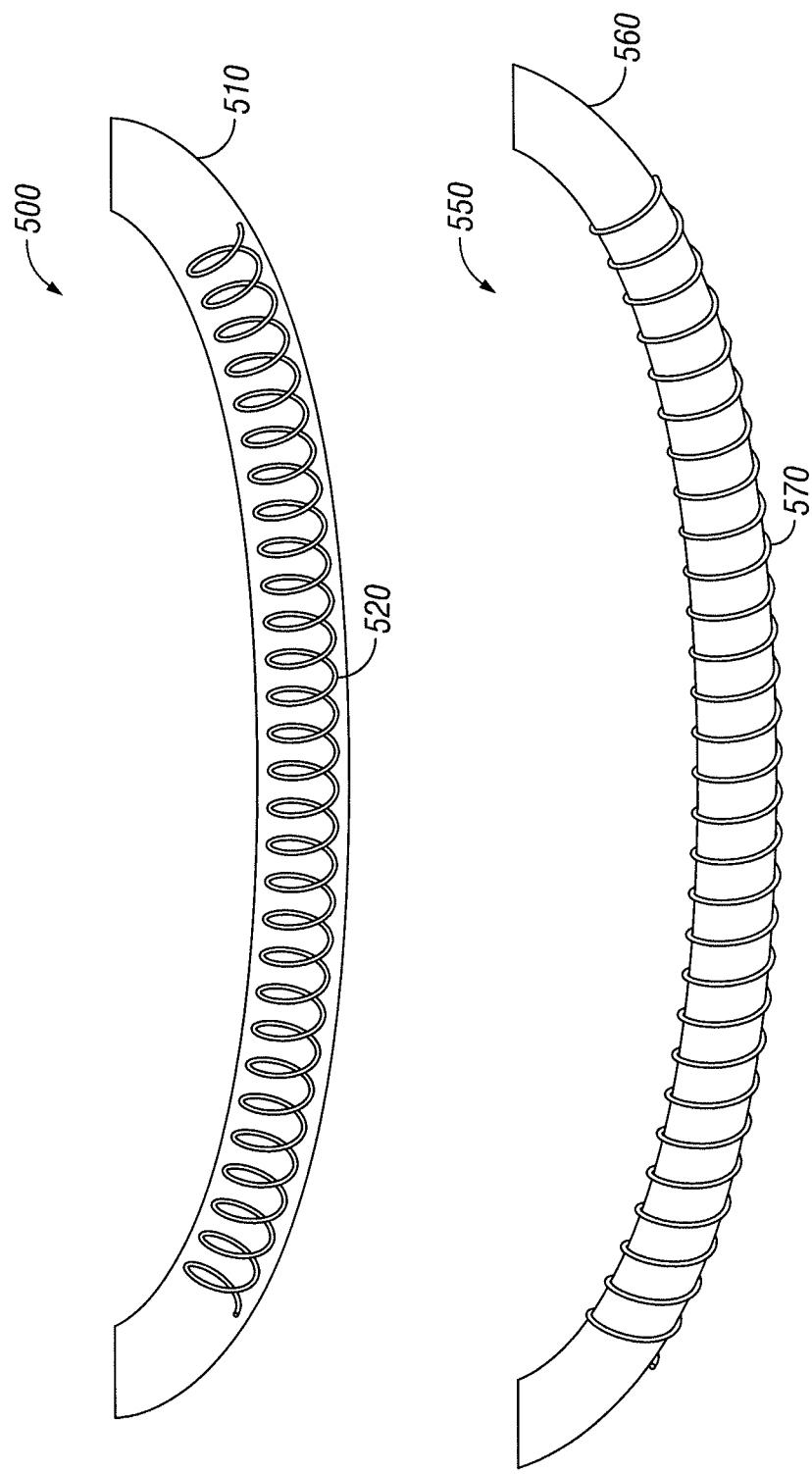
FIG. 5 illustrates two embodiments of a manner of heating blood while it is in the path.

FIG. 5 illustrates two embodiments of a manner of heating blood while it is in the path of system 100 of FIG. 1. These could be used in conjunction with or instead of heat exchanger 110. Where other components such as pump 104, venting system 108, oxygenator 114, toxin removal system 106 or reintroduction system 116 have the ability to heat the blood to the desired temperature range or the desired temperature, both heat exchanger 110 and the heating system 500 could be omitted, or could be used in conjunction with other heating means. Internal heating system 500 uses electrical heating element 520 within tube 510 which carries the patient's blood. Tube 510 is configured to prevent the blood from directly physically contacting electrical heating element 520. External heating system 550 uses electrical heating element 570 around tube 560 to heat blood carried in tube 560. Either or both of heating systems 500 and 550 can be used in conjunction with heat exchanger 110 or instead of heat exchanger 110 of FIG. 1. The greater the surface area of the heating element(s) exposed to the blood, the faster the blood will increase to the desired temperature. Internal heating system 500 and external heating system 550 may be controlled in any manner known in the medical field. As an example, internal heating system 500 and external heating system 550 may be controlled using the heat control system discussed above (and/or heating probes 118a-l discussed above). The heat control system may control internal heating system 500 and external heating system 550 simultaneously (e.g., they both may be controlled to increase or decrease their temperature together) or individually (e.g., internal heating system 500 may remain at the same temperature while external heating system 550 is turned off).

Figure 6:
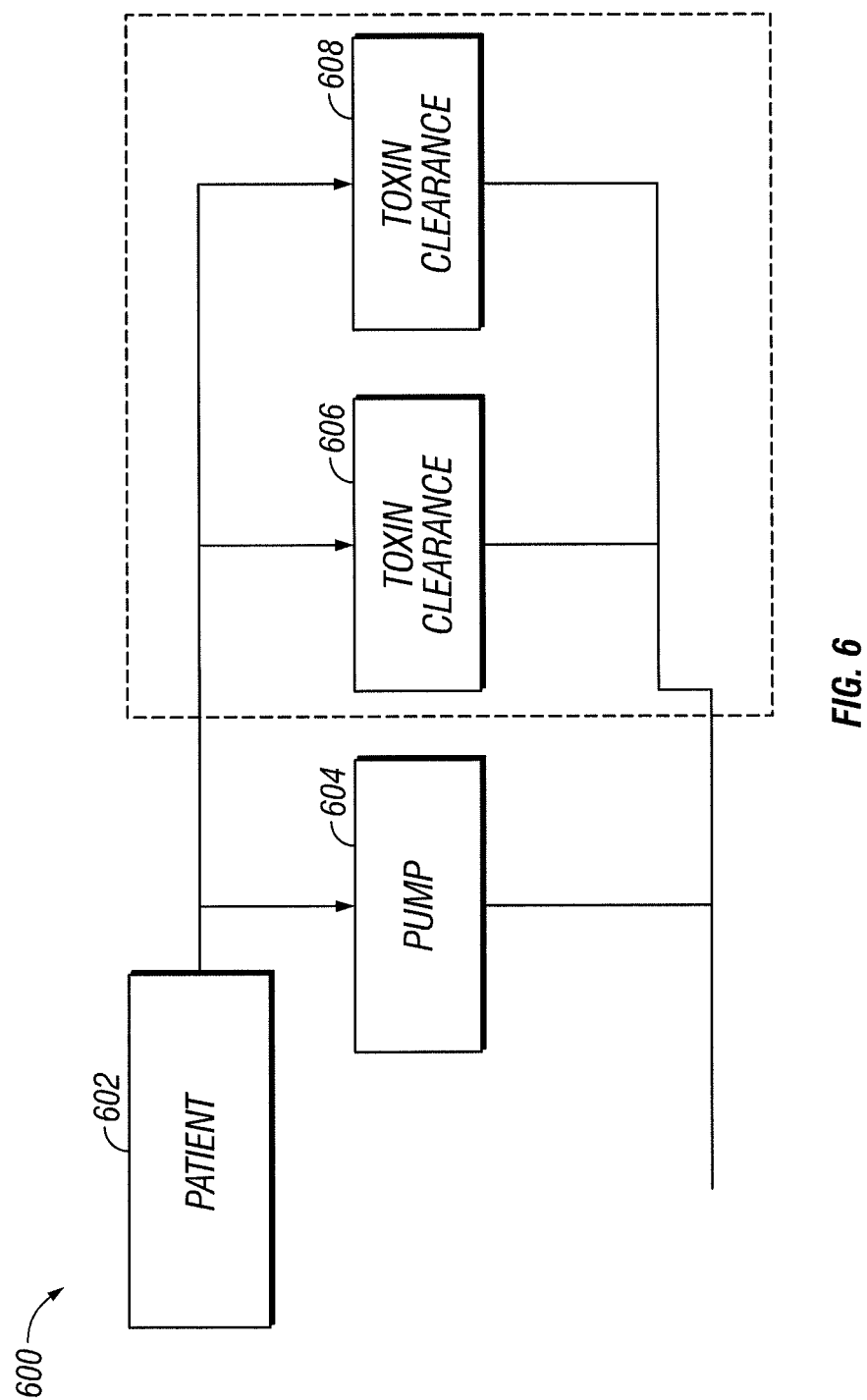
FIG. 6 illustrates one embodiment of a system for inducing hyperthermia with multiple toxin removal systems.

FIG. 6 illustrates one embodiment of system 600 that can be an alternative configuration of system 100 of FIG. 1 with multiple toxin removal systems 606 and 608. Toxin removal systems 606 and 608 can be implemented as modules, such as dialysis modules. Each module can be implemented using any of the techniques discussed above with respect to toxin removal system 106 of FIG. 1. For example, each dialysis module can be implemented as a dialysis (convection or diffusion) machine. Blood from patient 602 is divided between pump 604 and toxin removal systems 606 and 608 (e.g., implemented using convection dialysis systems). The blood after passing through toxin removal systems 606 and 608 is combined with the blood passing through pump 604. This combined blood stream then is heated and treated according to the path depicted in FIG. 1 and discussed above. In some embodiments, there can be more than two toxin removal systems. Having more than one toxin removal system can be beneficial in various embodiments. For example, it can allow for a faster rate of blood filtration. This can lead to faster recuperation times for patient 602. It may also be beneficial to provide redundancy in the event of a failure of one of the toxin removal systems during a procedure. While two toxin removal systems are depicted in FIG. 6, any suitable number of toxin removal systems can be used (e.g., 2, 3, 4, 5, 6, 7, or 8 toxin removal systems) and connected in parallel in a manner similar to how toxin removal systems 606 and 608 are connected. In some embodiments, the number of toxin removal systems that can be connected can be determined using a desired rate of treatment of the blood. For example, should it be desired to treat the blood at a higher rate, more toxin removal systems can be added. The multiple toxin removal systems can be of the same type or different types (e.g., using convection or diffusion dialysis techniques). The rates of treating the blood that can be achieved by using multiple toxin removal systems can be in the range of, e.g., 0.9-2.5 liters per minute.

Figure 7:
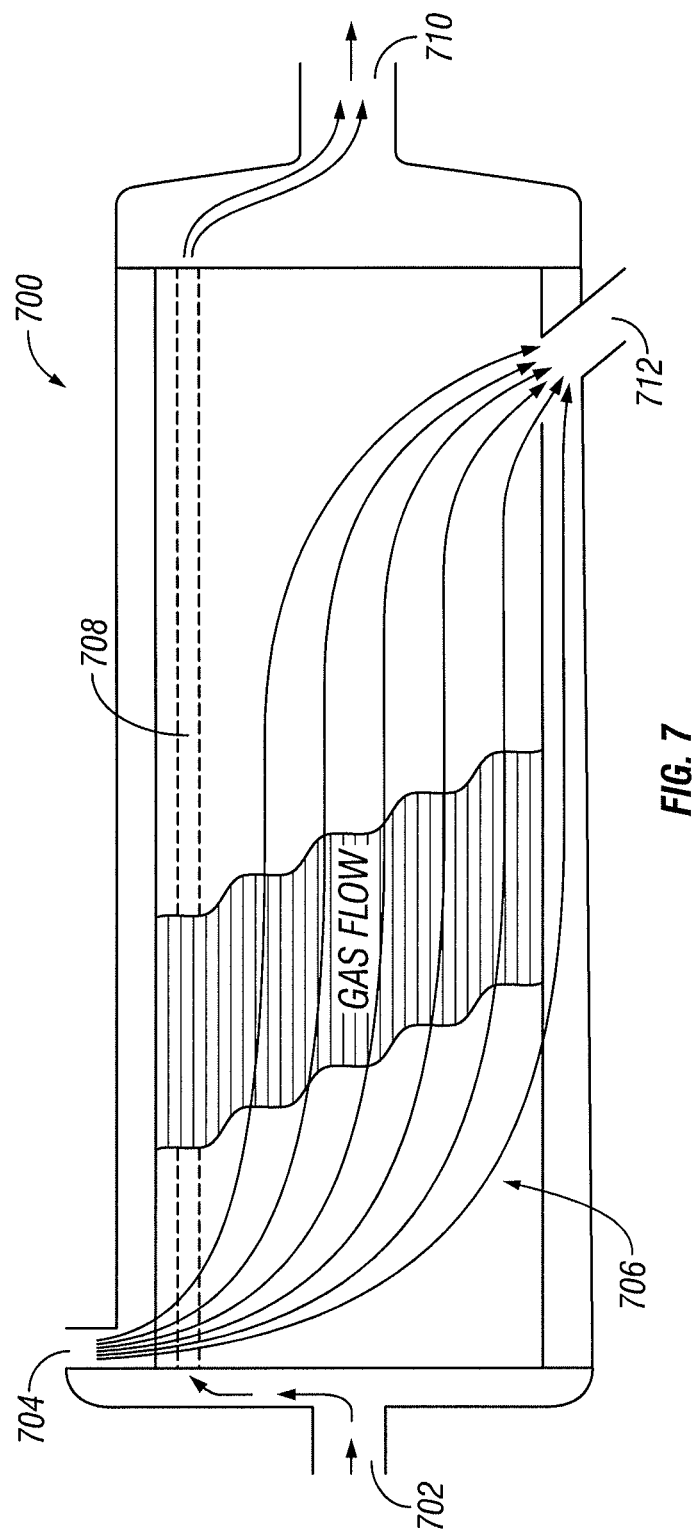
FIG. 7 illustrates one embodiment of a venting system.

FIG. 7 illustrates one embodiment of system 700 that can be used to implement venting system 108 of FIG. 1. System 700 includes port 702 through which blood enters system 700 and port 704 through which gas enters system 700. Blood flow 708 goes through system 700 and exits through port 710. Gas flows into system 700 through port 704 and exits through port 712. A fan driving a gas into a conduit or a conduit connected to a compressed gas tank could be coupled to port 704 to introduce the gas to port 704. Outlet 712 can vent to the atmosphere or to a system to dispose of gases. Membrane 706 separates the flow of gas from blood flow 708. Membrane 706 can be a hollow fiber membrane and blood flow 708 goes through the center of membrane 706 while gas flows in a direction counter to the blood flow. Alternatively, the gas can flow through the inside of membrane 706 and blood flow 708 can occur on the outside of membrane 706 in a direction counter to the gas flow. Membrane 706 can be implemented using flat membranes or extended surface area membranes that have been pleated or have otherwise used a method to utilize more membrane material in the filter element (e.g., folding). System 700 facilitates carbon dioxide to be vented from blood stream 708 through membrane 706 and to exit port 712 using cross-flow microfiltration. Any suitable gas can be used such as nitrogen, oxygen, or air from the room in which the patient is located. Oxygen may be preferable to use as it can void removing oxygen from the blood in some embodiments. In some embodiments, membrane 706 may be a material that absorbs carbon dioxide from the blood; for example, the material can exhibit adsorption such that the carbon dioxide is adsorbed onto a chemical surface of membrane 706 due to a pressure gradient on the surface of the chemical. System 700 can be included in-line with the path of system 100 of FIG. 1 or as a branch off of the path.

In some embodiments, venting system 108 may have a heater within the structure illustrated in FIG. 7, such as at the inlet or outlet or in a separate chamber (not explicitly shown) located prior to the inlet or after the outlet. Such a heater could be used to heat or aid in heating the blood to a temperature within any of the temperature ranges set forth above.

In some embodiments, venting the carbon dioxide from the blood may include lowering and/or maintaining the amount of carbon dioxide in the patient (and/or in the blood) to a measurement in the range of 35 to 60 Millimeters of Mercury (mmHg), and preferably to 35 to 45 mmHg. In some embodiments, venting the carbon dioxide from the blood may include lowering and/or maintaining the amount of carbon dioxide in the patient (and/or in the blood) to other suitable ranges, such as 35 to 100 mmHg, 40 to 100 mmHg, 45 to 100 mmHg, 50 to 100 mmHg, 55 to 100 mmHg, 60 to 100 mmHg, 65 to 100 mmHg, 70 to 100 mmHg, 75 to 100 mmHg, 80 to 100 mmHg, 85 to 100 mmHg, 90 to 100 mmHg, 95 to 100 mmHg, 35 to 95 mmHg, 35 to 90 mmHg, 35 to 85 mmHg, 35 to 80 mmHg, 35 to 75 mmHg, 35 to 70 mmHg, 35 to 65 mmHg, 35 to 55 mmHg, 35 to 50 mmHg, 40 to 60 mmHg, 45 to 60 mmHg, 50 to 60 mmHg, 55 to 60 mmHg, or any other range between 35 to 100 mmHg. In some embodiments, venting the carbon dioxide from the blood may include lowering and/or maintaining the amount of carbon dioxide in the patient (and/or in the blood) to any measurement below 150 mmHg, any measurement below 140 mmHg, any measurement below 130 mmHg, any measurement below 120 mmHg, any measurement below 110 mmHg, any measurement below 100 mmHg, any measurement below 95 mmHg, any measurement below 90 mmHg, any measurement below 85 mmHg, any measurement below 80 mmHg, any measurement below 75 mmHg, any measurement below 70 mmHg, any measurement below 65 mmHg, any measurement below 60 mmHg, any measurement below 55 mmHg, any measurement below 50 mmHg, any measurement below 45 mmHg, or any measurement below 40 mmHg.

In some embodiments, a measurement of the amount of carbon dioxide in the patient (and/or in the blood) may be taken in any suitable manner known in the medical field. As an example, the measurement may be taken based on air breathed out or expelled by the patient into equipment configured to measure carbon dioxide. Blood analyzers can also be used, such as those provided by SIEMENS or ABBOTT.

Figure 8:
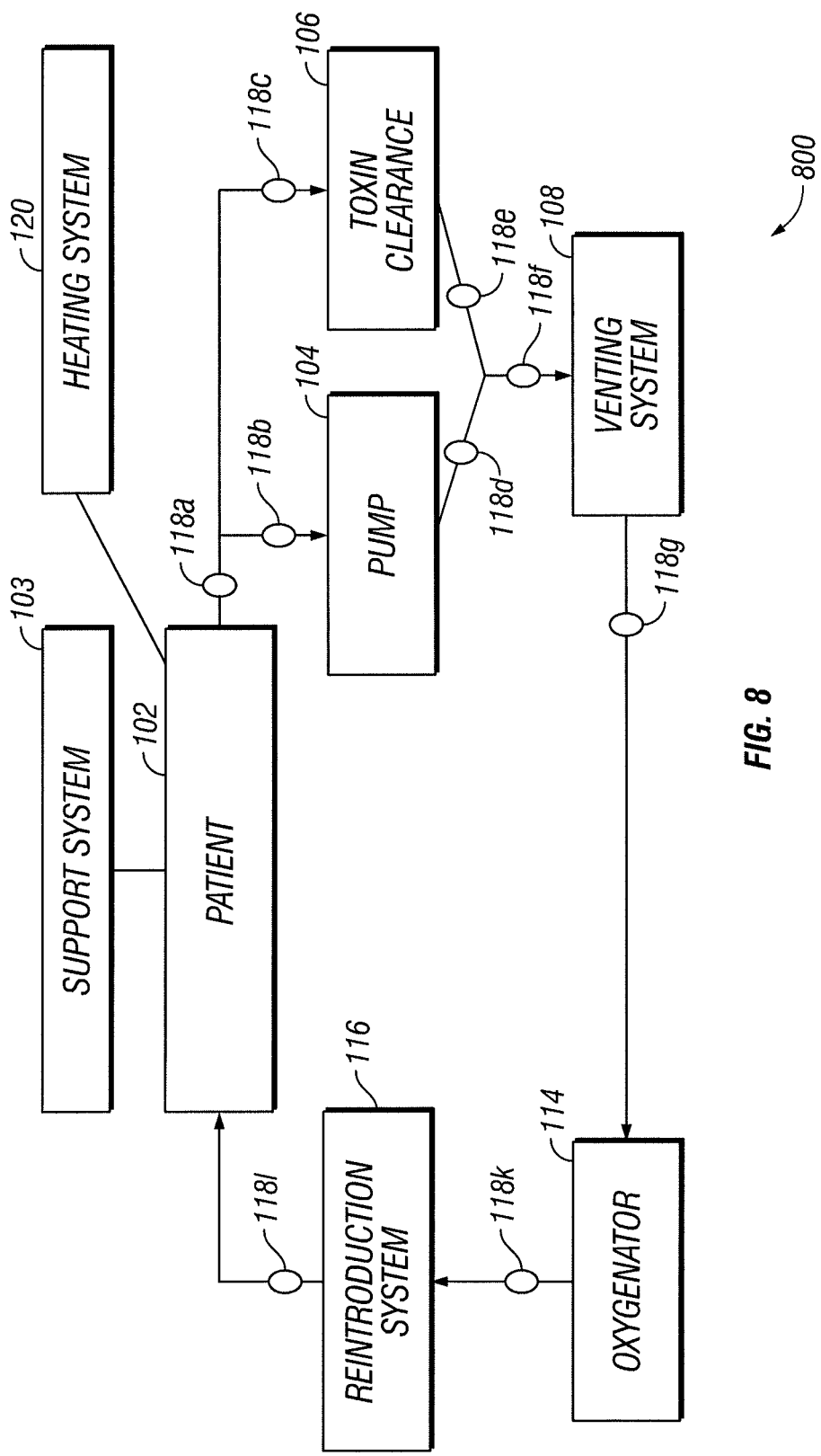
FIG. 8 illustrates one embodiment of a system configured to induce hyperthermia without heating the blood in a path.

FIG. 8 illustrates one embodiment of system 800 configured to induce hyperthermia in patient 102 without heating the blood in a path outside of the body, or possibly in conjunction with a path having any of the options discussed above. System 800 has similar components as system 100 of FIG. 1 except for the potential absence of heat exchanger 110 and heat source 112 in the path. In system 800, patient 102 is connected to heating system 120 as will be further discussed. In system 800, blood flows from patient 102 through pump 104 and toxin removal system 106. It then passes through venting system 108 which can facilitate removal of carbon dioxide from the blood. The blood then goes through oxygenator 114 and reintroduction system 116 before reentering patient 102.

Heating system 120 provides heat external to patient 102 in order to raise the temperature of patient 102. There are various manners in which this is accomplished and examples of such shall now be discussed. In some embodiments, heating system 120 can be used to treat a patient that is fully, or partially, submerged in water that is at a temperature of, e.g., 42.9 degrees Celsius (or at any of the temperature ranges or temperatures discussed above). As examples, the patient can be submerged in the water naked, in a thin plastic suit (or other suitable material such as semi-flexible steel, clay, or other conforming sheet), with their head submerged, protected, or not protected by a material to prevent water from entering into the body (e.g., via the mouth and nose). As another example, the full body can be in a tub or on a table with reinforced sides capable of holding water and the patient fully submerged in the water. Patient 102 can be connected to support system 103 which can provide a ventilator, a monitoring system, an intravenous system, and other suitable systems to support the health of the patient while being partially or fully submerged during the induced hyperthermia procedure applied using system 800.

Using heating system 120, the water (or other suitable fluid) can be warmed quickly to, e.g., 43.2 degrees Celsius; the water (or other suitable fluid) can be heated to between 42-45 degrees Celsius (or to any of the temperature ranges or temperatures discussed above to which the body or blood can be heated) in some embodiments. The water can be circulated and this can, in some embodiments, facilitate even heat distribution to the entire body, including the head. Other suitable fluids other than water can be used, such as other liquids or gases. Another suitable alternative is submerging the patient into a heated set of solid particles (e.g., sand, iron filings, gold powder, and mud). As the liquid or gas is flowed faster by heating system 120, the speed and efficiency of raising the core temperature of patient 102 is improved. Further, using a denser liquid can improve the speed and efficiency of heating the core temperature of patient 102 in various embodiments. As another example, heating system 120 can use an electric heating coil wrapped around patient 102 (using suitable forms of protection) to apply heat to patient 102.

In some embodiments, the patient may be placed in a suit, bag, or tarp (or other suitable enclosure) that circulates a hot fluid (e.g., between 41.8-45 degrees Celsius, or any of the temperature ranges or temperatures discussed above to which the body or blood can be heated) across it using heating system 120; this can be used in addition to or as an alternative to submerging the patient in a hot medium. Heat transfer can be improved by using denser materials for the suit or denser fluids for circulating within the suit.

In some embodiments, bags may be introduced into the stomach and through the rectum that circulate heated fluids (e.g., fluids heated to between 42 and 43 degrees Celsius, or to any of the temperature ranges or temperatures discussed above to which the body or blood can be heated) using heating system 120. In some embodiments, the various temperature measuring techniques disclosed above can be utilized to maintain the water (or other liquid) to a precise temperature (using heating system 120) and to monitor the body temperature precisely during the procedure. One or more dialysis techniques (or other toxin removal techniques) disclosed herein (or known in the medical field) can be applied to the patient via veins or arteries during the procedure or extended after the procedure if required (e.g., using toxin removal system 106). This, in some embodiments, can be due to the amount of toxins created by the body during the procedure.

In some embodiments, a patient undergoing treatment using system 100 or 800 can be wrapped or covered with a heat-reflecting material. For example, aluminum foil or tin foil can be wrapped or placed on a patient to retain heat prior to putting on heating blanket. Heat radiating from the patient can thus be reflected back to promote heat retention. A blanket with circulating heating water can be used. The water can be heated to between 42 and 43.2 degrees Celsius (or to any of the temperature ranges or temperatures discussed above). The water can be heated using heating system 120. The water temperature can be varied in suitable manners.

For example, a patient may be wrapped in a sweat-absorbing covering (e.g., a sterile blanket). Both above and beneath the patient, one or more heated blankets (such as water heated blankets) can be placed around the patient. Heat reflecting material can be placed around the one or more heated blankets (e.g., sterile towels or other suitable material that reflect heat). An enclosure can be placed over the patient that comprises heat reflective or insulative material (e.g., Styrofoam). The enclosure can include flaps that would go underneath the patient or underneath the object supporting the patient (e.g., a platform, bed, or table); the flaps can connect together and form a type of chamber. Warm air or other suitable gas can be introduced into the chamber.

Using one or more of the techniques discussed above, the body (either the entire body, substantially the entire body, a majority of the body, or the core of the body) can be heated to a temperature of at least 42.0, 42.1, 42.2, 42.3, 42.4, 42.5, 42.6, 42.7, 42.8, 42.9, 43.0, 43.1, 43.2, 43.3, 43.4, 43.5, 43.6, 43.7, 43.8, or 43.9 degrees Celsius (or to any of the temperature ranges or temperatures discussed above) and maintained there (within a suitable temperature range) either continuously or intermittently for a period of 15 minutes or for a period of up to 6 hours. In some embodiments, the body can be maintained at any of the temperature ranges or temperatures discussed above or for any other range of time, such as 15 minutes to 2 hours, 15 minutes to 3 hours, 15 minutes to 4 hours, 15 minutes to 5 hours, 15 minutes to 7 hours, 1 hour to 2 hours, 1 hour to 3 hours, 1 hour to 4 hours, 1 hour to 5 hours, 1 hour to 6 hours, 2 hours to 3 hours, 2 hours to 4 hours, 2 hours to 5 hours, 2 hours to 6 hours, 3 hours to 4 hours, 3 hours to 5 hours, 3 hours to 6 hours, or any other range. The techniques discussed above, alone or in combination with each other and other techniques, may facilitate raising the core temperature of the patient faster than without using such techniques (e.g., the patient's core body temperature may be raised to between 42 and 43 degrees Celsius five to ten minutes faster or greater). The techniques discussed above with respect to system 800 can be used in combination with the techniques of system 100 of FIG. 1. For example, patient 102 may have its blood heated in a path (as depicted in FIG. 1) while also being submersed in a heated liquid (as discussed above with respect to FIG. 8). Some or all of the techniques discussed with respect to system 800 can be used, in various embodiments, with system 100 of FIG. 1.

Figure 9:
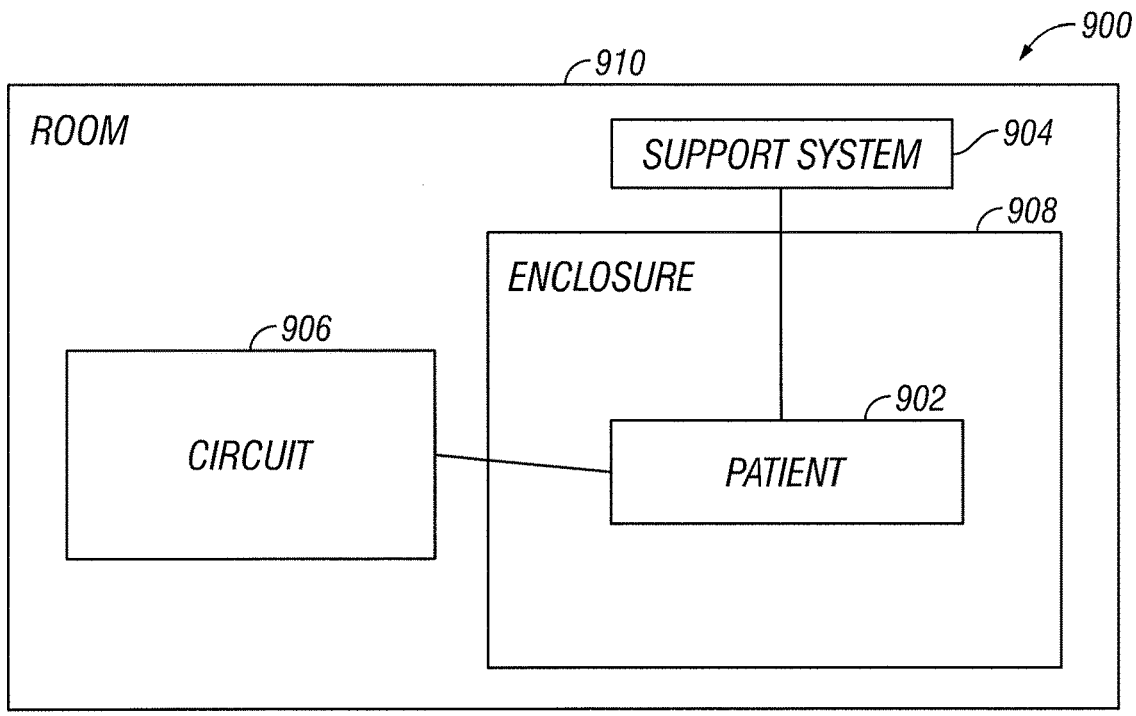
FIG. 9 illustrates one embodiment of inducing hyperthermia where the patient is in an enclosure that is heated.

FIG. 9 illustrates one embodiment of inducing hyperthermia where patient 902 is in enclosure 908 that is heated. For clarity, room 910 is illustrated in which the induced hyperthermia takes place. Blood from patient 902 is sent to path 906 where it can be heated and/or treated as discussed above; path 906 can include one or more of the components of the path in system 100 of FIG. 1 and, in various embodiments, may be in enclosure 908. Patient 902 is connected to support system 904; support system 904 can operate in the same manner as support system 103 of FIG. 1 and, in various embodiments, may be in enclosure 908. Enclosure 908 can be a room inside of room 910 or an enclosure within room 910. Enclosure 908 can be kept to a temperature up to, e.g., 43.2 degrees Celsius (or any of the temperature ranges or temperatures discussed above). As an example, enclosure 908 can be kept at a temperature of between 77 degrees and 110 degrees Fahrenheit (e.g., a temperature of approximately 108.5 degrees Fahrenheit). This high temperature of enclosure 908 can be maintained during the induced hyperthermia procedure and brought down during a cool down period (e.g., after the patient has been at a temperature of approximately 42.5 degrees Celsius for a period of approximately 2 hours, or after the patient has been at any of the temperature ranges or temperatures discussed above for any of the time ranges discussed above). At that point, enclosure 908 can be removed or (e.g., when enclosure 908 is a room) will be cooled down to a temperature of 77 degrees Fahrenheit for the cool down period of, e.g., approximately 20 to 30 minutes. The patient's body temperature can then go back to a normal or stable temperature (e.g., 98.6 degrees Fahrenheit). The temperature of room 910 can be different than enclosure 908; room 910 can include those assisting with the procedure and the different temperature can be beneficial (e.g., for the comfort of those assisting with the procedure).

In some embodiments, system 900 can provide one or more benefits to inducing hyperthermia such as: providing the ability to heat the patient's body faster by, e.g., reducing heat loss; and/or maintain the skin of the patient at a desired temperature so as to completely keep the entire body (or substantially all of the entire body) at or near a desired temperature (e.g., 42.5 degrees Celsius, or any of the temperature ranges or temperatures discussed above) including the skin. This can help treat various maladies, e.g., skin cancer. Use of such a room or enclosure can facilitate temperature sensing during treatment of the patient. For example, infrared cameras used to detect temperature can have better accuracy of the body's entire temperature and or the brain temperature when using such a room or enclosure. The techniques of system 900 can be used in system 100 of FIG. 1 (i.e., a system that heats the blood of a patient in a path) and/or in system 800 of FIG. 8 (i.e., a system that heats the blood within the body of the patient).

Figure 10:
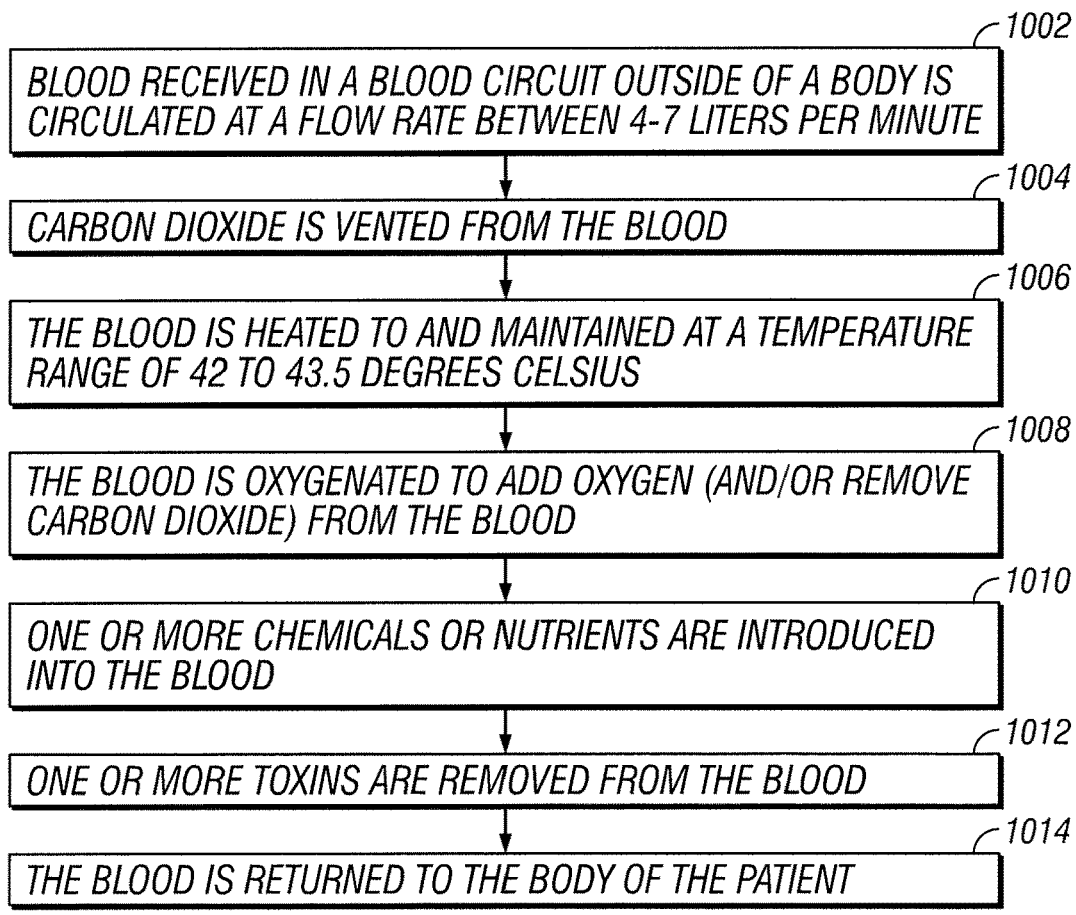
FIG. 10 illustrates one embodiment of a method for treating blood outside of a body.

FIG. 10 illustrates one embodiment of a method for treating blood outside of a body. In some embodiments, one or more steps of method 1000 may be performed using one or more components of FIG. 1.

At step 1002, blood received in a blood path outside of a body is circulated at a flow rate between 4-7 liters per minute. The blood may be received from a body or from a stored source of blood. For example, the blood may be circulated at a flow rate between 4.1 and 7 liters per minute, between 4.2 and 7 liters per minute, between 4.3 and 7 liters per minute, between 4.4 and 7 liters per minute, between 4.5 and 7 liters per minute, between 4.6 and 7 liters per minute, between 4.7 and 7 liters per minute, between 4.8 and 7 liters per minute, between 4.9 and 7 liters per minute, between 5 and 7 liters per minute, between 5.1 and 7 liters per minute, between 5.5 and 7 liters per minute, between 6 and 7 liters per minute, between 6.5 and 7 liters per minute, between 5 and 6.5 liters per minute, between 5 and 6 liters per minute, between 5 and 5.5 liters per minute, or any other range between 4-7 liters per minute. In addition, any of the flow rates discussed above can be used. In some embodiments, one or more pumps (such as pump 104 of FIG. 1) may be used to circulate the blood at the flow rate. Furthermore, the blood may be received in the path as a result of being removed from a patient during a medical procedure, such as a medical procedure for treating various maladies, such as various types of cancer, bacterial infections, viral infections, meningitis, gangrene, Ebola, Hepatitis C, AIDS, staph infections, and pneumonia (viral or bacterial).

At step 1004, carbon dioxide, carbon monoxide, and/or other harmful or undesirable gases are vented from the blood. In some embodiments, one or more venting systems (such as venting system 109 of FIG. 1) may be used to vent undesirable gases from the blood. Venting the undesirable gases from the blood may be advantageous in various embodiments. For example, as a result of a medical procedure, the blood may have a buildup of carbon dioxide in the blood. Removing the carbon dioxide from the blood before the blood is returned to the patient can prevent or reduce the likelihood of a cardiac arrhythmia, a heart failure, or other health failure of patient 102.

At step 1006, the blood may be heated to and maintained at a suitable temperature. For example, the blood may be heated to and maintained at a range of 42 to 43.9 degrees Celsius, a range of 42.1 to 43.9 degrees Celsius, a range of 42.2 to 43.9 degrees Celsius, a range of 42.3 to 43.9 degrees Celsius, a range of 42.4 to 43.9 degrees Celsius, a range of 42.5 to 43.9 degrees Celsius, a range of 42.6 to 43.9 degrees Celsius, a range of 42.7 to 43.9 degrees Celsius, a range of 42.8 to 43.9 degrees Celsius, a range of 42.9 to 43.9 degrees Celsius, a range of 43.0 to 43.9 degrees Celsius, a range of 43.1 to 43.9 degrees Celsius, a range of 43.2 to 43.9 degrees Celsius, a range of 43.3 to 43.9 degrees Celsius, a range of 43.4 to 43.9 degrees Celsius, a range of 43.5 to 43.9 degrees Celsius, a range of 43.6 to 43.9 degrees Celsius, a range of 43.7 to 43.9 degrees Celsius, a range of 43.8 to 43.9 degrees Celsius, a range of 42 to 43.8 degrees Celsius, a range of 42 to 43.7 degrees Celsius, a range of 42 to 43.6 degrees Celsius, a range of 42 to 43.5 degrees Celsius, a range of 42 to 43.4 degrees Celsius, a range of 42 to 43.3 degrees Celsius, a range of 42 to 43.2 degrees Celsius, a range of 42 to 43.1 degrees Celsius, a range of 42 to 43.0 degrees Celsius, a range of 42 to 42.8 degrees Celsius, a range of 42 to 42.7 degrees Celsius, a range of 42 to 42.6 degrees Celsius, a range of 42 to 42.5 degrees Celsius, a range of 42 to 42.4 degrees Celsius, a range of 42 to 42.3 degrees Celsius, a range of 42 to 42.2 degrees Celsius, a range of 42 to 42.1 degrees Celsius, a range of 42.1 to 42.8 degrees Celsius, a range of 42.3 to 42.7 degrees Celsius, a range of 42.4 to 42.6 degrees Celsius, a range of 42.5 to 42.9 degrees Celsius, a range of 42.6 to 42.9 degrees Celsius, a range of 42.7 to 42.9 degrees Celsius, a range of 42.8 to 42.9 degrees Celsius, a range of 42.5 to 42.8 degrees Celsius, a range of 42.5 to 42.7 degrees Celsius, a range of 42.5 to 42.6 degrees Celsius, or any other range between 42 and 43.9 degrees Celsius such as the ranges set forth above in connection with FIG. 1. As another example, the blood may be heated to and maintained at a temperature not above 43.9 degrees Celsius, a temperature not above 43.8 degrees Celsius, a temperature not above 43.7 degrees Celsius, a temperature not above 43.6 degrees Celsius, a temperature not above 43.5 degrees Celsius, a temperature not above 43.4 degrees Celsius, a temperature not above 43.2 degrees Celsius, a temperature not above 43.1 degrees Celsius, a temperature not above 43.0 degrees Celsius, a temperature not above 42.9 degrees Celsius, a temperature not above 42.8 degrees Celsius, a temperature not above 42.7 degrees Celsius, a temperature not above 42.6 degrees Celsius, a temperature not above 42.5 degrees Celsius, a temperature not above 42.4 degrees Celsius, or a temperature not above 42.3 degrees Celsius, or any other temperature described above. One or more heat exchangers and/or heating devices (such as heat exchanger 110 of FIG. 1 and/or heating tubes of FIG. 1) may be used to heat the blood to (and maintain the blood at) the temperature or temperature range suitable for the medical procedure.

At step 1008, the blood may be oxygenated to add oxygen (and/or remove carbon dioxide) from the blood. One or more oxygenators (such as oxygenator 114 of FIG. 1) may be used to oxygenate the blood.

At step 1010, one or more substances, chemicals, or nutrients may be introduced into the blood. As an example, suitable pharmaceuticals, vitamins, and/or nutritional elements (e.g., liquid food and/or glucose) may be introduced into the blood. As another example, one or more substances can be introduced that facilitate or increase the production of reactive oxygen species within the blood (e.g., ozone or Freon as discussed above). Administration of such pharmaceuticals, vitamins, and/or nutritional elements may assist healthy cells and/or may facilitate killing of unhealthy cells (e.g., cancer cells or other cells deleterious to the body). One or more reintroduction systems (such as reintroduction system 116 of FIG. 1) may be used to add the one or more chemicals or nutrients into the blood.

At step 1012, one or more toxins may be removed from the blood. For example, pro inflammatory mediators like Interlukin and Cytokine may be removed from the blood. In some embodiments, one or more toxin removal systems (such as toxin removal system 106 of FIG. 1) may be used to remove toxins from the blood. Removing toxins from the blood may be advantageous in various embodiments as it may make the blood more suitable to be injected into a human. In some embodiments, the toxins may be removed using diffusion dialysis and/or convection dialysis. Furthermore, in some embodiments, toxins may be removed from all or a portion of the blood. As an example, all of the blood may be provided to the toxin removal system via one or more pumps. As a further example, a slip stream of the blood may be diverted to the toxin removal system.

At step 1014, the blood may be returned to the body of the patient. It may also be stored for later use. The treated blood (e.g., having the above described temperature ranges or temperature, flowing at the above described flow rate, and/or having been treated using one or more of the above techniques or steps) may be inserted into the patient's body. Such an insertion of this treated blood may be advantageous because it may allow the patient to be treated for various maladies, such as various types of cancer (including Stage IV cancer), bacterial infections, viral infections, meningitis, Hepatitis C, AIDS, staph infections, and pneumonia (viral or bacterial), as is described above in FIG. 1.

Although this disclosure describes and illustrates particular steps of the method of FIG. 10 as occurring in a particular order, this disclosure contemplates any suitable steps of the method of FIG. 10 occurring in any suitable order. For example, the blood can be sent to the toxin removal system any time after it is removed from the patient or received from another source (e.g., before it is heated, before it is oxygenated, before it is vented, etc.). As other example, the blood may be vented, heated, oxygenated, pumped, and/or sent for fluid replacement any time after the blood is removed from the patient or received from another source. Some embodiments may repeat the steps of FIG. 10, where appropriate. For example, blood may be sent to toxin clearance more than once, vented more than once, heated more than once, oxygenated more than once, pumped more than once, and/or sent for fluid replacement more than once. Some embodiments may not include one or more of the steps of FIG. 10. For example, one or more of oxygenation, toxin clearance, venting, and/or fluid replacement may be optional. Furthermore, although this disclosure describes and illustrates particular components, devices, or systems carrying out particular steps of the method of FIG. 10, this disclosure contemplates any suitable combination of any suitable components, devices, or systems carrying out any suitable steps of any of the method of FIG. 10.

Figure 11A:
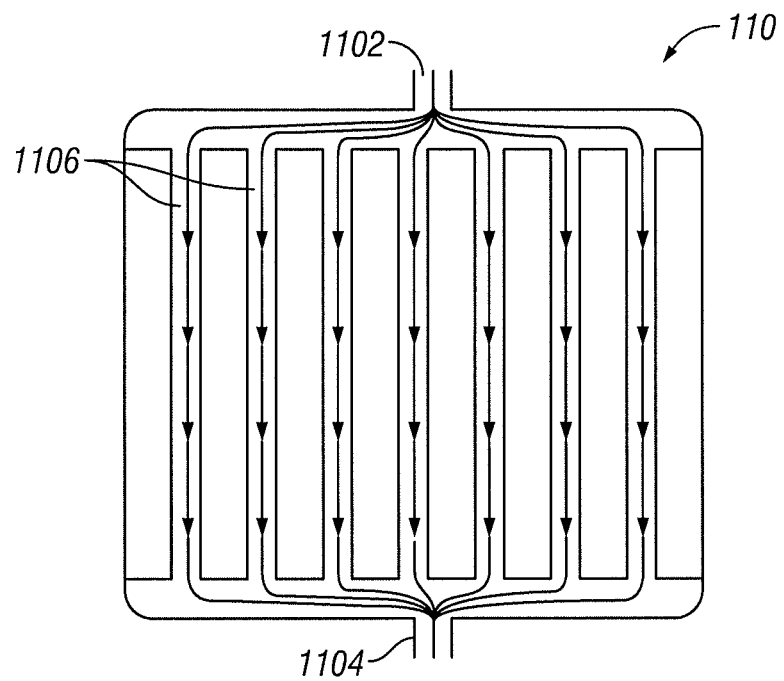
FIGS. 11A-11D illustrates embodiments of implementing a heat exchanger using solid materials.

FIGS. 11A-11D illustrates embodiments of implementing heat exchanger 110 of FIG. 1 using solid materials. FIG. 11A depicts blood from patient 102 flowing through inlet 1102, through channels 1106, and out through outlet 1104 to eventually return to patient 102 at a rate in the range of 1.5 to 15 liters per minute. Heat exchanger 110 can be formed of a solid material that is heated to a temperature within the range of, e.g., 42 and 46 degrees Celsius. Any suitable shape can be used for heat exchanger 110. Examples of such shapes include: cylindrical, cubical, irregular, spiral, conical, spherical, cuboidal, prism-shaped, and pyramidal. Any suitable material can be used to form the solid. Examples of such materials include: nylon, aluminum, stainless steel, titanium, polypropylene, polyester, or any suitable combination of the preceding. Channels 1106 may be formed in the solid material using any suitable technique. Examples of such techniques include drilling holes into a block of solid material, milling a solid block of material, or forming the channels by combining several pieces of solid material that are appropriately cut.

Figure 11B:
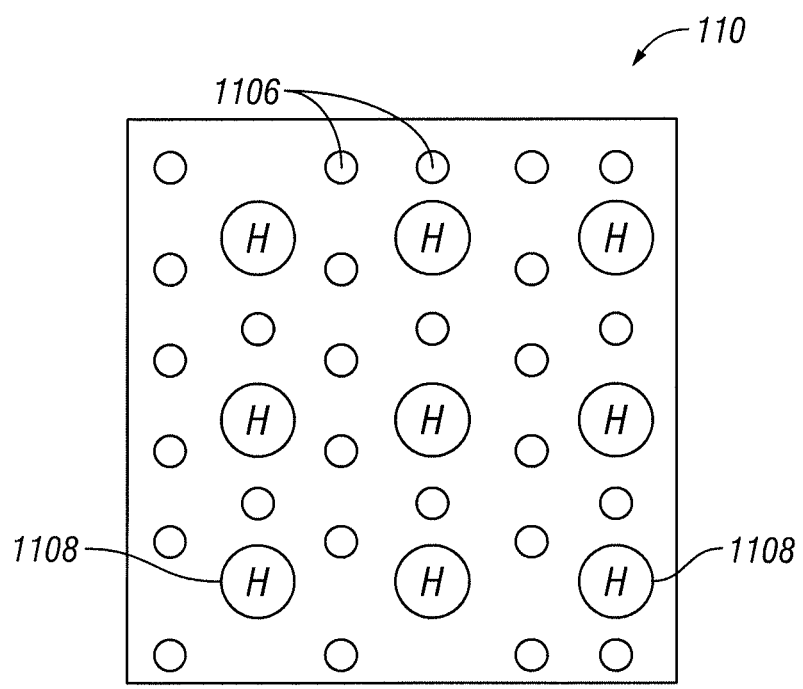
Figure 11C:
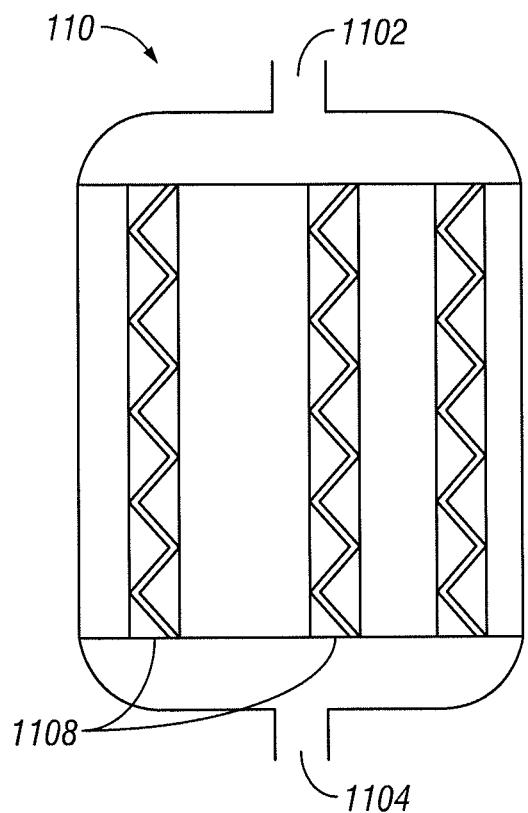

FIGS. 11B and 11C are a top view and a side view, respectively, of one embodiment of heat exchanger 110 implemented using solid materials illustrating how heat can be applied within heat exchanger 110. FIGS. 11B and 11C illustrate one embodiment of heat exchanger 110 where heating elements 1108 are placed through the solid material and around channels 1106. In this manner, e.g., heat transfers from heating elements 1108 to the blood in channels 1106. Heating elements 1108, in some embodiments, may be placed to facilitate even heating of the solid material.

Figure 11D:
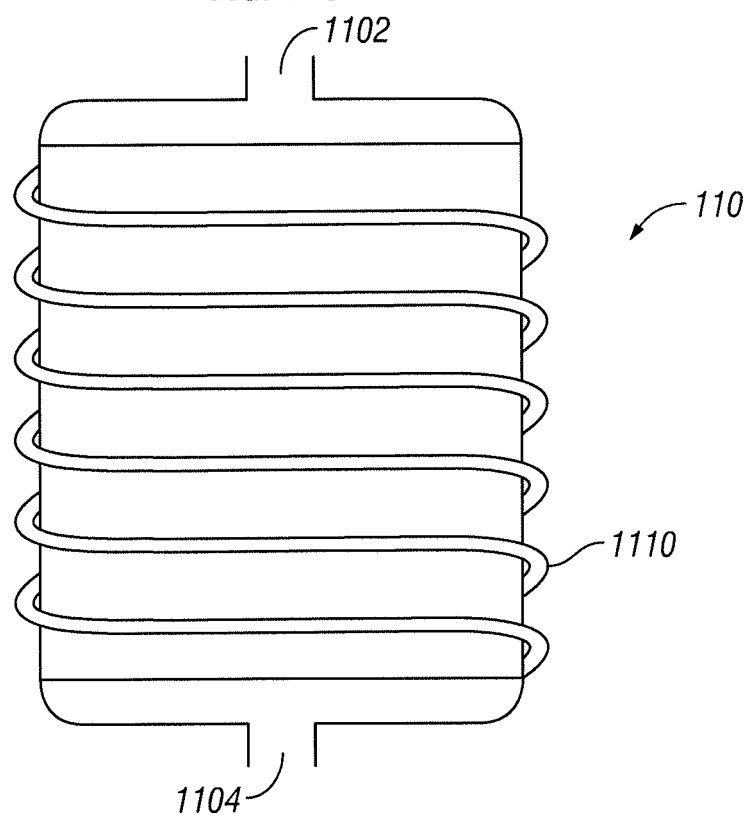

FIG. 11D illustrates one embodiment of heat exchanger 110 implemented using solid materials illustrating how heat can be applied externally to heat exchanger 110. Heating coil 1110 is placed around heat exchanger 110 to apply heat to the solid material within which blood is flowing via inlet 1102 and outlet 1104. Heating elements can be used instead of, or in addition to, heating coils. In some embodiments, heat exchanger 110 implemented using solid materials can have heat applied using some or all of the techniques depicted in FIGS. 11B-11D.

In some embodiments, thermostats may be used to facilitate control over heating heat exchanger 110 implemented using solid materials (e.g., as depicted in FIGS. 11A-11D). For example, thermostats may measure and control the temperature of heating elements 1108 and/or heating coil 1110. Signals may be sent to a control device that monitors and adjusts the target temperature of heat exchanger 110 as may be suitable.

Figure 12C:
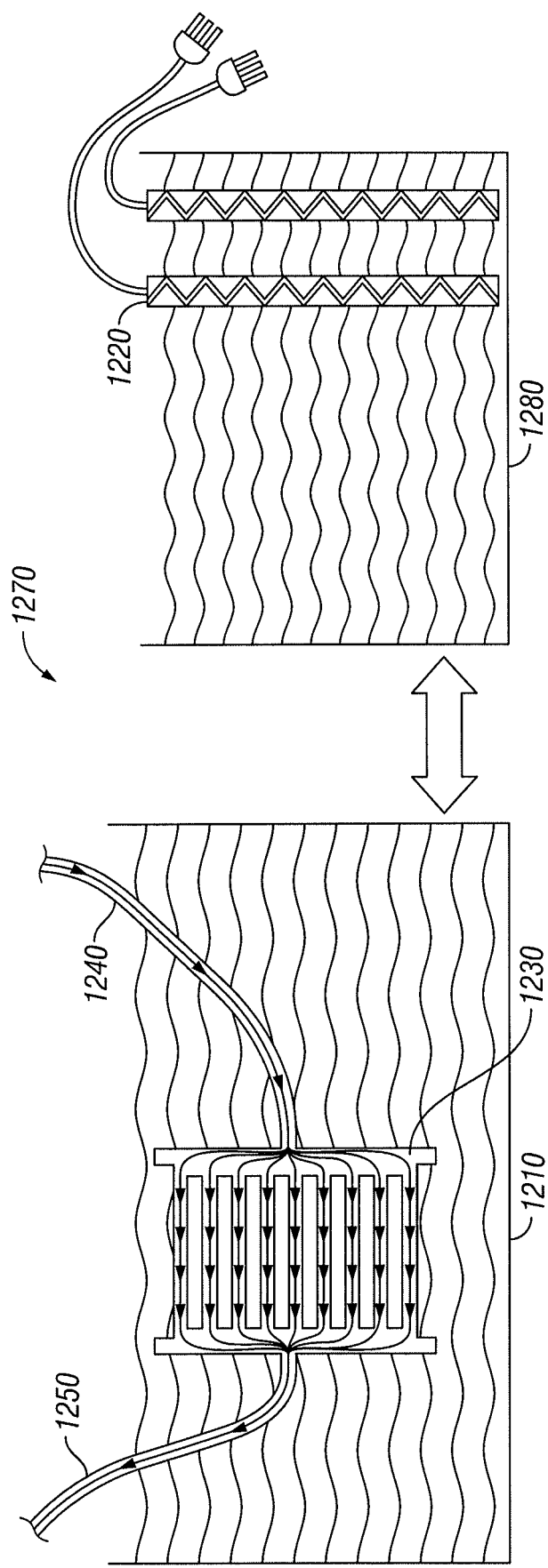

FIGS. 12A-C illustrate embodiments of heat exchanging systems. These systems can be used instead of, in addition to, or combined with heat exchanger 110 and heat source 112 of FIG. 1. FIG. 12A illustrates one embodiment of heat exchanging system 1200 that includes reservoir 1210 holding a fluid and heat source 1220 that heats the fluid. Blood flows to heat exchanger 1230 via inlet 1240 and out of heat exchanger 1230 via outlet 1250; heat is transferred to the blood. Circulation subsystem 1260 (e.g., propellers, jets, and/or suction devices) may be used to move fluid within reservoir 1210 to facilitate even heat distribution throughout reservoir 1210; in some embodiments, circulation subsystem 1260 may not be included in heat exchanging system 1200. In various embodiments, the components of heat exchanging system 1200 may be configured in various, suitable locations within reservoir 1210 or external to reservoir 1210. For example, heat source 1220 can be implemented using one or more heating elements, one or more heating coils, and/or a natural gas flame and these can be placed in various locations in reservoir 1210 to facilitate even heating of the liquid held by reservoir 1210.

FIG. 12B illustrates one embodiment of heat exchanger 1230. Heat exchanger 1230 includes channels 1232 through which blood flows from inlet 1240 to outlet 1250. Heat exchanger can, in some embodiments, also include spaces 1234 between channels 1232. Spaces 1234 can facilitate heating of the blood to allow the heated fluid in reservoir 1210 to surround channels 1232. Any suitable material(s) can be used in heat exchanger 1230, such as one or more of the following: stainless steel, titanium, polyester, polypropylene, and nylon.

FIG. 12C illustrates one embodiment of heat exchanging system 1270 that uses multiple reservoirs. Reservoir 1210 includes heated fluid that provides heat to heat exchanger 1230. Heat exchanger 1230 is immersed in the heated fluid of reservoir 1210 and has blood pass through it via inlet 1240 and outlet 1250; heat exchanger 1230 is configured to heat the blood. The heated liquid in reservoir 1210 comes from reservoir 1280 that includes heat source 1220 to heat liquid in reservoir 1280. Heated liquid from reservoir 1280 can be sent to reservoir 1210 using any suitable technique, including piping the liquid and/or pumping the liquid. The heated liquid can be returned from reservoir 1210 to reservoir 1280; this, in some embodiments, may lead to circulation of the heated liquid around heat exchanger 1230 and facilitate heat transfer. The flow rate of the heated liquid between reservoirs 1210 and 1280 may be any suitable rate; for example, the rate may be between 1 liter and 500 gallons per minute in one or both directions.

The fluid in the reservoirs discussed above with respect to FIGS. 12A-C can be any suitable fluid. Examples include water, alcohol, high viscosity liquids, and mercury. The reservoirs discussed above can be of any suitable size; for example, the sizes can range from two quarts to five thousand gallons. The fluids can be heated to any suitable temperature; for example, the fluids can be heated to a temperature within the range of 42-46 degrees Celsius. The flow of blood through the system depicted in FIGS. 12A-C can be of any suitable speed; for example, blood can flow at rate between 1.4 liters per minute to 14 liters per minute. Reservoirs 1210 and 1280 can be of any suitable shape; they may be the same or different shapes and such shapes can include cylinders, rectangular or triangular prisms, cubes, or irregular shapes.

Figure 13A:
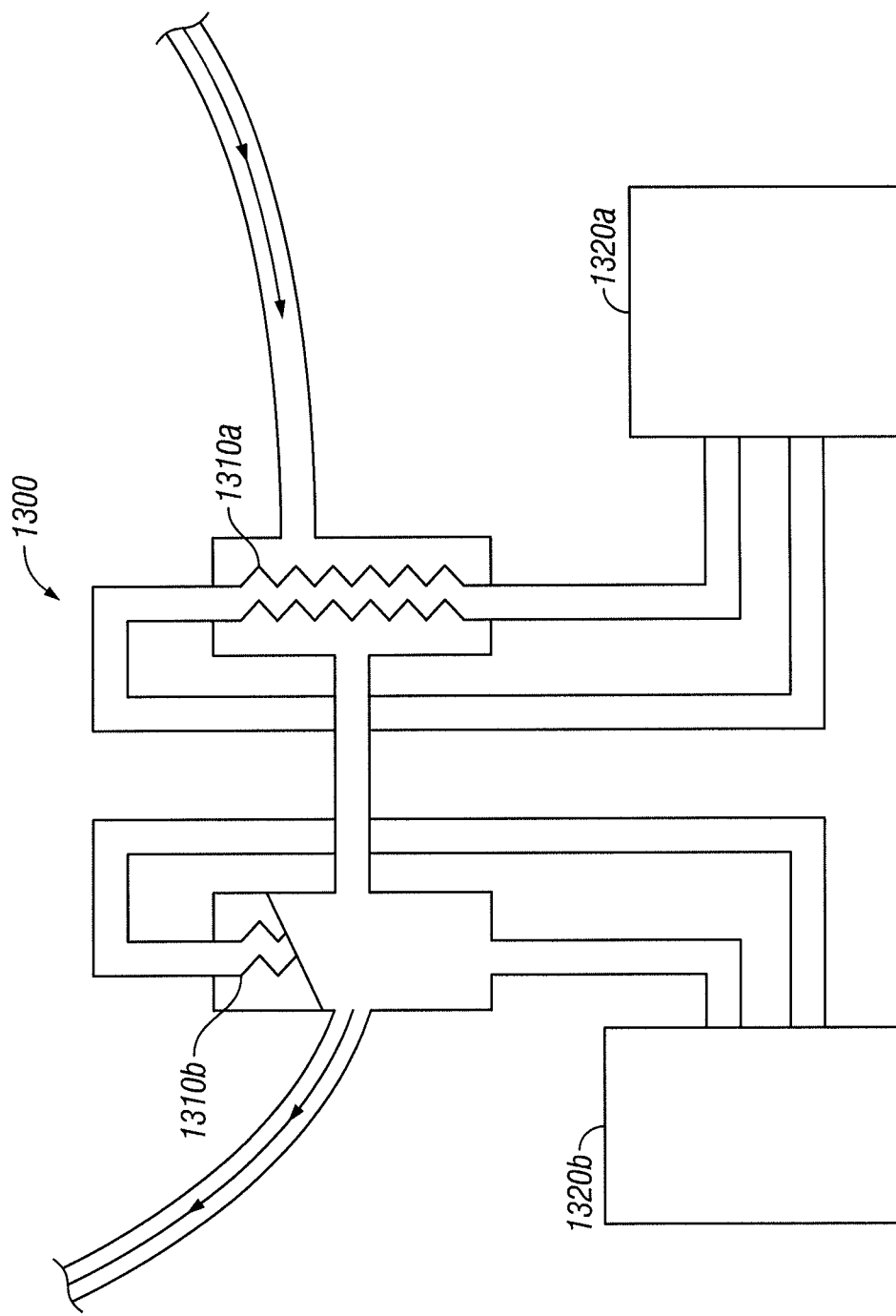
FIGS. 13A-13B illustrate embodiments of heat exchanging systems using multiple heat exchangers.
Figure 13B:
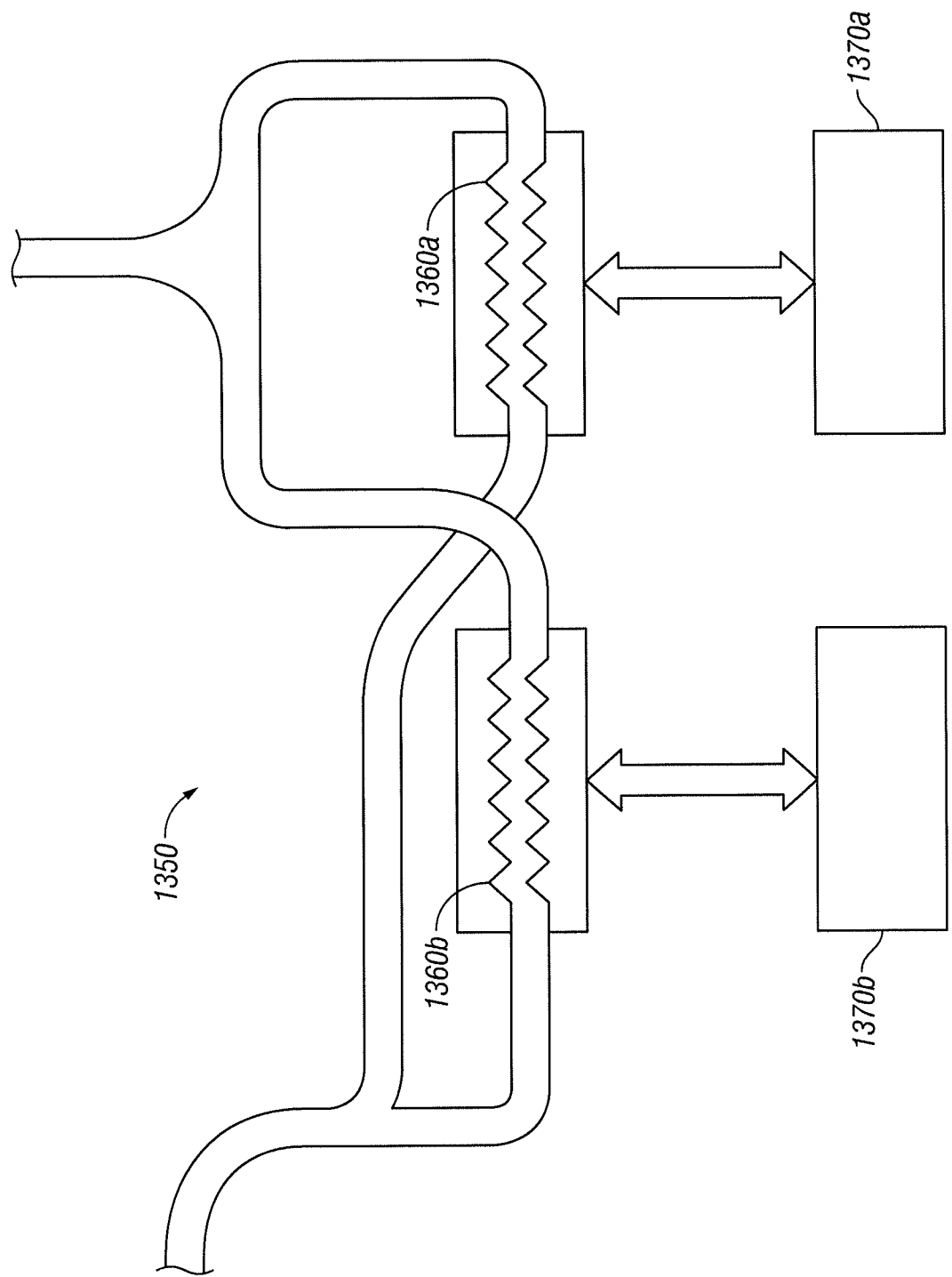

FIGS. 13A-B illustrate embodiments of heat exchanging systems using multiple heat exchangers. These systems can be used instead of, in addition to, or combined with heat exchanger 110 and heat source 112 of FIG. 1. FIG. 13A illustrates one embodiment of heat exchanging system 1300 configured such that heat exchangers 1310a and 1310b are connected in series. Blood from patient 102 enters heat exchanger 1310a, exits heat exchanger 1310a after being heated, and then enters heat exchanger 1310b. Blood exiting heat exchanger 1310b is further heated. Heat exchangers 1310a and 1310b use heated liquid from heat sources 1320a and 1320b, respectively, to apply heat to the blood. Flow rates for the heated liquids circulated by heat sources 1320a and 1320b at any suitable rate such as rates between 1 liter per minute to 250 gallons per minute. In various embodiments, heat exchangers 1310a and 1310b as well as heat sources 1320a and 1320b can be implemented using any of the techniques discussed above with respect to FIGS. 1-12C. In some embodiments, heat exchangers 1310a and 1310b can use less or more sources for heated liquid than two as depicted in FIG. 13A. In some embodiments, more than two heat exchangers can be connected in series, such as 3, 4, 5, 6, or a greater number of heat exchangers; each of such heat exchangers can use the same or different sources of heated liquid in any suitable combination.

FIG. 13B illustrates one embodiment of heat exchanging system 1350 configured such that heat exchangers 1360a and 1360b are connected in parallel. The blood stream from patient 102 is divided into two separate streams and one stream enters heat exchanger 1360a while the other enters heat exchanger 1310b. After the blood streams are heated in these exchangers, they are recombined. Heat exchangers 1360*a* and 1360*b* use heated liquid from heat sources 1370*a* and 1370*b*, respectively, to apply heat to the blood. Flow rates for the heated liquids circulated by heat sources 1370*a* and 1370*b* at any suitable rate such as rates between 1 liter per minute to 250 gallons per minute. In various embodiments, heat exchangers 1360*a* and 1360*b* as well as heat sources 1370*a* and 1370*b* can be implemented using any of the techniques discussed above with respect to FIGS. 1-12C. In some embodiments, heat exchangers 1360*a* and 1360*b* can use less or more sources for heated liquid than two as depicted in FIG. 13A. In some embodiments, more than two heat exchangers can be connected in parallel, such as 3, 4, 5, 6, or a greater number of heat exchangers; each of such heat exchangers can use the same or different sources of heated liquid in any suitable combination.

In some embodiments, the techniques discussed above with respect to FIGS. 13A and 13B can be combined. For example, blood can be heated using two or more heat exchangers that are in series as well as two or more heat exchangers that are in parallel. Any suitable combination of heat exchangers connected in parallel or in series may be used to heat the blood. In some embodiments, the use of multiple heat exchangers can reduce the temperature needed for the heated liquid to achieve the desired blood temperature and/or reduce the time it takes to heat the blood to the desired temperature. This can result in treatments that last a shorter period of time and reduce the health risks of the patient whose blood is being heated.

Figure 14:
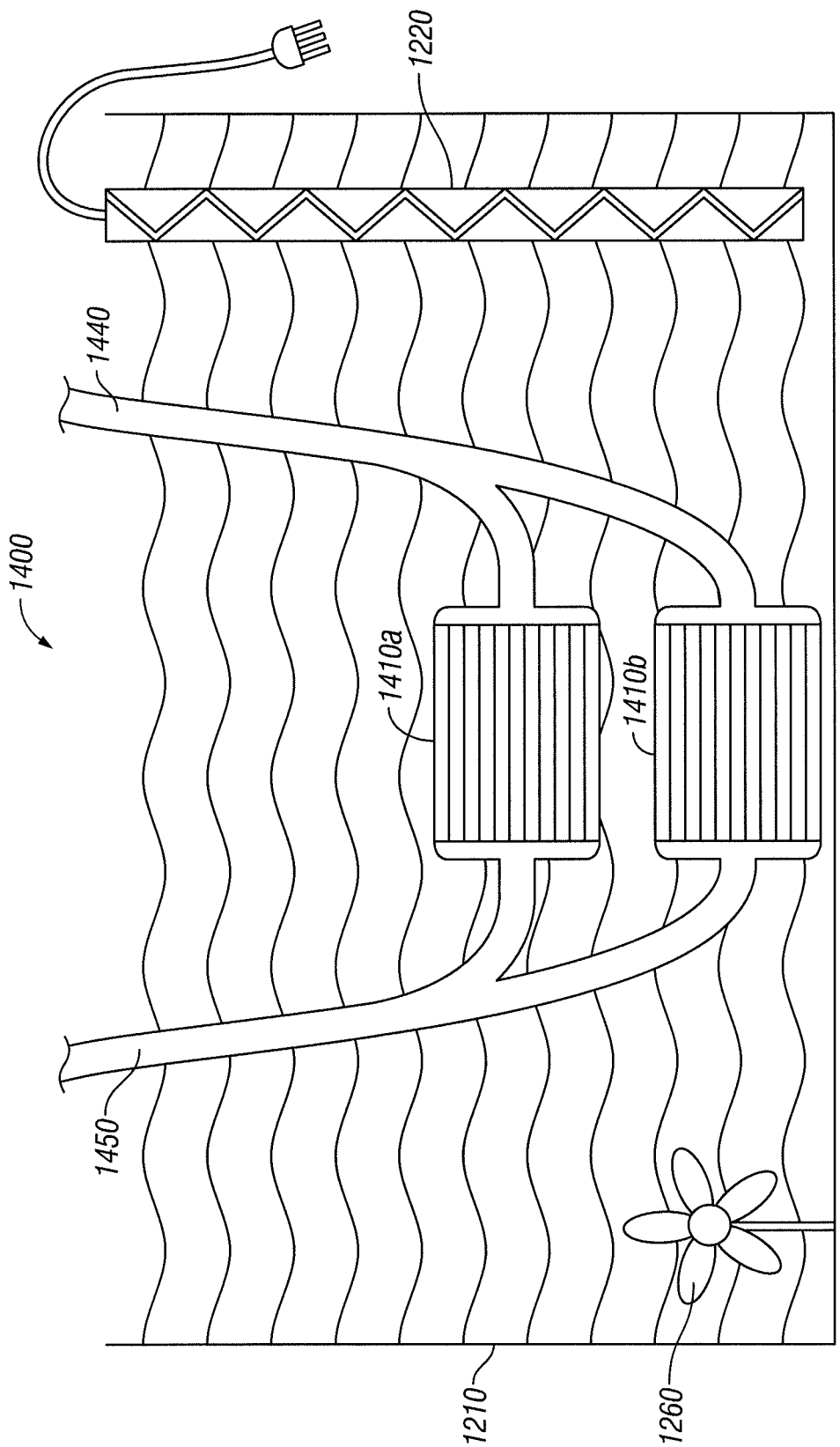
FIG. 14 illustrates one embodiment of a heat exchanging system configured to use a membrane to facilitate transfer of heat to the blood from a patient.

FIG. 14 illustrates one embodiment of heat exchanging system 1400 configured to use a membrane to facilitate transfer of heat to the blood from a patient. This system can be used instead of, in addition to, or combined with heat exchanger 110 and heat source 112 of FIG. 1. FIG. 14 illustrates one embodiment of heat exchanging system 1400 that includes reservoir 1210 holding a fluid and heat source 1220 that heats the fluid. Blood flows to membranes 1410*a-b* (arranged in parallel) via inlet 1440 and out of membranes 1410*a-b* via outlet 1450; heat can be transferred to the blood. Circulation subsystem 1260 (e.g., propellers, jets, and/or suction devices) may be used to move fluid within reservoir 1210 to facilitate even heat distribution throughout reservoir 1210; in some embodiments, circulation subsystem 1260 may not be included in heat exchanging system 1400. In various embodiments, components 1210, 1220, and 1260 may be implemented as discussed above with respect to FIGS. 12A-12C. As an example, suitable blood flow rates for heat exchanging system 1400 can be in the range of 1.4 liters per minute to 15 liters per minute; other blood flow rates disclosed above can also be used.

In some embodiments, system 1400 may include less or more than the two depicted membranes 1410*a-b*. Such membranes may be connected in parallel (as depicted in FIG. 14), in series, or in any suitable combination of parallel and series configurations. As an example, a micro-porous membrane, such as a dialysis membrane cartridge, may be used to implement membranes 1410*a-b*. In some embodiments, membranes 1410*a-b* can serve as a heat exchanger to heat the blood and to remove toxins, inflammatory mediators, or other matter from the blood (examples of which are discussed above with respect to toxin removal system 106 of FIG. 1). Such a membrane can use diffusion or convection dialysis techniques and can remove toxins up to 50,000 Daltons or more. This can assist in removing cytokines, dead cancer cells, and waste created in the process of heating the patient's blood.

In various embodiments, any suitable size of membrane can be used to implement membranes 1410*a-b*. For example, a microporous membrane cartridge with an effective surface area of 1.81 to 18 square meters could be used. As examples, a cartridge with an effective surface area of 1.85 to 18 square meters, 1.90 to 18 square meters, or 2.0 to 18 square meters may be used. In other specific embodiments, a cartridge with an effective surface area of between 1.18 to 5 square meters, 1.85 to 5 square meters, 1.90 to 5 square meters, or 2.0 to 5 square meters may be used. This can allow for greater blood and heat contact time and could reduce the amount of time it takes to heat the blood traveling through the single cartridge. It can allow for reducing the temperature of the heat source (e.g., to 42.5 to 43 or 43.9 degrees Celsius) while being able to heat the blood at a desired speed or at a faster speed. This can result, in some embodiments, from the greater contact time the blood has with the heat source. Larger membrane cartridges or alternative materials can be used in various embodiments (e.g., up to 2.4 square meters of effective membrane filter media in a single micro-porous cartridge). The membranes can be configured to be modular such that more than one membrane can be connected together. As examples, 2, 3, 4, 5, 6, or 7 membranes can be connected together in a modular fashion. The discussion of the implementation of membranes 1410*a-b* can be used to implement toxin removal system 106 of FIG. 1 discussed above (e.g., diffusion or convection dialysis machines used to implement toxin removal system 106 can use any implementation of membranes 1410*a-b* discussed herein).

In some embodiments, one or more of membranes 1410*a-b* may be replaced with, or supplemented by, one or more heat exchangers having a surface area of, for example, six square inches or greater (e.g., one square foot or greater); such heat exchanger(s) can have a surface area in any of the ranges recited above for microporous membrane cartridges. Examples of materials used in such heat exchanger(s) include, but are not limited to, steel, stainless steel, plastic, titanium, and other suitable materials. In operation, as an example, the heat exchanger(s) can sit submerged in fluid held by reservoir 1210 and can heat the blood of a patient. This can occur by having blood on one side of the heat exchanger(s), and having another side of the heat exchanger(s) in contact with the heated liquid.

In some embodiments, heat exchanging system 1400 may operate as follows. Discussion of one of membranes 1410*a-b* can apply to the other of membranes 1410*a-b*, or other of alternative materials used in place of one or more of these membranes. Heated water in reservoir 1210 can flow around the surface area of the outside of membrane 1410*a* (which can be implemented as a single cartridge). Blood can be flowing through the center, or inside of the hollow fiber membrane strands, of membrane 1410*a*. Strands of membrane 1410*a* can have a separate chamber, on the inside, from the outside of the material. In some embodiments, heated water can run through the inside of fibers of membrane 1410*a*, and the blood can run on the outside of the fibers. The blood can be in a separate chamber on the outside of the bundle of fibers. Heat from the water will transfer to the cooler blood from a patient, as the blood travels through the bundle of individual hollow fiber membrane strands, with the cooler blood flowing inside the fibers and the heat source of water being on the outside of the micro-porous membrane individual strands that comprise the cartridge.

In some embodiments, membranes 1410*a-b* can implement convection dialysis. They can cause a solvent drag where solute is carried (in a solution) across a semi-permeable membrane in response to a transmembrane pressure gradient. Efficiencies of this process can be controlled by selection of the porosity of the membrane and the hydrostatic pressure of the blood, which can depend upon the flow rate of the blood. As examples, membranes 1410a-b can have an effective removal ability of 0.01 to 5,000 or 6,000 Daltons or of 1 to 50,000 Daltons or higher.

In various embodiments, some, none, or all of the following advantages can be present in the various embodiments discussed above. Induced hyperthermia can be applied to the entire body. Blood can be maintained at a temperature between 42 and 43.2 degrees Celsius (or at any of the temperature ranges or temperatures discussed above) while being removed and pumped into the body. Induced hyperthermia can be accomplished without the need of a heat chamber. One or more of the embodiments described above may be used as a standard of care and treatment for various cancers or other maladies and can reduce or avoid the need of further treatment (e.g., surgical removal of tumor or cancer cells). One or more of the techniques discussed above may enable induced hyperthermia such that: a temperature of 42 degrees Celsius or slightly higher (e.g., such as any of the temperature ranges or temperatures discussed above) to all, or substantially all, of the cancer cells in a body for an appropriate duration of time (such as any of the ranges of time discussed above); the entire body (or the important parts of the body) can be heated substantially consistently throughout the treatment; the core body (or the important parts of the body) temperature, including the brain's temperature, can be accurately monitored. A precise, body-wide, controllable hyperthermia method can be achieved that can kill all, nearly all, or a substantial number of the cancer cells in a patient over their entire body or substantially their entire body without harming (or severely harming) or damaging the patient either during the procedure, hours after the procedure, or one or more days after the procedure. A high blood flow rate may be enabled so that induced hyperthermia can raise the core body temperature to the range of 42 to 43.2 degrees Celsius (or any of the temperature ranges or temperatures discussed above) within 45 minutes (or any of the above discussed time ranges) without raising the temperature of the blood to 44 to 48 degrees Celsius. Convection dialysis can be employed to remove toxins and/or pro inflammatory mediators created by full body induced hyperthermia that are in the range of 1-50,000 Daltons or above; dialysis (convection or diffusion) can be performed during the induced hyperthermia and after the induced hyperthermia (e.g., up to 48 hours after induced hyperthermia, or any of the time durations discussed above) to better remove toxins and/or pro inflammatory mediators. Convection dialysis can be performed such that plasma water is electrolyte and acid-balanced through the dialysis filter medium and returned to the blood just prior to entering back into the patient's body to maintain physiological homeostasis and proper fluid balance.

Using one or more of the techniques above, tests were performed using a BECKMAN COULTER MODEL 731050 VI-CELL XR system. Blood was drawn one hour into the induced hyperthermia treatment, two hours into the induced hyperthermia treatment, and after the procedure (approximately two hours and forty-three minutes after beginning the procedure). The patient was a pig. The white cell counts were the same throughout the procedure including cell viability (e.g., little to no death of white blood cells). The blood being heated was never above 43.2 degrees Celsius. The invention can be used to treat mammals other than humans.

The following is a numbered list of examples identifying particular combinations of the techniques disclosed above. The present disclosure is not limited to the following combinations as the following combinations are only examples. The techniques and options discussed above can be combined in any suitable manner.

EXAMPLES

1. A system comprising:
   one or more pumps configured to pump blood in a fluid flow path at a collective rate of at least 4 liters per minute; and
   one or more dialysis modules coupled to the fluid flow path and configured to perform dialysis on at least a portion of the blood at a collective rate of at least 0.5 liters per minute.

2. The system of Example 1, wherein the one or more dialysis modules are configured to perform convection dialysis.

3. The system of Example 1, wherein the one or more dialysis modules are configured to perform diffusion dialysis.

4. One or more of the systems of Examples 1-3, further comprising a reintroduction module coupled to the fluid flow path and configured to add electrolyte-balanced fluid to at least a portion of the blood at a rate of at least 7 liters per hour.

5. The system of Example 4, wherein the electrolyte-balanced fluid is at a temperature of at least 35 degrees Celsius.

6. One or more of the systems of Examples 1-5, wherein the one or more pumps are configured to pump the blood at a collective rate of at least 4.5 liters per minute.

7. One or more of the systems of Examples 1-5, wherein the one or more pumps are configured to pump the blood at a collective rate of at least 5 liters per minute.

8. One or more of the systems of Examples 1-5, wherein the one or more pumps are configured to pump the blood at a collective rate of at least 5.5 liters per minute.

9. One or more of the systems of Examples 1-5, wherein the one or more pumps are configured to pump the blood at a collective rate of at least 6 liters per minute.

10. One or more of the systems of Examples 1-5, wherein the one or more pumps are configured to pump the blood at a collective rate of at least 6.5 liters per minute.

11. One or more of the systems of Examples 1-5, wherein the one or more pumps are configured to pump the blood at a collective rate of at least 7 liters per minute.

12. One or more of the systems of Examples 1-5, wherein the one or more pumps are configured to pump the blood at a collective rate of at least 7.5 liters per minute.

13. One or more of the systems of Examples 1-5, wherein the one or more pumps are configured to pump the blood at a collective rate of at least 8 liters per minute.

14. One or more of the systems of Examples 1-5, wherein the one or more pumps are configured to pump the blood at a collective rate of at least 8.5 liters per minute.

15. One or more of the systems of Examples 1-5, wherein the one or more pumps are configured to pump the blood at a collective rate of at least 9 liters per minute.

16. One or more of the systems of Examples 1-5, wherein the one or more pumps are configured to pump the blood at a collective rate between 4 and 4.5 liters per minute.

17. One or more of the systems of Examples 1-5, wherein the one or more pumps are configured to pump the blood at a collective rate between 4 and 5 liters per minute.

18. One or more of the systems of Examples 1-5, wherein the one or more pumps are configured to pump the blood at a collective rate between 4 and 5.5 liters per minute.

19. One or more of the systems of Examples 1-5, wherein the one or more pumps are configured to pump the blood at a collective rate between 4 and 6 liters per minute.

20. One or more of the systems of Examples 1-5, wherein the one or more pumps are configured to pump the blood at a collective rate between 4 and 6.5 liters per minute.

21. One or more of the systems of Examples 1-5, wherein the one or more pumps are configured to pump the blood at a collective rate between 4 and 7 liters per minute.

22. One or more of the systems of Examples 1-5, wherein the one or more pumps are configured to pump the blood at a collective rate between 4 and 7.5 liters per minute.

23. One or more of the systems of Examples 1-5, wherein the one or more pumps are configured to pump the blood at a collective rate between 4 and 8 liters per minute.

24. One or more of the systems of Examples 1-5, wherein the one or more pumps are configured to pump the blood at a collective rate between 4 and 8.5 liters per minute.

25. One or more of the systems of Examples 1-5, wherein the one or more pumps are configured to pump the blood at a collective rate between 4 and 9 liters per minute.

26. One or more of the systems of Examples 1-5, wherein the one or more pumps are configured to pump the blood at a collective rate between 4.5 and 9 liters per minute.

27. One or more of the systems of Examples 1-5, wherein the one or more pumps are configured to pump the blood at a collective rate between 5 and 9 liters per minute.

28. One or more of the systems of Examples 1-5, wherein the one or more pumps are configured to pump the blood at a collective rate between 5.5 and 9 liters per minute.

29. One or more of the systems of Examples 1-5, wherein the one or more pumps are configured to pump the blood at a collective rate between 6 and 9 liters per minute.

30. One or more of the systems of Examples 1-5, wherein the one or more pumps are configured to pump the blood at a collective rate between 6.5 and 9 liters per minute.

31. One or more of the systems of Examples 1-5, wherein the one or more pumps are configured to pump the blood at a collective rate between 7 and 9 liters per minute.

32. One or more of the systems of Examples 1-5, wherein the one or more pumps are configured to pump the blood at a collective rate between 7.5 and 9 liters per minute.

33. One or more of the systems of Examples 1-5, wherein the one or more pumps are configured to pump the blood at a collective rate between 8 and 9 liters per minute.

34. One or more of the systems of Examples 1-5, wherein the one or more pumps are configured to pump the blood at a collective rate between 8.5 and 9 liters per minute.

35. One or more of the systems of Examples 1-34, wherein the one or more dialysis modules are configured to perform dialysis on at least a portion of the blood at a collective rate of at least 0.55 liters per minute.

36. One or more of the systems of Examples 1-34, wherein the one or more dialysis modules are configured to perform dialysis on at least a portion of the blood at a collective rate of at least 0.6 liters per minute.

37. One or more of the systems of Examples 1-34, wherein the one or more dialysis modules are configured to perform dialysis on at least a portion of the blood at a collective rate of at least 0.65 liters per minute.

38. One or more of the systems of Examples 1-34, wherein the one or more dialysis modules are configured to perform dialysis on at least a portion of the blood at a collective rate of at least 0.7 liters per minute.

39. One or more of the systems of Examples 1-34, wherein the one or more dialysis modules are configured to perform dialysis on at least a portion of the blood at a collective rate of at least 0.75 liters per minute.

40. One or more of the systems of Examples 1-34, wherein the one or more dialysis modules are configured to perform dialysis on at least a portion of the blood at a collective rate of at least 0.8 liters per minute.

41. One or more of the systems of Examples 1-34, wherein the one or more dialysis modules are configured to perform dialysis on at least a portion of the blood at a collective rate of at least 0.85 liters per minute.

42. One or more of the systems of Examples 1-34, wherein the one or more dialysis modules are configured to perform dialysis on at least a portion of the blood at a collective rate of at least 0.9 liters per minute.

43. One or more of the systems of Examples 1-34, wherein the one or more dialysis modules are configured to perform dialysis on at least a portion of the blood at a collective rate of at least 0.95 liters per minute.

44. One or more of the systems of Examples 1-34, wherein the one or more dialysis modules are configured to perform dialysis on at least a portion of the blood at a collective rate of at least 1 liter per minute.

45. One or more of the systems of Examples 1-34, wherein the one or more dialysis modules are configured to perform dialysis on at least a portion of the blood at a collective rate of at least 1.1 liters per minute.

46. One or more of the systems of Examples 1-34, wherein the one or more dialysis modules are configured to perform dialysis on at least a portion of the blood at a collective rate of at least 1.2 liters per minute.

47. One or more of the systems of Examples 1-34, wherein the one or more dialysis modules are configured to perform dialysis on at least a portion of the blood at a collective rate of at least 1.3 liters per minute.

48. One or more of the systems of Examples 1-34, wherein the one or more dialysis modules are configured to perform dialysis on at least a portion of the blood at a collective rate of at least 1.4 liters per minute.

49. One or more of the systems of Examples 1-34, wherein the one or more dialysis modules are configured to perform dialysis on at least a portion of the blood at a collective rate of at least 1.5 liters per minute.

50. One or more of the systems of Examples 1-34, wherein the one or more dialysis modules are configured to perform dialysis on at least a portion of the blood at a collective rate of at least 1.6 liters per minute.

51. One or more of the systems of Examples 1-34, wherein the one or more dialysis modules are configured to perform dialysis on at least a portion of the blood at a collective rate of at least 1.7 liters per minute.

52. One or more of the systems of Examples 1-34, wherein the one or more dialysis modules are configured to perform dialysis on at least a portion of the blood at a collective rate of at least 1.8 liters per minute.

53. One or more of the systems of Examples 1-34, wherein the one or more dialysis modules are configured to perform dialysis on at least a portion of the blood at a collective rate of at least 1.9 liters per minute.

54. One or more of the systems of Examples 1-34, wherein the one or more dialysis modules are configured to perform dialysis on at least a portion of the blood at a collective rate of at least 2 liters per minute.

55. One or more of the systems of Examples 1-34, wherein the one or more dialysis modules are configured to perform dialysis on at least a portion of the blood at a collective rate of at least 2.1 liters per minute.

56. One or more of the systems of Examples 1-34, wherein the one or more dialysis modules are configured to perform dialysis on at least a portion of the blood at a collective rate of at least 2.2 liters per minute.

57. One or more of the systems of Examples 1-34, wherein the one or more dialysis modules are configured to perform dialysis on at least a portion of the blood at a collective rate of at least 2.3 liters per minute.

58. One or more of the systems of Examples 1-34, wherein the one or more dialysis modules are configured to perform dialysis on at least a portion of the blood at a collective rate of at least 2.4 liters per minute.

59. One or more of the systems of Examples 1-34, wherein the one or more dialysis modules are configured to perform dialysis on at least a portion of the blood at a collective rate of at least 2.5 liters per minute.

60. One or more of the systems of Examples 1-34, wherein the one or more dialysis modules are configured to perform dialysis on at least a portion of the blood at a collective rate of at least 2.6 liters per minute.

61. One or more of the systems of Examples 1-34, wherein the one or more dialysis modules are configured to perform dialysis on at least a portion of the blood at a collective rate of at least 2.7 liters per minute.

62. One or more of the systems of Examples 1-34, wherein the one or more dialysis modules are configured to perform dialysis on at least a portion of the blood at a collective rate of at least 2.8 liters per minute.

63. One or more of the systems of Examples 1-34, wherein the one or more dialysis modules are configured to perform dialysis on at least a portion of the blood at a collective rate of at least 2.9 liters per minute.

64. One or more of the systems of Examples 1-34, wherein the one or more dialysis modules are configured to perform dialysis on at least a portion of the blood at a collective rate of at least 3 liters per minute.

65. One or more of the systems of Examples 1-34, wherein the one or more dialysis modules are configured to perform dialysis on at least a portion of the blood at a collective rate between 0.5 and 0.55 liters per minute.

66. One or more of the systems of Examples 1-34, wherein the one or more dialysis modules are configured to perform dialysis on at least a portion of the blood at a collective rate between 0.5 and 0.6 liters per minute.

67. One or more of the systems of Examples 1-34, wherein the one or more dialysis modules are configured to perform dialysis on at least a portion of the blood at a collective rate between 0.5 and 0.65 liters per minute.

68. One or more of the systems of Examples 1-34, wherein the one or more dialysis modules are configured to perform dialysis on at least a portion of the blood at a collective rate between 0.5 and 0.7 liters per minute.

69. One or more of the systems of Examples 1-34, wherein the one or more dialysis modules are configured to perform dialysis on at least a portion of the blood at a collective rate between 0.5 and 0.75 liters per minute.

70. One or more of the systems of Examples 1-34, wherein the one or more dialysis modules are configured to perform dialysis on at least a portion of the blood at a collective rate between 0.5 and 0.8 liters per minute.

71. One or more of the systems of Examples 1-34, wherein the one or more dialysis modules are configured to perform dialysis on at least a portion of the blood at a collective rate between 0.5 and 0.85 liters per minute.

72. One or more of the systems of Examples 1-34, wherein the one or more dialysis modules are configured to perform dialysis on at least a portion of the blood at a collective rate between 0.5 and 0.9 liters per minute.

73. One or more of the systems of Examples 1-34, wherein the one or more dialysis modules are configured to perform dialysis on at least a portion of the blood at a collective rate between 0.5 and 0.95 liters per minute.

74. One or more of the systems of Examples 1-34, wherein the one or more dialysis modules are configured to perform dialysis on at least a portion of the blood at a collective rate between 0.5 and 1 liters per minute.

75. One or more of the systems of Examples 1-34, wherein the one or more dialysis modules are configured to perform dialysis on at least a portion of the blood at a collective rate between 0.5 and 1.1 liters per minute.

76. One or more of the systems of Examples 1-34, wherein the one or more dialysis modules are configured to perform dialysis on at least a portion of the blood at a collective rate between 0.5 and 1.2 liters per minute.

77. One or more of the systems of Examples 1-34, wherein the one or more dialysis modules are configured to perform dialysis on at least a portion of the blood at a collective rate between 0.5 and 1.3 liters per minute.

78. One or more of the systems of Examples 1-34, wherein the one or more dialysis modules are configured to perform dialysis on at least a portion of the blood at a collective rate between 0.5 and 1.4 liters per minute.

79. One or more of the systems of Examples 1-34, wherein the one or more dialysis modules are configured to perform dialysis on at least a portion of the blood at a collective rate between 0.5 and 1.5 liters per minute.

80. One or more of the systems of Examples 1-34, wherein the one or more dialysis modules are configured to perform dialysis on at least a portion of the blood at a collective rate between 0.5 and 1.6 liters per minute.

81. One or more of the systems of Examples 1-34, wherein the one or more dialysis modules are configured to perform dialysis on at least a portion of the blood at a collective rate between 0.5 and 1.7 liters per minute.

82. One or more of the systems of Examples 1-34, wherein the one or more dialysis modules are configured to perform dialysis on at least a portion of the blood at a collective rate between 0.5 and 1.8 liters per minute.

83. One or more of the systems of Examples 1-34, wherein the one or more dialysis modules are configured to perform dialysis on at least a portion of the blood at a collective rate between 0.5 and 1.9 liters per minute.

84. One or more of the systems of Examples 1-34, wherein the one or more dialysis modules are configured to perform dialysis on at least a portion of the blood at a collective rate between 0.5 and 2 liters per minute.

85. One or more of the systems of Examples 1-34, wherein the one or more dialysis modules are configured to perform dialysis on at least a portion of the blood at a collective rate between 0.5 and 2.1 liters per minute.

86. One or more of the systems of Examples 1-34, wherein the one or more dialysis modules are configured to perform dialysis on at least a portion of the blood at a collective rate between 0.5 and 2.2 liters per minute.

87. One or more of the systems of Examples 1-34, wherein the one or more dialysis modules are configured to perform dialysis on at least a portion of the blood at a collective rate between 0.5 and 2.3 liters per minute.

88. One or more of the systems of Examples 1-34, wherein the one or more dialysis modules are configured to perform dialysis on at least a portion of the blood at a collective rate between 0.5 and 2.4 liters per minute.

89. One or more of the systems of Examples 1-34, wherein the one or more dialysis modules are configured to perform dialysis on at least a portion of the blood at a collective rate between 0.5 and 2.5 liters per minute.

90. One or more of the systems of Examples 1-34, wherein the one or more dialysis modules are configured to perform dialysis on at least a portion of the blood at a collective rate between 0.5 and 2.6 liters per minute.

91. One or more of the systems of Examples 1-34, wherein the one or more dialysis modules are configured to perform dialysis on at least a portion of the blood at a collective rate between 0.5 and 2.7 liters per minute.

92. One or more of the systems of Examples 1-34, wherein the one or more dialysis modules are configured to perform dialysis on at least a portion of the blood at a collective rate between 0.5 and 2.8 liters per minute.

93. One or more of the systems of Examples 1-34, wherein the one or more dialysis modules are configured to perform dialysis on at least a portion of the blood at a collective rate between 0.5 and 2.9 liters per minute.

94. One or more of the systems of Examples 1-34, wherein the one or more dialysis modules are configured to perform dialysis on at least a portion of the blood at a collective rate between 0.5 and 3 liters per minute.

95. One or more of the systems of Examples 1-34, wherein the one or more dialysis modules are configured to perform dialysis on at least a portion of the blood at a collective rate between 0.55 and 3 liters per minute.

96. One or more of the systems of Examples 1-34, wherein the one or more dialysis modules are configured to perform dialysis on at least a portion of the blood at a collective rate between 0.6 and 3 liters per minute.

97. One or more of the systems of Examples 1-34, wherein the one or more dialysis modules are configured to perform dialysis on at least a portion of the blood at a collective rate between 0.65 and 3 liters per minute.

98. One or more of the systems of Examples 1-34, wherein the one or more dialysis modules are configured to perform dialysis on at least a portion of the blood at a collective rate between 0.7 and 3 liters per minute.

99. One or more of the systems of Examples 1-34, wherein the one or more dialysis modules are configured to perform dialysis on at least a portion of the blood at a collective rate between 0.75 and 3 liters per minute.

100. One or more of the systems of Examples 1-34, wherein the one or more dialysis modules are configured to perform dialysis on at least a portion of the blood at a collective rate between 0.8 and 3 liters per minute.

101. One or more of the systems of Examples 1-34, wherein the one or more dialysis modules are configured to perform dialysis on at least a portion of the blood at a collective rate between 0.85 and 3 liters per minute.

102. One or more of the systems of Examples 1-34, wherein the one or more dialysis modules are configured to perform dialysis on at least a portion of the blood at a collective rate between 0.9 and 3 liters per minute.

103. One or more of the systems of Examples 1-34, wherein the one or more dialysis modules are configured to perform dialysis on at least a portion of the blood at a collective rate between 0.95 and 3 liters per minute.

104. One or more of the systems of Examples 1-34, wherein the one or more dialysis modules are configured to perform dialysis on at least a portion of the blood at a collective rate between 1 and 3 liters per minute.

105. One or more of the systems of Examples 1-34, wherein the one or more dialysis modules are configured to perform dialysis on at least a portion of the blood at a collective rate between 1.1 and 3 liters per minute.

106. One or more of the systems of Examples 1-34, wherein the one or more dialysis modules are configured to perform dialysis on at least a portion of the blood at a collective rate between 1.2 and 3 liters per minute.

107. One or more of the systems of Examples 1-34, wherein the one or more dialysis modules are configured to perform dialysis on at least a portion of the blood at a collective rate between 1.3 and 3 liters per minute.

108. One or more of the systems of Examples 1-34, wherein the one or more dialysis modules are configured to perform dialysis on at least a portion of the blood at a collective rate between 1.4 and 3 liters per minute.

109. One or more of the systems of Examples 1-34, wherein the one or more dialysis modules are configured to perform dialysis on at least a portion of the blood at a collective rate between 1.5 and 3 liters per minute.

110. One or more of the systems of Examples 1-34, wherein the one or more dialysis modules are configured to perform dialysis on at least a portion of the blood at a collective rate between 1.6 and 3 liters per minute.

111. One or more of the systems of Examples 1-34, wherein the one or more dialysis modules are configured to perform dialysis on at least a portion of the blood at a collective rate between 1.7 and 3 liters per minute.

112. One or more of the systems of Examples 1-34, wherein the one or more dialysis modules are configured to perform dialysis on at least a portion of the blood at a collective rate between 1.8 and 3 liters per minute.

113. One or more of the systems of Examples 1-34, wherein the one or more dialysis modules are configured to perform dialysis on at least a portion of the blood at a collective rate between 1.9 and 3 liters per minute.

114. One or more of the systems of Examples 1-34, wherein the one or more dialysis modules are configured to perform dialysis on at least a portion of the blood at a collective rate between 2 and 3 liters per minute.

115. One or more of the systems of Examples 1-34, wherein the one or more dialysis modules are configured to perform dialysis on at least a portion of the blood at a collective rate between 2.1 and 3 liters per minute.

116. One or more of the systems of Examples 1-34, wherein the one or more dialysis modules are configured to perform dialysis on at least a portion of the blood at a collective rate between 2.2 and 3 liters per minute.

117. One or more of the systems of Examples 1-34, wherein the one or more dialysis modules are configured to perform dialysis on at least a portion of the blood at a collective rate between 2.3 and 3 liters per minute.

118. One or more of the systems of Examples 1-34, wherein the one or more dialysis modules are configured to perform dialysis on at least a portion of the blood at a collective rate between 2.4 and 3 liters per minute.

119. One or more of the systems of Examples 1-34, wherein the one or more dialysis modules are configured to perform dialysis on at least a portion of the blood at a collective rate between 2.5 and 3 liters per minute.

120. One or more of the systems of Examples 1-34, wherein the one or more dialysis modules are configured to perform dialysis on at least a portion of the blood at a collective rate between 2.6 and 3 liters per minute.

121. One or more of the systems of Examples 1-34, wherein the one or more dialysis modules are configured to perform dialysis on at least a portion of the blood at a collective rate between 2.7 and 3 liters per minute.

122. One or more of the systems of Examples 1-34, wherein the one or more dialysis modules are configured to perform dialysis on at least a portion of the blood at a collective rate between 2.8 and 3 liters per minute.

123. One or more of the systems of Examples 1-34, wherein the one or more dialysis modules are configured to perform dialysis on at least a portion of the blood at a collective rate between 2.9 and 3 liters per minute.

124. One or more of the systems of Examples 1-123, wherein:
the one or more dialysis modules are configured to receive the portion of the blood at a location on the fluid flow path downstream from the one or more pumps; and
the one or more dialysis modules are configured to cause blood treated with dialysis to enter the fluid flow path upstream from the one or more pumps.

125. One or more of the systems of Examples 1-124, further comprising one or more heat exchangers coupled to the fluid flow path and configured to heat at least a portion of the blood to a temperature of at least 42 degrees Celsius.

126. The system of Example 125, wherein the one or more heat exchangers are configured to heat at least a portion of the blood to a temperature of at least 42.5 degrees Celsius.

127. The system of Example 125, wherein the one or more heat exchangers are configured to heat at least a portion of the blood to a temperature of at least 43 degrees Celsius.

128. The system of Example 125, wherein the one or more heat exchangers are configured to heat at least a portion of the blood to a temperature of at least 43.5 degrees Celsius.

129. The system of Example 125, wherein the one or more heat exchangers are configured to heat at least a portion of the blood to a temperature of at least 44 degrees Celsius.

130. The system of Example 125, wherein the one or more heat exchangers are configured to heat at least a portion of the blood to a temperature of at least 44.5 degrees Celsius.

131. The system of Example 125, wherein the one or more heat exchangers are configured to heat at least a portion of the blood to a temperature of at least 45 degrees Celsius.

132. The system of Example 125, wherein the one or more heat exchangers are configured to heat at least a portion of the blood to a temperature between 42 and 42.5 degrees Celsius.

133. The system of Example 125, wherein the one or more heat exchangers are configured to heat at least a portion of the blood to a temperature between 42 and 43 degrees Celsius.

134. The system of Example 125, wherein the one or more heat exchangers are configured to heat at least a portion of the blood to a temperature between 42 and 43.5 degrees Celsius.

135. The system of Example 125, wherein the one or more heat exchangers are configured to heat at least a portion of the blood to a temperature between 42 and 44 degrees Celsius.

136. The system of Example 125, wherein the one or more heat exchangers are configured to heat at least a portion of the blood to a temperature between 42 and 44.5 degrees Celsius.

137. The system of Example 125, wherein the one or more heat exchangers are configured to heat at least a portion of the blood to a temperature between 42 and 45 degrees Celsius.

138. The system of Example 125, wherein the one or more heat exchangers are configured to heat at least a portion of the blood to a temperature between 42.5 and 45 degrees Celsius.

139. The system of Example 125, wherein the one or more heat exchangers are configured to heat at least a portion of the blood to a temperature between 43 and 45 degrees Celsius.

140. The system of Example 125, wherein the one or more heat exchangers are configured to heat at least a portion of the blood to a temperature between 43.5 and 45 degrees Celsius.

141. The system of Example 125, wherein the one or more heat exchangers are configured to heat at least a portion of the blood to a temperature between 44 and 45 degrees Celsius.

142. The system of Example 125, wherein the one or more heat exchangers are configured to heat at least a portion of the blood to a temperature between 44.5 and 45 degrees Celsius.

143. One or more of the systems of Examples 1-142, further comprising one or more venting modules coupled to the fluid flow path, the one or more venting modules configured to remove carbon dioxide from at least a portion of the blood.

144. The system of Example 143, wherein the one or more venting modules are configured to add oxygen to at least a portion of the blood.

145. The system of Example 143, wherein the one or more venting modules are configured to cause at least a portion of the blood to flow through at least one membrane.

146. The system of Example 145, wherein the at least one membrane collectively has an effective surface area greater than 1.8 square meters.

147. One or more of the systems of Examples 1-146, further comprising an oxygenator coupled to the fluid flow path, the oxygenator configured to cause oxygen to be added to at least a portion of the blood.

148. One or more of the systems of Examples 1-147, further comprising a reintroduction module coupled to the fluid flow path and configured to add a substance to at least a portion of the blood that facilitates the production of reactive oxygen species within the blood.

149. The system of Example 148, wherein the substance comprises a free radical.

150. The system of Example 148, wherein the substance comprises an unstable substance.

151. The system of Example 148, wherein the substance comprises ozone.

152. The system of Example 148, wherein the substance comprises Freon.

153. The system of Example 148, wherein the substance comprises iron.

154. The system of Example 148, wherein the substance comprises copper.

155. The system of Example 148, wherein the substance comprises ozone and iron.

156. The system of Example 148, wherein the substance comprises ozone and copper.

157. A method comprising:
pumping blood in a fluid flow path at a rate of at least 4 liters per minute; and
performing dialysis on at least a portion of the blood from the fluid flow path at a rate of at least 0.5 liters per minute.

158. The method of Example 157, wherein performing dialysis comprises performing convection dialysis.

159. The method of Example 157, wherein performing dialysis comprises performing diffusion dialysis.

160. The method of Example 157, further comprising adding electrolyte-balanced fluid to at least a portion of the blood at a rate of at least 7 liters per hour.

161. The method of Example 160, wherein the electrolyte-balanced fluid is at a temperature of at least 35 degrees Celsius.

162. One or more of the methods of Examples 157-161, wherein the blood is pumped at a rate of at least 4.5 liters per minute.

163. One or more of the methods of Examples 157-161, wherein the blood is pumped at a rate of at least 5 liters per minute.

164. One or more of the methods of Examples 157-161, wherein the blood is pumped at a rate of at least 5.5 liters per minute.

165. One or more of the methods of Examples 157-161, wherein the blood is pumped at a rate of at least 6 liters per minute.

166. One or more of the methods of Examples 157-161, wherein the blood is pumped at a rate of at least 6.5 liters per minute.

167. One or more of the methods of Examples 157-161, wherein the blood is pumped at a rate of at least 7 liters per minute.

168. One or more of the methods of Examples 157-161, wherein the blood is pumped at a rate of at least 7.5 liters per minute.

169. One or more of the methods of Examples 157-161, wherein the blood is pumped at a rate of at least 8 liters per minute.

170. One or more of the methods of Examples 157-161, wherein the blood is pumped at a rate of at least 8.5 liters per minute.

171. One or more of the methods of Examples 157-161, wherein the blood is pumped at a rate of at least 9 liters per minute.

172. One or more of the methods of Examples 157-161, wherein the blood is pumped at a rate between 4 and 4.5 liters per minute.

173. One or more of the methods of Examples 157-161, wherein the blood is pumped at a rate between 4 and 5 liters per minute.

174. One or more of the methods of Examples 157-161, wherein the blood is pumped at a rate between 4 and 5.5 liters per minute.

175. One or more of the methods of Examples 157-161, wherein the blood is pumped at a rate between 4 and 6 liters per minute.

176. One or more of the methods of Examples 157-161, wherein the blood is pumped at a rate between 4 and 6.5 liters per minute.

177. One or more of the methods of Examples 157-161, wherein the blood is pumped at a rate between 4 and 7 liters per minute.

178. One or more of the methods of Examples 157-161, wherein the blood is pumped at a rate between 4 and 7.5 liters per minute.

179. One or more of the methods of Examples 157-161, wherein the blood is pumped at a rate between 4 and 8 liters per minute.

180. One or more of the methods of Examples 157-161, wherein the blood is pumped at a rate between 4 and 8.5 liters per minute.

181. One or more of the methods of Examples 157-161, wherein the blood is pumped at a rate between 4 and 9 liters per minute.

182. One or more of the methods of Examples 157-161, wherein the blood is pumped at a rate between 4.5 and 9 liters per minute.

183. One or more of the methods of Examples 157-161, wherein the blood is pumped at a rate between 5 and 9 liters per minute.

184. One or more of the methods of Examples 157-161, wherein the blood is pumped at a rate between 5.5 and 9 liters per minute.

185. One or more of the methods of Examples 157-161, wherein the blood is pumped at a rate between 6 and 9 liters per minute.

186. One or more of the methods of Examples 157-161, wherein the blood is pumped at a rate between 6.5 and 9 liters per minute.

187. One or more of the methods of Examples 157-161, wherein the blood is pumped at a rate between 7 and 9 liters per minute.

188. One or more of the methods of Examples 157-161, wherein the blood is pumped at a rate between 7.5 and 9 liters per minute.

189. One or more of the methods of Examples 157-161, wherein the blood is pumped at a rate between 8 and 9 liters per minute.

190. One or more of the methods of Examples 157-161, wherein the blood is pumped at a rate between 8.5 and 9 liters per minute.

191. One or more of the methods of Examples 157-190, wherein the blood is pumped in the fluid flow path at a rate of at least 4 liters per minute for a duration of at least 30 minutes.

192. One or more of the methods of Examples 157-190, wherein the blood is pumped in the fluid flow path at a rate of at least 4 liters per minute for a duration of at least 2 hours.

193. One or more of the methods of Examples 157-190, wherein the blood is pumped in the fluid flow path at a rate of at least 4 liters per minute for a duration of at least 3 hours.

194. One or more of the methods of Examples 157-190, wherein the blood is pumped in the fluid flow path at a rate of at least 4 liters per minute for a duration of at least 4 hours.

195. One or more of the methods of Examples 157-194, wherein the dialysis is performed at a rate of at least 0.55 liters per minute.

196. One or more of the methods of Examples 157-194, wherein the dialysis is performed at a rate of at least 0.6 liters per minute.

197. One or more of the methods of Examples 157-186, wherein the dialysis is performed at a rate of at least 0.65 liters per minute.

198. One or more of the methods of Examples 157-186, wherein the dialysis is performed at a rate of at least 0.7 liters per minute.

199. One or more of the methods of Examples 157-186, wherein the dialysis is performed at a rate of at least 0.75 liters per minute.

200. One or more of the methods of Examples 157-186, wherein the dialysis is performed at a rate of at least 0.8 liters per minute.

201. One or more of the methods of Examples 157-186, wherein the dialysis is performed at a rate of at least 0.85 liters per minute.

202. One or more of the methods of Examples 157-186, wherein the dialysis is performed at a rate of at least 0.9 liters per minute.

203. One or more of the methods of Examples 157-186, wherein the dialysis is performed at a rate of at least 0.95 liters per minute.

204. One or more of the methods of Examples 157-186, wherein the dialysis is performed at a rate of at least 1 liter per minute.

205. One or more of the methods of Examples 157-186, wherein the dialysis is performed at a rate of at least 1.1 liters per minute.

206. One or more of the methods of Examples 157-186, wherein the dialysis is performed at a rate of at least 1.2 liters per minute.

207. One or more of the methods of Examples 157-186, wherein the dialysis is performed at a rate of at least 1.3 liters per minute.

208. One or more of the methods of Examples 157-186, wherein the dialysis is performed at a rate of at least 1.4 liters per minute.

209. One or more of the methods of Examples 157-186, wherein the dialysis is performed at a rate of at least 1.5 liters per minute.

210. One or more of the methods of Examples 157-186, wherein the dialysis is performed at a rate of at least 1.6 liters per minute.

211. One or more of the methods of Examples 157-186, wherein the dialysis is performed at a rate of at least 1.7 liters per minute.

212. One or more of the methods of Examples 157-186, wherein the dialysis is performed at a rate of at least 1.8 liters per minute.

213. One or more of the methods of Examples 157-186, wherein the dialysis is performed at a rate of at least 1.9 liters per minute.

214. One or more of the methods of Examples 157-186, wherein the dialysis is performed at a rate of at least 2 liters per minute.

215. One or more of the methods of Examples 157-186, wherein the dialysis is performed at a rate of at least 2.1 liters per minute.

216. One or more of the methods of Examples 157-186, wherein the dialysis is performed at a rate of at least 2.2 liters per minute.

217. One or more of the methods of Examples 157-186, wherein the dialysis is performed at a rate of at least 2.3 liters per minute.

218. One or more of the methods of Examples 157-186, wherein the dialysis is performed at a rate of at least 2.4 liters per minute.

219. One or more of the methods of Examples 157-186, wherein the dialysis is performed at a rate of at least 2.5 liters per minute.

220. One or more of the methods of Examples 157-186, wherein the dialysis is performed at a rate of at least 2.6 liters per minute.

221. One or more of the methods of Examples 157-186, wherein the dialysis is performed at a rate of at least 2.7 liters per minute.

222. One or more of the methods of Examples 157-186, wherein the dialysis is performed at a rate of at least 2.8 liters per minute.

223. One or more of the methods of Examples 157-186, wherein the dialysis is performed at a rate of at least 2.9 liters per minute.

224. One or more of the methods of Examples 157-186, wherein the dialysis is performed at a rate of at least 3 liters per minute.

225. One or more of the methods of Examples 157-186, wherein the dialysis is performed at a rate between 0.5 and 0.55 liters per minute.

226. One or more of the methods of Examples 157-186, wherein the dialysis is performed at a rate between 0.5 and 0.6 liters per minute.

227. One or more of the methods of Examples 157-186, wherein the dialysis is performed at a rate between 0.5 and 0.65 liters per minute.

228. One or more of the methods of Examples 157-186, wherein the dialysis is performed at a rate between 0.5 and 0.7 liters per minute.

229. One or more of the methods of Examples 157-186, wherein the dialysis is performed at a rate between 0.5 and 0.75 liters per minute.

230. One or more of the methods of Examples 157-186, wherein the dialysis is performed at a rate between 0.5 and 0.8 liters per minute.

231. One or more of the methods of Examples 157-186, wherein the dialysis is performed at a rate between 0.5 and 0.85 liters per minute.

232. One or more of the methods of Examples 157-186, wherein the dialysis is performed at a rate between 0.5 and 0.9 liters per minute.

233. One or more of the methods of Examples 157-186, wherein the dialysis is performed at a rate between 0.5 and 0.95 liters per minute.

234. One or more of the methods of Examples 157-186, wherein the dialysis is performed at a rate between 0.5 and 1 liters per minute.

235. One or more of the methods of Examples 157-186, wherein the dialysis is performed at a rate between 0.5 and 1.1 liters per minute.

236. One or more of the methods of Examples 157-186, wherein the dialysis is performed at a rate between 0.5 and 1.2 liters per minute.

237. One or more of the methods of Examples 157-186, wherein the dialysis is performed at a rate between 0.5 and 1.3 liters per minute.

238. One or more of the methods of Examples 157-186, wherein the dialysis is performed at a rate between 0.5 and 1.4 liters per minute.

239. One or more of the methods of Examples 157-186, wherein the dialysis is performed at a rate between 0.5 and 1.5 liters per minute.

240. One or more of the methods of Examples 157-186, wherein the dialysis is performed at a rate between 0.5 and 1.6 liters per minute.

241. One or more of the methods of Examples 157-186, wherein the dialysis is performed at a rate between 0.5 and 1.7 liters per minute.

242. One or more of the methods of Examples 157-186, wherein the dialysis is performed at a rate between 0.5 and 1.8 liters per minute.

243. One or more of the methods of Examples 157-186, wherein the dialysis is performed at a rate between 0.5 and 1.9 liters per minute.

244. One or more of the methods of Examples 157-186, wherein the dialysis is performed at a rate between 0.5 and 2 liters per minute.

245. One or more of the methods of Examples 157-186, wherein the dialysis is performed at a rate between 0.5 and 2.1 liters per minute.

246. One or more of the methods of Examples 157-186, wherein the dialysis is performed at a rate between 0.5 and 2.2 liters per minute.

247. One or more of the methods of Examples 157-186, wherein the dialysis is performed at a rate between 0.5 and 2.3 liters per minute.

248. One or more of the methods of Examples 157-186, wherein the dialysis is performed at a rate between 0.5 and 2.4 liters per minute.

249. One or more of the methods of Examples 157-186, wherein the dialysis is performed at a rate between 0.5 and 2.5 liters per minute.

250. One or more of the methods of Examples 157-186, wherein the dialysis is performed at a rate between 0.5 and 2.6 liters per minute.

251. One or more of the methods of Examples 157-186, wherein the dialysis is performed at a rate between 0.5 and 2.7 liters per minute.

252. One or more of the methods of Examples 157-186, wherein the dialysis is performed at a rate between 0.5 and 2.8 liters per minute.

253. One or more of the methods of Examples 157-186, wherein the dialysis is performed at a rate between 0.5 and 2.9 liters per minute.

254. One or more of the methods of Examples 157-186, wherein the dialysis is performed at a rate between 0.5 and 3 liters per minute.

255. One or more of the methods of Examples 157-186, wherein the dialysis is performed at a rate between 0.55 and 3 liters per minute.

256. One or more of the methods of Examples 157-186, wherein the dialysis is performed at a rate between 0.6 and 3 liters per minute.

257. One or more of the methods of Examples 157-186, wherein the dialysis is performed at a rate between 0.65 and 3 liters per minute.

258. One or more of the methods of Examples 157-186, wherein the dialysis is performed at a rate between 0.7 and 3 liters per minute.

259. One or more of the methods of Examples 157-186, wherein the dialysis is performed at a rate between 0.75 and 3 liters per minute.

260. One or more of the methods of Examples 157-186, wherein the dialysis is performed at a rate between 0.8 and 3 liters per minute.

261. One or more of the methods of Examples 157-186, wherein the dialysis is performed at a rate between 0.85 and 3 liters per minute.

262. One or more of the methods of Examples 157-186, wherein the dialysis is performed at a rate between 0.9 and 3 liters per minute.

263. One or more of the methods of Examples 157-186, wherein the dialysis is performed at a rate between 0.95 and 3 liters per minute.

264. One or more of the methods of Examples 157-186, wherein the dialysis is performed at a rate between 1 and 3 liters per minute.

265. One or more of the methods of Examples 157-186, wherein the dialysis is performed at a rate between 1.1 and 3 liters per minute.

266. One or more of the methods of Examples 157-186, wherein the dialysis is performed at a rate between 1.2 and 3 liters per minute.

267. One or more of the methods of Examples 157-186, wherein the dialysis is performed at a rate between 1.3 and 3 liters per minute.

268. One or more of the methods of Examples 157-186, wherein the dialysis is performed at a rate between 1.4 and 3 liters per minute.

269. One or more of the methods of Examples 157-186, wherein the dialysis is performed at a rate between 1.5 and 3 liters per minute.

270. One or more of the methods of Examples 157-186, wherein the dialysis is performed at a rate between 1.6 and 3 liters per minute.

271. One or more of the methods of Examples 157-186, wherein the dialysis is performed at a rate between 1.7 and 3 liters per minute.

272. One or more of the methods of Examples 157-186, wherein the dialysis is performed at a rate between 1.8 and 3 liters per minute.

273. One or more of the methods of Examples 157-186, wherein the dialysis is performed at a rate between 1.9 and 3 liters per minute.

274. One or more of the methods of Examples 157-186, wherein the dialysis is performed at a rate between 2 and 3 liters per minute.

275. One or more of the methods of Examples 157-186, wherein the dialysis is performed at a rate between 2.1 and 3 liters per minute.

276. One or more of the methods of Examples 157-186, wherein the dialysis is performed at a rate between 2.2 and 3 liters per minute.

277. One or more of the methods of Examples 157-186, wherein the dialysis is performed at a rate between 2.3 and 3 liters per minute.

278. One or more of the methods of Examples 157-186, wherein the dialysis is performed at a rate between 2.4 and 3 liters per minute.

279. One or more of the methods of Examples 157-186, wherein the dialysis is performed at a rate between 2.5 and 3 liters per minute.

280. One or more of the methods of Examples 157-186, wherein the dialysis is performed at a rate between 2.6 and 3 liters per minute.

281. One or more of the methods of Examples 157-186, wherein the dialysis is performed at a rate between 2.7 and 3 liters per minute.

282. One or more of the methods of Examples 157-186, wherein the dialysis is performed at a rate between 2.8 and 3 liters per minute.

283. One or more of the methods of Examples 157-186, wherein the dialysis is performed at a rate between 2.9 and 3 liters per minute.

284. One or more of the methods of Examples 157-283, wherein performing the dialysis comprises:
   receiving at least a portion of the blood at a location on the fluid flow path downstream from one or more pumps; and
   causing blood treated with dialysis to enter the fluid flow path upstream from the one or more pumps.

285. One or more of the methods of Examples 157-284, wherein the dialysis is performed on the blood for a duration of at least 1 hour.

286. One or more of the methods of Examples 157-284, wherein the dialysis is performed on the blood for a duration of at least 2 hours.

287. One or more of the methods of Examples 157-284, wherein the dialysis is performed on the blood for a duration of at least 3 hours.

288. One or more of the methods of Examples 157-284, wherein the dialysis is performed on the blood for a duration of at least 4 hours.

289. One or more of the methods of Examples 157-284, wherein the dialysis is performed on the blood for a duration of at least 5 hours.

290. One or more of the methods of Examples 157-284, wherein the dialysis is performed on the blood for a duration of at least 6 hours.

291. One or more of the methods of Examples 157-284, wherein the dialysis is performed on the blood for a duration of at least 7 hours.

292. One or more of the methods of Examples 157-284, wherein the dialysis is performed on the blood for a duration of at least 8 hours.

293. One or more of the methods of Examples 157-284, wherein the dialysis is performed on the blood for a duration of at least 12 hours.

294. One or more of the methods of Examples 157-284, wherein the dialysis is performed on the blood for a duration of at least 16 hours.

295. One or more of the methods of Examples 157-284, wherein the dialysis is performed on the blood for a duration of at least 24 hours.

296. One or more of the methods of Examples 157-284, wherein the dialysis is performed on the blood for a duration of at least 36 hours.

297. One or more of the methods of Examples 157-297, wherein the dialysis is performed on the blood for a duration of at least 48 hours.

298. One or more of the methods of Examples 157-297, further comprising heating at least a portion of the blood from the fluid flow path to a temperature of at least 42 degrees Celsius for at least 15 minutes.

299. The method of Example 298, wherein at least a portion of the blood is heated to a temperature of at least 42.5 degrees Celsius.

300. The method of Example 297, wherein at least a portion of the blood is heated to a temperature of at least 43 degrees Celsius.

301. The method of Example 297, wherein at least a portion of the blood is heated to a temperature of at least 43.5 degrees Celsius.

302. The method of Example 297, wherein at least a portion of the blood is heated to a temperature of at least 44 degrees Celsius.

303. The method of Example 297, wherein at least a portion of the blood is heated to a temperature of at least 44.5 degrees Celsius.

304. The method of Example 297, wherein at least a portion of the blood is heated to a temperature of at least 45 degrees Celsius.

305. The method of Example 297, wherein at least a portion of the blood is heated to a temperature between 42 and 42.5 degrees Celsius.

306. The method of Example 297, wherein at least a portion of the blood is heated to a temperature between 42 and 43 degrees Celsius.

307. The method of Example 297, wherein at least a portion of the blood is heated to a temperature between 42 and 43.5 degrees Celsius.

308. The method of Example 297, wherein at least a portion of the blood is heated to a temperature between 42 and 44 degrees Celsius.

309. The method of Example 297, wherein at least a portion of the blood is heated to a temperature between 42 and 44.5 degrees Celsius.

310. The method of Example 297, wherein at least a portion of the blood is heated to a temperature between 42 and 45 degrees Celsius.

311. The method of Example 297, wherein at least a portion of the blood is heated to a temperature between 42.5 and 45 degrees Celsius.

312. The method of Example 297, wherein at least a portion of the blood is heated to a temperature between 43 and 45 degrees Celsius.

313. The method of Example 297, wherein at least a portion of the blood is heated to a temperature between 43.5 and 45 degrees Celsius.

314. The method of Example 297, wherein at least a portion of the blood is heated to a temperature between 44 and 45 degrees Celsius.

315. The method of Example 297, wherein at least a portion of the blood is heated to a temperature between 44.5 and 45 degrees Celsius.

316. One or more of the methods of Examples 157-315, further comprising removing carbon dioxide from at least a portion of the blood.

317. One or more of the methods of Examples 157-316, further comprising adding oxygen to at least a portion of the blood.

318. The method of Example 316, wherein removing carbon dioxide from at least a portion of the blood comprises causing the blood to flow through at least one membrane.

319. The method of Example 318, wherein the at least one membrane collectively has an effective surface area greater than 1.8 square meters.

320. One or more of the methods of Examples 316-319, wherein carbon dioxide is removed from at least a portion of the blood for at least 30 minutes.

321. One or more of the methods of Examples 316-319, wherein carbon dioxide is removed from at least a portion of the blood for at least 1 hour.

322. One or more of the methods of Examples 316-319, wherein carbon dioxide is removed from at least a portion of the blood for at least 1.5 hours.

323. One or more of the methods of Examples 316-319, wherein carbon dioxide is removed from at least a portion of the blood for at least 2 hours.

324. One or more of the methods of Examples 316-319, wherein carbon dioxide is removed from at least a portion of the blood for at least 2.5 hours.

325. One or more of the methods of Examples 316-319, wherein carbon dioxide is removed from at least a portion of the blood for at least 3 hours.

326. One or more of the methods of Examples 316-319, wherein carbon dioxide is removed from at least a portion of the blood for at least 3.5 hours.

327. One or more of the methods of Examples 316-319, wherein carbon dioxide is removed from at least a portion of the blood for at least 4 hours.

328. One or more of the methods of Examples 316-319, wherein carbon dioxide is removed from at least a portion of the blood for at least 4.5 hours.

329. One or more of the methods of Examples 316-319, wherein carbon dioxide is removed from at least a portion of the blood for at least 5 hours.

330. One or more of the methods of Examples 316-319, wherein carbon dioxide is removed from at least a portion of the blood for at least 5.5 hours.

331. One or more of the methods of Examples 316-319, wherein carbon dioxide is removed from at least a portion of the blood for at least 6 hours.

332. One or more of the methods of Examples 316-319, wherein carbon dioxide is removed from at least a portion of the blood for at least 6.5 hours.

333. One or more of the methods of Examples 316-319, wherein carbon dioxide is removed from at least a portion of the blood for at least 7 hours.

334. One or more of the methods of Examples 316-319, wherein carbon dioxide is removed from at least a portion of the blood for at least 7.5 hours.

335. One or more of the methods of Examples 316-319, wherein carbon dioxide is removed from at least a portion of the blood for at least 8 hours.

336. One or more of the methods of Examples 298-335, wherein at least a portion of the blood is heated to a temperature of at least 42 degrees Celsius for at least 30 minutes.

337. One or more of the methods of Examples 298-335, wherein at least a portion of the blood is heated to a temperature of at least 42 degrees Celsius for at least 1 hour.

338. One or more of the methods of Examples 298-335, wherein at least a portion of the blood is heated to a temperature of at least 42 degrees Celsius for at least 1.5 hours.

339. One or more of the methods of Examples 298-335, wherein at least a portion of the blood is heated to a temperature of at least 42 degrees Celsius for at least 2 hours.

340. One or more of the methods of Examples 298-335, wherein at least a portion of the blood is heated to a temperature of at least 42 degrees Celsius for at least 2.5 hours.

341. One or more of the methods of Examples 298-335, wherein at least a portion of the blood is heated to a temperature of at least 42 degrees Celsius for at least 3 hours.

342. One or more of the methods of Examples 298-335, wherein at least a portion of the blood is heated to a temperature of at least 42 degrees Celsius for at least 3.5 hours.

343. One or more of the methods of Examples 298-335, wherein at least a portion of the blood is heated to a temperature of at least 42 degrees Celsius for at least 4 hours.

344. One or more of the methods of Examples 298-335, wherein at least a portion of the blood is heated to a temperature of at least 42 degrees Celsius for at least 4.5 hours.

345. One or more of the methods of Examples 298-335, wherein at least a portion of the blood is heated to a temperature of at least 42 degrees Celsius for at least 5 hours.

346. One or more of the methods of Examples 298-335, wherein at least a portion of the blood is heated to a temperature of at least 42 degrees Celsius for at least 5.5 hours.

347. One or more of the methods of Examples 298-335, wherein at least a portion of the blood is heated to a temperature of at least 42 degrees Celsius for at least 6 hours.

348. One or more of the methods of Examples 157-347, further comprising adding a substance to at least a portion of the blood that facilitates the production of reactive oxygen species within the blood.

349. The method of Example 348, wherein the substance comprises a free radical.

350. The method of Example 348, wherein the substance comprises an unstable substance.

351. The method of Example 348, wherein the substance comprises ozone.

352. The method of Example 348, wherein the substance comprises Freon.

353. The method of Example 348, wherein the substance comprises iron.

354. The method of Example 348, wherein the substance comprises copper.

355. The method of Example 348, wherein the substance comprises ozone and iron.

356. The method of Example 348, wherein the substance comprises ozone and copper.

357. A system comprising:
one or more heat exchangers coupled to a fluid flow path and configured to heat at least a portion of blood from the fluid flow path to a temperature of at least 42 degrees Celsius; and
one or more venting modules coupled to the fluid flow path, the one or more venting modules configured to remove carbon dioxide from at least a portion of the blood.

358. The system of Example 357, wherein the one or more venting modules are configured to add oxygen to at least a portion of the blood.

359. The system of Example 357, wherein the one or more venting modules are configured to cause at least a portion of the blood to flow through at least one membrane.

360. The system of Example 359, wherein the at least one membrane collectively has an effective surface area greater than 1.8 square meters.

361. One or more of the systems of Examples 357-360, further comprising an oxygenator coupled to the fluid flow path, the oxygenator configured to cause oxygen to be added to at least a portion of the blood.

362. One or more of the systems of Examples 357-361, further comprising a reintroduction module coupled to the fluid flow path and configured to add a substance to at least a portion of the blood that facilitates the production of reactive oxygen species within the blood.

363. The system of Example 362, wherein the substance comprises a free radical.

364. The system of Example 362, wherein the substance comprises an unstable substance.

365. The system of Example 362, wherein the substance comprises ozone.

366. The system of Example 362, wherein the substance comprises Freon.

367. The system of Example 362, wherein the substance comprises iron.

368. The system of Example 362, wherein the substance comprises copper.

369. The system of Example 362, wherein the substance comprises ozone and iron.

370. The system of Example 362, wherein the substance comprises ozone and copper.

371. One or more of the systems of Examples 357-370, wherein the one or more heat exchangers are configured to heat at least a portion of the blood to a temperature of at least 42.5 degrees Celsius.

372. One or more of the systems of Examples 357-370, wherein the one or more heat exchangers are configured to heat at least a portion of the blood to a temperature of at least 43 degrees Celsius.

373. One or more of the systems of Examples 357-370, wherein the one or more heat exchangers are configured to heat at least a portion of the blood to a temperature of at least 43.5 degrees Celsius.

374. One or more of the systems of Examples 357-370, wherein the one or more heat exchangers are configured to heat at least a portion of the blood to a temperature of at least 44 degrees Celsius.

375. One or more of the systems of Examples 357-370, wherein the one or more heat exchangers are configured to heat at least a portion of the blood to a temperature of at least 44.5 degrees Celsius.

376. One or more of the systems of Examples 357-370, wherein the one or more heat exchangers are configured to heat at least a portion of the blood to a temperature of at least 45 degrees Celsius.

377. One or more of the systems of Examples 357-370, wherein the one or more heat exchangers are configured to heat at least a portion of the blood to a temperature between 42 and 42.5 degrees Celsius.

378. One or more of the systems of Examples 357-370, wherein the one or more heat exchangers are configured to heat at least a portion of the blood to a temperature between 42 and 43 degrees Celsius.

379. One or more of the systems of Examples 357-370, wherein the one or more heat exchangers are configured to heat at least a portion of the blood to a temperature between 42 and 43.5 degrees Celsius.

380. One or more of the systems of Examples 357-370, wherein the one or more heat exchangers are configured to heat at least a portion of the blood to a temperature between 42 and 44 degrees Celsius.

381. One or more of the systems of Examples 357-370, wherein the one or more heat exchangers are configured to heat at least a portion of the blood to a temperature between 42 and 44.5 degrees Celsius.

382. One or more of the systems of Examples 357-370, wherein the one or more heat exchangers are configured to heat at least a portion of the blood to a temperature between 42 and 45 degrees Celsius.

383. One or more of the systems of Examples 357-370, wherein the one or more heat exchangers are configured to heat at least a portion of the blood to a temperature between 42.5 and 45 degrees Celsius.

384. One or more of the systems of Examples 357-370, wherein the one or more heat exchangers are configured to heat at least a portion of the blood to a temperature between 43 and 45 degrees Celsius.

385. One or more of the systems of Examples 357-370, wherein the one or more heat exchangers are configured to heat at least a portion of the blood to a temperature between 43.5 and 45 degrees Celsius.

386. One or more of the systems of Examples 357-370, wherein the one or more heat exchangers are configured to heat at least a portion of the blood to a temperature between 44 and 45 degrees Celsius.

387. One or more of the systems of Examples 357-370, wherein the one or more heat exchangers are configured to heat at least a portion of the blood to a temperature between 44.5 and 45 degrees Celsius.

388. One or more of the systems of Examples 357-387, further comprising one or more dialysis modules coupled to the fluid flow path and configured to perform dialysis on at least a portion of the blood at a collective rate of at least 0.5 liters per minute.

389. The system of Example 388, wherein the one or more dialysis modules are configured to perform convection dialysis.

390. The system of Example 388, wherein the one or more dialysis modules are configured to perform diffusion dialysis.

391. One or more of the systems of Examples 357-390, further comprising a reintroduction module coupled to the fluid flow path and configured to add electrolyte-balanced fluid to at least a portion of the blood at a rate of at least 7 liters per hour.

392. The system of Example 391, wherein the electrolyte-balanced fluid is at a temperature of at least 35 degrees Celsius.

393. One or more of the systems of Examples 388-390, wherein the one or more dialysis modules are configured to perform dialysis on at least a portion of the blood at a collective rate of at least 0.55 liters per minute.

394. One or more of the systems of Examples 388-390, wherein the one or more dialysis modules are configured to perform dialysis on at least a portion of the blood at a collective rate of at least 0.6 liters per minute.

395. One or more of the systems of Examples 388-390, wherein the one or more dialysis modules are configured to perform dialysis on at least a portion of the blood at a collective rate of at least 0.65 liters per minute.

396. One or more of the systems of Examples 388-390, wherein the one or more dialysis modules are configured to perform dialysis on at least a portion of the blood at a collective rate of at least 0.7 liters per minute.

397. One or more of the systems of Examples 388-390, wherein the one or more dialysis modules are configured to perform dialysis on at least a portion of the blood at a collective rate of at least 0.75 liters per minute.

398. One or more of the systems of Examples 388-390, wherein the one or more dialysis modules are configured to perform dialysis on at least a portion of the blood at a collective rate of at least 0.8 liters per minute.

399. One or more of the systems of Examples 388-390, wherein the one or more dialysis modules are configured to perform dialysis on at least a portion of the blood at a collective rate of at least 0.85 liters per minute.

400. One or more of the systems of Examples 388-390, wherein the one or more dialysis modules are configured to perform dialysis on at least a portion of the blood at a collective rate of at least 0.9 liters per minute.

401. One or more of the systems of Examples 388-390, wherein the one or more dialysis modules are configured to perform dialysis on at least a portion of the blood at a collective rate of at least 0.95 liters per minute.

402. One or more of the systems of Examples 388-390, wherein the one or more dialysis modules are configured to perform dialysis on at least a portion of the blood at a collective rate of at least 1 liter per minute.

403. One or more of the systems of Examples 388-390, wherein the one or more dialysis modules are configured to perform dialysis on at least a portion of the blood at a collective rate of at least 1.1 liters per minute.

404. One or more of the systems of Examples 388-390, wherein the one or more dialysis modules are configured to perform dialysis on at least a portion of the blood at a collective rate of at least 1.2 liters per minute.

405. One or more of the systems of Examples 388-390, wherein the one or more dialysis modules are configured to perform dialysis on at least a portion of the blood at a collective rate of at least 1.3 liters per minute.

406. One or more of the systems of Examples 388-390, wherein the one or more dialysis modules are configured to perform dialysis on at least a portion of the blood at a collective rate of at least 1.4 liters per minute.

407. One or more of the systems of Examples 388-390, wherein the one or more dialysis modules are configured to perform dialysis on at least a portion of the blood at a collective rate of at least 1.5 liters per minute.

408. One or more of the systems of Examples 388-390, wherein the one or more dialysis modules are configured to perform dialysis on at least a portion of the blood at a collective rate of at least 1.6 liters per minute.

409. One or more of the systems of Examples 388-390, wherein the one or more dialysis modules are configured to perform dialysis on at least a portion of the blood at a collective rate of at least 1.7 liters per minute.

410. One or more of the systems of Examples 388-390, wherein the one or more dialysis modules are configured to perform dialysis on at least a portion of the blood at a collective rate of at least 1.8 liters per minute.

411. One or more of the systems of Examples 388-390, wherein the one or more dialysis modules are configured to perform dialysis on at least a portion of the blood at a collective rate of at least 1.9 liters per minute.

412. One or more of the systems of Examples 388-390, wherein the one or more dialysis modules are configured to perform dialysis on at least a portion of the blood at a collective rate of at least 2 liters per minute.

413. One or more of the systems of Examples 388-390, wherein the one or more dialysis modules are configured to perform dialysis on at least a portion of the blood at a collective rate of at least 2.1 liters per minute.

414. One or more of the systems of Examples 388-390, wherein the one or more dialysis modules are configured to perform dialysis on at least a portion of the blood at a collective rate of at least 2.2 liters per minute.

415. One or more of the systems of Examples 388-390, wherein the one or more dialysis modules are configured to perform dialysis on at least a portion of the blood at a collective rate of at least 2.3 liters per minute.

416. One or more of the systems of Examples 388-390, wherein the one or more dialysis modules are configured to perform dialysis on at least a portion of the blood at a collective rate of at least 2.4 liters per minute.

417. One or more of the systems of Examples 388-390, wherein the one or more dialysis modules are configured to perform dialysis on at least a portion of the blood at a collective rate of at least 2.5 liters per minute.

418. One or more of the systems of Examples 388-390, wherein the one or more dialysis modules are configured to perform dialysis on at least a portion of the blood at a collective rate of at least 2.6 liters per minute.

419. One or more of the systems of Examples 388-390, wherein the one or more dialysis modules are configured to perform dialysis on at least a portion of the blood at a collective rate of at least 2.7 liters per minute.

420. One or more of the systems of Examples 388-390, wherein the one or more dialysis modules are configured to perform dialysis on at least a portion of the blood at a collective rate of at least 2.8 liters per minute.

421. One or more of the systems of Examples 388-390, wherein the one or more dialysis modules are configured to perform dialysis on at least a portion of the blood at a collective rate of at least 2.9 liters per minute.

422. One or more of the systems of Examples 388-390, wherein the one or more dialysis modules are configured to perform dialysis on at least a portion of the blood at a collective rate of at least 3 liters per minute.

423. One or more of the systems of Examples 388-390, wherein the one or more dialysis modules are configured to perform dialysis on at least a portion of the blood at a collective rate between 0.5 and 0.55 liters per minute.

424. One or more of the systems of Examples 388-390, wherein the one or more dialysis modules are configured to perform dialysis on at least a portion of the blood at a collective rate between 0.5 and 0.6 liters per minute.

425. One or more of the systems of Examples 388-390, wherein the one or more dialysis modules are configured to perform dialysis on at least a portion of the blood at a collective rate between 0.5 and 0.65 liters per minute.

426. One or more of the systems of Examples 388-390, wherein the one or more dialysis modules are configured to perform dialysis on at least a portion of the blood at a collective rate between 0.5 and 0.7 liters per minute.

427. One or more of the systems of Examples 388-390, wherein the one or more dialysis modules are configured to perform dialysis on at least a portion of the blood at a collective rate between 0.5 and 0.75 liters per minute.

428. One or more of the systems of Examples 388-390, wherein the one or more dialysis modules are configured to perform dialysis on at least a portion of the blood at a collective rate between 0.5 and 0.8 liters per minute.

429. One or more of the systems of Examples 388-390, wherein the one or more dialysis modules are configured to perform dialysis on at least a portion of the blood at a collective rate between 0.5 and 0.85 liters per minute.

430. One or more of the systems of Examples 388-390, wherein the one or more dialysis modules are configured to perform dialysis on at least a portion of the blood at a collective rate between 0.5 and 0.9 liters per minute.

431. One or more of the systems of Examples 388-390, wherein the one or more dialysis modules are configured to perform dialysis on at least a portion of the blood at a collective rate between 0.5 and 0.95 liters per minute.

432. One or more of the systems of Examples 388-390, wherein the one or more dialysis modules are configured to perform dialysis on at least a portion of the blood at a collective rate between 0.5 and 1 liters per minute.

433. One or more of the systems of Examples 388-390, wherein the one or more dialysis modules are configured to perform dialysis on at least a portion of the blood at a collective rate between 0.5 and 1.1 liters per minute.

434. One or more of the systems of Examples 388-390, wherein the one or more dialysis modules are configured to perform dialysis on at least a portion of the blood at a collective rate between 0.5 and 1.2 liters per minute.

435. One or more of the systems of Examples 388-390, wherein the one or more dialysis modules are configured to perform dialysis on at least a portion of the blood at a collective rate between 0.5 and 1.3 liters per minute.

436. One or more of the systems of Examples 388-390, wherein the one or more dialysis modules are configured to perform dialysis on at least a portion of the blood at a collective rate between 0.5 and 1.4 liters per minute.

437. One or more of the systems of Examples 388-390, wherein the one or more dialysis modules are configured to perform dialysis on at least a portion of the blood at a collective rate between 0.5 and 1.5 liters per minute.

438. One or more of the systems of Examples 388-390, wherein the one or more dialysis modules are configured to perform dialysis on at least a portion of the blood at a collective rate between 0.5 and 1.6 liters per minute.

439. One or more of the systems of Examples 388-390, wherein the one or more dialysis modules are configured to perform dialysis on at least a portion of the blood at a collective rate between 0.5 and 1.7 liters per minute.

440. One or more of the systems of Examples 388-390, wherein the one or more dialysis modules are configured to perform dialysis on at least a portion of the blood at a collective rate between 0.5 and 1.8 liters per minute.

441. One or more of the systems of Examples 388-390, wherein the one or more dialysis modules are configured to perform dialysis on at least a portion of the blood at a collective rate between 0.5 and 1.9 liters per minute.

442. One or more of the systems of Examples 388-390, wherein the one or more dialysis modules are configured to perform dialysis on at least a portion of the blood at a collective rate between 0.5 and 2 liters per minute.

443. One or more of the systems of Examples 388-390, wherein the one or more dialysis modules are configured to perform dialysis on at least a portion of the blood at a collective rate between 0.5 and 2.1 liters per minute.

444. One or more of the systems of Examples 388-390, wherein the one or more dialysis modules are configured to perform dialysis on at least a portion of the blood at a collective rate between 0.5 and 2.2 liters per minute.

445. One or more of the systems of Examples 388-390, wherein the one or more dialysis modules are configured to perform dialysis on at least a portion of the blood at a collective rate between 0.5 and 2.3 liters per minute.

446. One or more of the systems of Examples 388-390, wherein the one or more dialysis modules are configured to perform dialysis on at least a portion of the blood at a collective rate between 0.5 and 2.4 liters per minute.

447. One or more of the systems of Examples 388-390, wherein the one or more dialysis modules are configured to perform dialysis on at least a portion of the blood at a collective rate between 0.5 and 2.5 liters per minute.

448. One or more of the systems of Examples 388-390, wherein the one or more dialysis modules are configured to perform dialysis on at least a portion of the blood at a collective rate between 0.5 and 2.6 liters per minute.

449. One or more of the systems of Examples 388-390, wherein the one or more dialysis modules are configured to perform dialysis on at least a portion of the blood at a collective rate between 0.5 and 2.7 liters per minute.

450. One or more of the systems of Examples 388-390, wherein the one or more dialysis modules are configured to perform dialysis on at least a portion of the blood at a collective rate between 0.5 and 2.8 liters per minute.

451. One or more of the systems of Examples 388-390, wherein the one or more dialysis modules are configured to perform dialysis on at least a portion of the blood at a collective rate between 0.5 and 2.9 liters per minute.

452. One or more of the systems of Examples 388-390, wherein the one or more dialysis modules are configured to perform dialysis on at least a portion of the blood at a collective rate between 0.5 and 3 liters per minute.

453. One or more of the systems of Examples 388-390, wherein the one or more dialysis modules are configured to perform dialysis on at least a portion of the blood at a collective rate between 0.55 and 3 liters per minute.

454. One or more of the systems of Examples 388-390, wherein the one or more dialysis modules are configured to perform dialysis on at least a portion of the blood at a collective rate between 0.6 and 3 liters per minute.

455. One or more of the systems of Examples 388-390, wherein the one or more dialysis modules are configured to perform dialysis on at least a portion of the blood at a collective rate between 0.65 and 3 liters per minute.

456. One or more of the systems of Examples 388-390, wherein the one or more dialysis modules are configured to perform dialysis on at least a portion of the blood at a collective rate between 0.7 and 3 liters per minute.

457. One or more of the systems of Examples 388-390, wherein the one or more dialysis modules are configured to perform dialysis on at least a portion of the blood at a collective rate between 0.75 and 3 liters per minute.

458. One or more of the systems of Examples 388-390, wherein the one or more dialysis modules are configured to perform dialysis on at least a portion of the blood at a collective rate between 0.8 and 3 liters per minute.

459. One or more of the systems of Examples 388-390, wherein the one or more dialysis modules are configured to perform dialysis on at least a portion of the blood at a collective rate between 0.85 and 3 liters per minute.

460. One or more of the systems of Examples 388-390, wherein the one or more dialysis modules are configured to perform dialysis on at least a portion of the blood at a collective rate between 0.9 and 3 liters per minute.

461. One or more of the systems of Examples 388-390, wherein the one or more dialysis modules are configured to perform dialysis on at least a portion of the blood at a collective rate between 0.95 and 3 liters per minute.

462. One or more of the systems of Examples 388-390, wherein the one or more dialysis modules are configured to perform dialysis on at least a portion of the blood at a collective rate between 1 and 3 liters per minute.

463. One or more of the systems of Examples 388-390, wherein the one or more dialysis modules are configured to perform dialysis on at least a portion of the blood at a collective rate between 1.1 and 3 liters per minute.

464. One or more of the systems of Examples 388-390, wherein the one or more dialysis modules are configured to perform dialysis on at least a portion of the blood at a collective rate between 1.2 and 3 liters per minute.

465. One or more of the systems of Examples 388-390, wherein the one or more dialysis modules are configured to perform dialysis on at least a portion of the blood at a collective rate between 1.3 and 3 liters per minute.

466. One or more of the systems of Examples 388-390, wherein the one or more dialysis modules are configured to perform dialysis on at least a portion of the blood at a collective rate between 1.4 and 3 liters per minute.

467. One or more of the systems of Examples 388-390, wherein the one or more dialysis modules are configured to perform dialysis on at least a portion of the blood at a collective rate between 1.5 and 3 liters per minute.

468. One or more of the systems of Examples 388-390, wherein the one or more dialysis modules are configured to perform dialysis on at least a portion of the blood at a collective rate between 1.6 and 3 liters per minute.

469. One or more of the systems of Examples 388-390, wherein the one or more dialysis modules are configured to perform dialysis on at least a portion of the blood at a collective rate between 1.7 and 3 liters per minute.

470. One or more of the systems of Examples 388-390, wherein the one or more dialysis modules are configured to perform dialysis on at least a portion of the blood at a collective rate between 1.8 and 3 liters per minute.

471. One or more of the systems of Examples 388-390, wherein the one or more dialysis modules are configured to perform dialysis on at least a portion of the blood at a collective rate between 1.9 and 3 liters per minute.

472. One or more of the systems of Examples 388-390, wherein the one or more dialysis modules are configured to perform dialysis on at least a portion of the blood at a collective rate between 2 and 3 liters per minute.

473. One or more of the systems of Examples 388-390, wherein the one or more dialysis modules are configured to perform dialysis on at least a portion of the blood at a collective rate between 2.1 and 3 liters per minute.

474. One or more of the systems of Examples 388-390, wherein the one or more dialysis modules are configured to perform dialysis on at least a portion of the blood at a collective rate between 2.2 and 3 liters per minute.

475. One or more of the systems of Examples 388-390, wherein the one or more dialysis modules are configured to perform dialysis on at least a portion of the blood at a collective rate between 2.3 and 3 liters per minute.

476. One or more of the systems of Examples 388-390, wherein the one or more dialysis modules are configured to perform dialysis on at least a portion of the blood at a collective rate between 2.4 and 3 liters per minute.

477. One or more of the systems of Examples 388-390, wherein the one or more dialysis modules are configured to perform dialysis on at least a portion of the blood at a collective rate between 2.5 and 3 liters per minute.

478. One or more of the systems of Examples 388-390, wherein the one or more dialysis modules are configured to perform dialysis on at least a portion of the blood at a collective rate between 2.6 and 3 liters per minute.

479. One or more of the systems of Examples 388-390, wherein the one or more dialysis modules are configured to perform dialysis on at least a portion of the blood at a collective rate between 2.7 and 3 liters per minute.

480. One or more of the systems of Examples 388-390, wherein the one or more dialysis modules are configured to perform dialysis on at least a portion of the blood at a collective rate between 2.8 and 3 liters per minute.

481. One or more of the systems of Examples 388-390, wherein the one or more dialysis modules are configured to perform dialysis on at least a portion of the blood at a collective rate between 2.9 and 3 liters per minute.

482. One or more of the systems of Examples 388-481, wherein:
the one or more dialysis modules are configured to receive blood at a location on the fluid flow path downstream from one or more pumps; and
the one or more dialysis modules are configured to cause blood treated with dialysis to enter the fluid flow path upstream from the one or more pumps.

483. One or more of the systems of Examples 357-482, further comprising one or more pumps configured to pump the blood in the fluid flow path at a collective rate of at least 4 liters per minute.

484. The system of Example 483, wherein the one or more pumps are configured to pump the blood at a collective rate of at least 4.5 liters per minute.

485. The system of Example 483, wherein the one or more pumps are configured to pump the blood at a collective rate of at least 5 liters per minute.

486. The system of Example 483, wherein the one or more pumps are configured to pump the blood at a collective rate of at least 5.5 liters per minute.

487. The system of Example 483, wherein the one or more pumps are configured to pump the blood at a collective rate of at least 6 liters per minute.

488. The system of Example 483, wherein the one or more pumps are configured to pump the blood at a collective rate of at least 6.5 liters per minute.

489. The system of Example 483, wherein the one or more pumps are configured to pump the blood at a collective rate of at least 7 liters per minute.

490. The system of Example 483, wherein the one or more pumps are configured to pump the blood at a collective rate of at least 7.5 liters per minute.

491. The system of Example 483, wherein the one or more pumps are configured to pump the blood at a collective rate of at least 8 liters per minute.

492. The system of Example 483, wherein the one or more pumps are configured to pump the blood at a collective rate of at least 8.5 liters per minute.

493. The system of Example 483, wherein the one or more pumps are configured to pump the blood at a collective rate of at least 9 liters per minute.

494. The system of Example 483, wherein the one or more pumps are configured to pump the blood at a collective rate between 4 and 4.5 liters per minute.

495. The system of Example 483, wherein the one or more pumps are configured to pump the blood at a collective rate between 4 and 5 liters per minute.

496. The system of Example 483, wherein the one or more pumps are configured to pump the blood at a collective rate between 4 and 5.5 liters per minute.

497. The system of Example 483, wherein the one or more pumps are configured to pump the blood at a collective rate between 4 and 6 liters per minute.

498. The system of Example 483, wherein the one or more pumps are configured to pump the blood at a collective rate between 4 and 6.5 liters per minute.

499. The system of Example 483, wherein the one or more pumps are configured to pump the blood at a collective rate between 4 and 7 liters per minute.

500. The system of Example 483, wherein the one or more pumps are configured to pump the blood at a collective rate between 4.5 and 9 liters per minute.

501. The system of Example 483, wherein the one or more pumps are configured to pump the blood at a collective rate between 5 and 9 liters per minute.

502. The system of Example 483, wherein the one or more pumps are configured to pump the blood at a collective rate between 5.5 and 9 liters per minute.

503. The system of Example 483, wherein the one or more pumps are configured to pump the blood at a collective rate between 6 and 9 liters per minute.

504. The system of Example 483, wherein the one or more pumps are configured to pump the blood at a collective rate between 6.5 and 9 liters per minute.

505. The system of Example 483, wherein the one or more pumps are configured to pump the blood at a collective rate between 7 and 9 liters per minute.

506. The system of Example 483, wherein the one or more pumps are configured to pump the blood at a collective rate between 7.5 and 9 liters per minute.

507. The system of Example 483, wherein the one or more pumps are configured to pump the blood at a collective rate between 8 and 9 liters per minute.

508. The system of Example 483, wherein the one or more pumps are configured to pump the blood at a collective rate between 8.5 and 9 liters per minute.

509. A method comprising:
heating at least a portion of blood from a fluid flow path to a temperature of at least 42 degrees Celsius for at least 15 minutes; and
removing carbon dioxide from at least a portion of the blood.

510. The method of Example 509, wherein at least a portion of the blood is heated to a temperature of at least 42.5 degrees Celsius.

511. The method of Example 509, wherein at least a portion of the blood is heated to a temperature of at least 43 degrees Celsius.

512. The method of Example 509, wherein at least a portion of the blood is heated to a temperature of at least 43.5 degrees Celsius.

513. The method of Example 509, wherein at least a portion of the blood is heated to a temperature of at least 44 degrees Celsius.

514. The method of Example 509, wherein at least a portion of the blood is heated to a temperature of at least 44.5 degrees Celsius.

515. The method of Example 509, wherein at least a portion of the blood is heated to a temperature of at least 45 degrees Celsius.

516. The method of Example 509, wherein at least a portion of the blood is heated to a temperature between 42 and 42.5 degrees Celsius.

517. The method of Example 509, wherein at least a portion of the blood is heated to a temperature between 42 and 43 degrees Celsius.

518. The method of Example 509, wherein at least a portion of the blood is heated to a temperature between 42 and 43.5 degrees Celsius.

519. The method of Example 509, wherein at least a portion of the blood is heated to a temperature between 42 and 44 degrees Celsius.

520. The method of Example 509, wherein at least a portion of the blood is heated to a temperature between 42 and 44.5 degrees Celsius.

521. The method of Example 509, wherein at least a portion of the blood is heated to a temperature between 42 and 45 degrees Celsius.

522. The method of Example 509, wherein at least a portion of the blood is heated to a temperature between 42.5 and 45 degrees Celsius.

523. The method of Example 509, wherein at least a portion of the blood is heated to a temperature between 43 and 45 degrees Celsius.

524. The method of Example 509, wherein at least a portion of the blood is heated to a temperature between 43.5 and 45 degrees Celsius.

525. The method of Example 509, wherein at least a portion of the blood is heated to a temperature between 44 and 45 degrees Celsius.

526. The method of Example 509, wherein at least a portion of the blood is heated to a temperature between 44.5 and 45 degrees Celsius.

527. One or more of the methods of Examples 509-526, further comprising adding oxygen to at least a portion of the blood.

528. One or more of the methods of Examples 509-527, wherein removing carbon dioxide from at least a portion of the blood comprises causing at least a portion of the blood to flow through at least one membrane.

529. The method of Example 528, wherein the at least one membrane collectively has an effective surface area greater than 1.8 square meters.

530. One or more of the methods of Examples 509-529, wherein carbon dioxide is removed from at least a portion of the blood for at least 30 minutes.

531. One or more of the methods of Examples 509-529, wherein carbon dioxide is removed from at least a portion of the blood for at least 1 hour.

532. One or more of the methods of Examples 509-529, wherein carbon dioxide is removed from at least a portion of the blood for at least 1.5 hours.

533. One or more of the methods of Examples 509-529, wherein carbon dioxide is removed from at least a portion of the blood for at least 2 hours.

534. One or more of the methods of Examples 509-529, wherein carbon dioxide is removed from at least a portion of the blood for at least 2.5 hours.

535. One or more of the methods of Examples 509-529, wherein carbon dioxide is removed from at least a portion of the blood for at least 3 hours.

536. One or more of the methods of Examples 509-529, wherein carbon dioxide is removed from at least a portion of the blood for at least 3.5 hours.

537. One or more of the methods of Examples 509-529, wherein carbon dioxide is removed from at least a portion of the blood for at least 4 hours.

538. One or more of the methods of Examples 509-529, wherein carbon dioxide is removed from at least a portion of the blood for at least 4.5 hours.

539. One or more of the methods of Examples 509-529, wherein carbon dioxide is removed from at least a portion of the blood for at least 5 hours.

540. One or more of the methods of Examples 509-529, wherein carbon dioxide is removed from at least a portion of the blood for at least 5.5 hours.

541. One or more of the methods of Examples 509-529, wherein carbon dioxide is removed from at least a portion of the blood for at least 6 hours.

542. One or more of the methods of Examples 509-529, wherein carbon dioxide is removed from at least a portion of the blood for at least 6.5 hours.

543. One or more of the methods of Examples 509-529, wherein carbon dioxide is removed from at least a portion of the blood for at least 7 hours.

544. One or more of the methods of Examples 509-529, wherein carbon dioxide is removed from at least a portion of the blood for at least 7.5 hours.

545. One or more of the methods of Examples 509-529, wherein carbon dioxide is removed from at least a portion of the blood for at least 8 hours.

546. One or more of the methods of Examples 509-545, wherein at least a portion of the blood is heated to a temperature of at least 42 degrees Celsius for at least 30 minutes.

547. One or more of the methods of Examples 509-545, wherein at least a portion of the blood is heated to a temperature of at least 42 degrees Celsius for at least 1 hour.

548. One or more of the methods of Examples 509-545, wherein at least a portion of the blood is heated to a temperature of at least 42 degrees Celsius for at least 1.5 hours.

549. One or more of the methods of Examples 509-545, wherein at least a portion of the blood is heated to a temperature of at least 42 degrees Celsius for at least 2 hours.

550. One or more of the methods of Examples 509-545, wherein at least a portion of the blood is heated to a temperature of at least 42 degrees Celsius for at least 2.5 hours.

551. One or more of the methods of Examples 509-545, wherein at least a portion of the blood is heated to a temperature of at least 42 degrees Celsius for at least 3 hours.

552. One or more of the methods of Examples 509-545, wherein at least a portion of the blood is heated to a temperature of at least 42 degrees Celsius for at least 3.5 hours.

553. One or more of the methods of Examples 509-545, wherein at least a portion of the blood is heated to a temperature of at least 42 degrees Celsius for at least 4 hours.

554. One or more of the methods of Examples 509-545, wherein at least a portion of the blood is heated to a temperature of at least 42 degrees Celsius for at least 4.5 hours.

555. One or more of the methods of Examples 509-545, wherein at least a portion of the blood is heated to a temperature of at least 42 degrees Celsius for at least 5 hours.

556. One or more of the methods of Examples 509-545, wherein at least a portion of the blood is heated to a temperature of at least 42 degrees Celsius for at least 5.5 hours.

557. One or more of the methods of Examples 509-529, wherein at least a portion of the blood is heated to a temperature of at least 42 degrees Celsius for at least 6 hours.

558. One or more of the methods of Examples 509-557, further comprising adding a substance to at least a portion of the blood that facilitates the production of reactive oxygen species within the blood.

559. The method of Example 558, wherein the substance comprises a free radical.

560. The method of Example 558, wherein the substance comprises an unstable substance.

561. The method of Example 558, wherein the substance comprises ozone.

562. The method of Example 558, wherein the substance comprises Freon.

563. The method of Example 558, wherein the substance comprises iron.

564. The method of Example 558, wherein the substance comprises copper.

565. The method of Example 558, wherein the substance comprises ozone and iron.

566. The method of Example 558, wherein the substance comprises ozone and copper.

567. One or more of the methods of Examples 509-566, further comprising pumping blood in the fluid flow path at a rate of at least 4 liters per minute.

568. The method of Example 567, wherein the blood is pumped at a rate of at least 4.5 liters per minute.

569. The method of Example 567, wherein the blood is pumped at a rate of at least 5 liters per minute.

570. The method of Example 567, wherein the blood is pumped at a rate of at least 5.5 liters per minute.

571. The method of Example 567, wherein the blood is pumped at a rate of at least 6 liters per minute.

572. The method of Example 567, wherein the blood is pumped at a rate of at least 6.5 liters per minute.

573. The method of Example 567, wherein the blood is pumped at a rate of at least 7 liters per minute.

574. The method of Example 567, wherein the blood is pumped at a rate of at least 7.5 liters per minute.

575. The method of Example 567, wherein the blood is pumped at a rate of at least 8 liters per minute.

576. The method of Example 567, wherein the blood is pumped at a rate of at least 8.5 liters per minute.

577. The method of Example 567, wherein the blood is pumped at a rate of at least 9 liters per minute.

578. The method of Example 567, wherein the blood is pumped at a rate between 4 and 4.5 liters per minute.

579. The method of Example 567, wherein the blood is pumped at a rate between 4 and 5 liters per minute.

580. The method of Example 567, wherein the blood is pumped at a rate between 4 and 5.5 liters per minute.

581. The method of Example 567, wherein the blood is pumped at a rate between 4 and 6 liters per minute.

582. The method of Example 567, wherein the blood is pumped at a rate between 4 and 6.5 liters per minute.

583. The method of Example 567, wherein the blood is pumped at a rate between 4 and 7 liters per minute.

584. The method of Example 567, wherein the blood is pumped at a rate between 4 and 7.5 liters per minute.

585. The method of Example 567, wherein the blood is pumped at a rate between 4 and 8 liters per minute.

586. The method of Example 567, wherein the blood is pumped at a rate between 4 and 8.5 liters per minute.

587. The method of Example 567, wherein the blood is pumped at a rate between 4 and 9 liters per minute.

588. The method of Example 567, wherein the blood is pumped at a rate between 4.5 and 9 liters per minute.

589. The method of Example 567, wherein the blood is pumped at a rate between 5 and 9 liters per minute.

590. The method of Example 567, wherein the blood is pumped at a rate between 5.5 and 9 liters per minute.

591. The method of Example 567, wherein the blood is pumped at a rate between 6 and 9 liters per minute.

592. The method of Example 567, wherein the blood is pumped at a rate between 6.5 and 9 liters per minute.

593. The method of Example 567, wherein the blood is pumped at a rate between 7 and 9 liters per minute.

594. The method of Example 567, wherein the blood is pumped at a rate between 7.5 and 9 liters per minute.

595. The method of Example 567, wherein the blood is pumped at a rate between 8 and 9 liters per minute.

596. The method of Example 567, wherein the blood is pumped at a rate between 8.5 and 9 liters per minute.

597. One or more of the methods of Examples 567-596, wherein the blood is pumped in the fluid flow path at a rate of at least 4 liters per minute for a duration of at least 30 minutes.

598. One or more of the methods of Examples 567-596, wherein the blood is pumped in the fluid flow path at a rate of at least 4 liters per minute for a duration of at least 2 hours.

599. One or more of the methods of Examples 567-596, wherein the blood is pumped in the fluid flow path at a rate of at least 4 liters per minute for a duration of at least 3 hours.

600. One or more of the methods of Examples 567-596, wherein the blood is pumped in the fluid flow path at a rate of at least 4 liters per minute for a duration of at least 4 hours.

601. One or more of the methods of Examples 509-600, further comprising performing dialysis on at least a portion of the blood at a rate of at least 0.5 liters per minute.

602. The method of Example 601, wherein performing dialysis comprises performing convection dialysis.

603. The method of Example 601, wherein performing dialysis comprises performing diffusion dialysis.

604. One or more of the methods of Examples 509-603, further comprising adding electrolyte-balanced fluid to at least a portion of the blood at a rate of at least 7 liters per hour.

605. The method of Example 604, wherein the electrolyte-balanced fluid is at a temperature of at least 35 degrees Celsius.

606. One or more of the methods of Examples 601-603, wherein the dialysis is performed at a rate of at least 0.55 liters per minute.

607. One or more of the methods of Examples 601-603, wherein the dialysis is performed at a rate of at least 0.6 liters per minute.

608. One or more of the methods of Examples 601-603, wherein the dialysis is performed at a rate of at least 0.65 liters per minute.

609. One or more of the methods of Examples 601-603, wherein the dialysis is performed at a rate of at least 0.7 liters per minute.

610. One or more of the methods of Examples 601-603, wherein the dialysis is performed at a rate of at least 0.75 liters per minute.

611. One or more of the methods of Examples 601-603, wherein the dialysis is performed at a rate of at least 0.8 liters per minute.

612. One or more of the methods of Examples 601-603, wherein the dialysis is performed at a rate of at least 0.85 liters per minute.

613. One or more of the methods of Examples 601-603, wherein the dialysis is performed at a rate of at least 0.9 liters per minute.

614. One or more of the methods of Examples 601-603, wherein the dialysis is performed at a rate of at least 0.95 liters per minute.

615. One or more of the methods of Examples 601-603, wherein the dialysis is performed at a rate of at least 1 liter per minute.

616. One or more of the methods of Examples 601-603, wherein the dialysis is performed at a rate of at least 1.1 liters per minute.

617. One or more of the methods of Examples 601-603, wherein the dialysis is performed at a rate of at least 1.2 liters per minute.

618. One or more of the methods of Examples 601-603, wherein the dialysis is performed at a rate of at least 1.3 liters per minute.

619. One or more of the methods of Examples 601-603, wherein the dialysis is performed at a rate of at least 1.4 liters per minute.

620. One or more of the methods of Examples 601-603, wherein the dialysis is performed at a rate of at least 1.5 liters per minute.

621. One or more of the methods of Examples 601-603, wherein the dialysis is performed at a rate of at least 1.6 liters per minute.

622. One or more of the methods of Examples 601-603, wherein the dialysis is performed at a rate of at least 1.7 liters per minute.

623. One or more of the methods of Examples 601-603, wherein the dialysis is performed at a rate of at least 1.8 liters per minute.

624. One or more of the methods of Examples 601-603, wherein the dialysis is performed at a rate of at least 1.9 liters per minute.

625. One or more of the methods of Examples 601-603, wherein the dialysis is performed at a rate of at least 2 liters per minute.

626. One or more of the methods of Examples 601-603, wherein the dialysis is performed at a rate of at least 2.1 liters per minute.

627. One or more of the methods of Examples 601-603, wherein the dialysis is performed at a rate of at least 2.2 liters per minute.

628. One or more of the methods of Examples 601-603, wherein the dialysis is performed at a rate of at least 2.3 liters per minute.

629. One or more of the methods of Examples 601-603, wherein the dialysis is performed at a rate of at least 2.4 liters per minute.

630. One or more of the methods of Examples 601-603, wherein the dialysis is performed at a rate of at least 2.5 liters per minute.

631. One or more of the methods of Examples 601-603, wherein the dialysis is performed at a rate of at least 2.6 liters per minute.

632. One or more of the methods of Examples 601-603, wherein the dialysis is performed at a rate of at least 2.7 liters per minute.

633. One or more of the methods of Examples 601-603, wherein the dialysis is performed at a rate of at least 2.8 liters per minute.

634. One or more of the methods of Examples 601-603, wherein the dialysis is performed at a rate of at least 2.9 liters per minute.

635. One or more of the methods of Examples 601-603, wherein the dialysis is performed at a rate of at least 3 liters per minute.

636. One or more of the methods of Examples 601-603, wherein the dialysis is performed at a rate between 0.5 and 0.55 liters per minute.

637. One or more of the methods of Examples 601-603, wherein the dialysis is performed at a rate between 0.5 and 0.6 liters per minute.

638. One or more of the methods of Examples 601-603, wherein the dialysis is performed at a rate between 0.5 and 0.65 liters per minute.

639. One or more of the methods of Examples 601-603, wherein the dialysis is performed at a rate between 0.5 and 0.7 liters per minute.

640. One or more of the methods of Examples 601-603, wherein the dialysis is performed at a rate between 0.5 and 0.75 liters per minute.

641. One or more of the methods of Examples 601-603, wherein the dialysis is performed at a rate between 0.5 and 0.8 liters per minute.

642. One or more of the methods of Examples 601-603, wherein the dialysis is performed at a rate between 0.5 and 0.85 liters per minute.

643. One or more of the methods of Examples 601-603, wherein the dialysis is performed at a rate between 0.5 and 0.9 liters per minute.

644. One or more of the methods of Examples 601-603, wherein the dialysis is performed at a rate between 0.5 and 0.95 liters per minute.

645. One or more of the methods of Examples 601-603, wherein the dialysis is performed at a rate between 0.5 and 1 liters per minute.

646. One or more of the methods of Examples 601-603, wherein the dialysis is performed at a rate between 0.5 and 1.1 liters per minute.

647. One or more of the methods of Examples 601-603, wherein the dialysis is performed at a rate between 0.5 and 1.2 liters per minute.

648. One or more of the methods of Examples 601-603, wherein the dialysis is performed at a rate between 0.5 and 1.3 liters per minute.

649. One or more of the methods of Examples 601-603, wherein the dialysis is performed at a rate between 0.5 and 1.4 liters per minute.

650. One or more of the methods of Examples 601-603, wherein the dialysis is performed at a rate between 0.5 and 1.5 liters per minute.

651. One or more of the methods of Examples 601-603, wherein the dialysis is performed at a rate between 0.5 and 1.6 liters per minute.

652. One or more of the methods of Examples 601-603, wherein the dialysis is performed at a rate between 0.5 and 1.7 liters per minute.

653. One or more of the methods of Examples 601-603, wherein the dialysis is performed at a rate between 0.5 and 1.8 liters per minute.

654. One or more of the methods of Examples 601-603, wherein the dialysis is performed at a rate between 0.5 and 1.9 liters per minute.

655. One or more of the methods of Examples 601-603, wherein the dialysis is performed at a rate between 0.5 and 2 liters per minute.

656. One or more of the methods of Examples 601-603, wherein the dialysis is performed at a rate between 0.5 and 2.1 liters per minute.

657. One or more of the methods of Examples 601-603, wherein the dialysis is performed at a rate between 0.5 and 2.2 liters per minute.

658. One or more of the methods of Examples 601-603, wherein the dialysis is performed at a rate between 0.5 and 2.3 liters per minute.

659. One or more of the methods of Examples 601-603, wherein the dialysis is performed at a rate between 0.5 and 2.4 liters per minute.

660. One or more of the methods of Examples 601-603, wherein the dialysis is performed at a rate between 0.5 and 2.5 liters per minute.

661. One or more of the methods of Examples 601-603, wherein the dialysis is performed at a rate between 0.5 and 2.6 liters per minute.

662. One or more of the methods of Examples 601-603, wherein the dialysis is performed at a rate between 0.5 and 2.7 liters per minute.

663. One or more of the methods of Examples 601-603, wherein the dialysis is performed at a rate between 0.5 and 2.8 liters per minute.

664. One or more of the methods of Examples 601-603, wherein the dialysis is performed at a rate between 0.5 and 2.9 liters per minute.

665. One or more of the methods of Examples 601-603, wherein the dialysis is performed at a rate between 0.5 and 3 liters per minute.

666. One or more of the methods of Examples 601-603, wherein the dialysis is performed at a rate between 0.55 and 3 liters per minute.

667. One or more of the methods of Examples 601-603, wherein the dialysis is performed at a rate between 0.6 and 3 liters per minute.

668. One or more of the methods of Examples 601-603, wherein the dialysis is performed at a rate between 0.65 and 3 liters per minute.

669. One or more of the methods of Examples 601-603, wherein the dialysis is performed at a rate between 0.7 and 3 liters per minute.

670. One or more of the methods of Examples 601-603, wherein the dialysis is performed at a rate between 0.75 and 3 liters per minute.

671. One or more of the methods of Examples 601-603, wherein the dialysis is performed at a rate between 0.8 and 3 liters per minute.

672. One or more of the methods of Examples 601-603, wherein the dialysis is performed at a rate between 0.85 and 3 liters per minute.

673. One or more of the methods of Examples 601-603, wherein the dialysis is performed at a rate between 0.9 and 3 liters per minute.

674. One or more of the methods of Examples 601-603, wherein the dialysis is performed at a rate between 0.95 and 3 liters per minute.

675. One or more of the methods of Examples 601-603, wherein the dialysis is performed at a rate between 1 and 3 liters per minute.

676. One or more of the methods of Examples 601-603, wherein the dialysis is performed at a rate between 1.1 and 3 liters per minute.

677. One or more of the methods of Examples 601-603, wherein the dialysis is performed at a rate between 1.2 and 3 liters per minute.

678. One or more of the methods of Examples 601-603, wherein the dialysis is performed at a rate between 1.3 and 3 liters per minute.

679. One or more of the methods of Examples 601-603, wherein the dialysis is performed at a rate between 1.4 and 3 liters per minute.

680. One or more of the methods of Examples 601-603, wherein the dialysis is performed at a rate between 1.5 and 3 liters per minute.

681. One or more of the methods of Examples 601-603, wherein the dialysis is performed at a rate between 1.6 and 3 liters per minute.

682. One or more of the methods of Examples 601-603, wherein the dialysis is performed at a rate between 1.7 and 3 liters per minute.

683. One or more of the methods of Examples 601-603, wherein the dialysis is performed at a rate between 1.8 and 3 liters per minute.

684. One or more of the methods of Examples 601-603, wherein the dialysis is performed at a rate between 1.9 and 3 liters per minute.

685. One or more of the methods of Examples 601-603, wherein the dialysis is performed at a rate between 2 and 3 liters per minute.

686. One or more of the methods of Examples 601-603, wherein the dialysis is performed at a rate between 2.1 and 3 liters per minute.

687. One or more of the methods of Examples 601-603, wherein the dialysis is performed at a rate between 2.2 and 3 liters per minute.

688. One or more of the methods of Examples 601-603, wherein the dialysis is performed at a rate between 2.3 and 3 liters per minute.

689. One or more of the methods of Examples 601-603, wherein the dialysis is performed at a rate between 2.4 and 3 liters per minute.

690. One or more of the methods of Examples 601-603, wherein the dialysis is performed at a rate between 2.5 and 3 liters per minute.

691. One or more of the methods of Examples 601-603, wherein the dialysis is performed at a rate between 2.6 and 3 liters per minute.

692. One or more of the methods of Examples 601-603, wherein the dialysis is performed at a rate between 2.7 and 3 liters per minute.

693. One or more of the methods of Examples 601-603, wherein the dialysis is performed at a rate between 2.8 and 3 liters per minute.

694. One or more of the methods of Examples 601-603, wherein the dialysis is performed at a rate between 2.9 and 3 liters per minute.

695. One or more of the methods of Examples 601-694, wherein performing the dialysis comprises:
- receiving at least a portion of the blood at a location on the fluid flow path downstream from one or more pumps; and
- causing blood treated with dialysis to enter the fluid flow path upstream from the one or more pumps.

696. One or more of the methods of Examples 601-695, wherein the dialysis is performed on at least a portion of the blood for a duration of at least 1 hour.

697. One or more of the methods of Examples 601-695, wherein the dialysis is performed on at least a portion of the blood for a duration of at least 2 hours.

698. One or more of the methods of Examples 601-695, wherein the dialysis is performed on at least a portion of the blood for a duration of at least 3 hours.

699. One or more of the methods of Examples 601-695, wherein the dialysis is performed on at least a portion of the blood for a duration of at least 4 hours.

700. One or more of the methods of Examples 601-695, wherein the dialysis is performed on at least a portion of the blood for a duration of at least 5 hours.

701. One or more of the methods of Examples 601-695, wherein the dialysis is performed on at least a portion of the blood for a duration of at least 6 hours.

702. One or more of the methods of Examples 601-695, wherein the dialysis is performed on at least a portion of the blood for a duration of at least 7 hours.

703. One or more of the methods of Examples 601-695, wherein the dialysis is performed on at least a portion of the blood for a duration of at least 8 hours.

704. One or more of the methods of Examples 852-946, wherein the dialysis is performed on at least a portion of the blood for a duration of at least 12 hours.

705. One or more of the methods of Examples 601-695, wherein the dialysis is performed on at least a portion of the blood for a duration of at least 16 hours.

706. One or more of the methods of Examples 601-695, wherein the dialysis is performed on at least a portion of the blood for a duration of at least 24 hours.

707. One or more of the methods of Examples 601-695, wherein the dialysis is performed on at least a portion of the blood for a duration of at least 36 hours.

708. One or more of the methods of Examples 601-695, wherein the dialysis is performed on at least a portion of the blood for a duration of at least 48 hours.

709. A system comprising:
- one or more pumps configured to pump blood in a fluid flow path at a collective rate of at least 4 liters per minute; and
- one or more heat exchangers coupled to the fluid flow path and configured to heat at least a portion of the blood from the fluid flow path to a temperature of at least 42 degrees Celsius.

710. The system of Example 709, wherein the one or more heat exchangers are configured to heat at least a portion of the blood to a temperature of at least 42.5 degrees Celsius.

711. The system of Example 709, wherein the one or more heat exchangers are configured to heat at least a portion of the blood to a temperature of at least 43 degrees Celsius.

712. The system of Example 709, wherein the one or more heat exchangers are configured to heat at least a portion of the blood to a temperature of at least 43.5 degrees Celsius.

713. The system of Example 709, wherein the one or more heat exchangers are configured to heat at least a portion of the blood to a temperature of at least 44 degrees Celsius.

714. The system of Example 709, wherein the one or more heat exchangers are configured to heat at least a portion of the blood to a temperature of at least 44.5 degrees Celsius.

715. The system of Example 709, wherein the one or more heat exchangers are configured to heat at least a portion of the blood to a temperature of at least 45 degrees Celsius.

716. The system of Example 709, wherein the one or more heat exchangers are configured to heat at least a portion of the blood to a temperature between 42 and 42.5 degrees Celsius.

717. The system of Example 709, wherein the one or more heat exchangers are configured to heat at least a portion of the blood to a temperature between 42 and 43 degrees Celsius.

718. The system of Example 709, wherein the one or more heat exchangers are configured to heat at least a portion of the blood to a temperature between 42 and 43.5 degrees Celsius.

719. The system of Example 709, wherein the one or more heat exchangers are configured to heat at least a portion of the blood to a temperature between 42 and 44 degrees Celsius.

720. The system of Example 709, wherein the one or more heat exchangers are configured to heat at least a portion of the blood to a temperature between 42 and 44.5 degrees Celsius.

721. The system of Example 709, wherein the one or more heat exchangers are configured to heat at least a portion of the blood to a temperature between 42 and 45 degrees Celsius.

722. The system of Example 709, wherein the one or more heat exchangers are configured to heat at least a portion of the blood to a temperature between 42.5 and 45 degrees Celsius.

723. The system of Example 709, wherein the one or more heat exchangers are configured to heat at least a portion of the blood to a temperature between 43 and 45 degrees Celsius.

724. The system of Example 709, wherein the one or more heat exchangers are configured to heat at least a portion of the blood to a temperature between 43.5 and 45 degrees Celsius.

725. The system of Example 709, wherein the one or more heat exchangers are configured to heat at least a portion of the blood to a temperature between 44 and 45 degrees Celsius.

726. The system of Example 709, wherein the one or more heat exchangers are configured to heat at least a portion of the blood to a temperature between 44.5 and 45 degrees Celsius.

727. One or more of the systems of Examples 709-726, wherein the one or more pumps are configured to pump the blood at a collective rate of at least 4.5 liters per minute.

728. One or more of the systems of Examples 709-726, wherein the one or more pumps are configured to pump the blood at a collective rate of at least 5 liters per minute.

729. One or more of the systems of Examples 709-726, wherein the one or more pumps are configured to pump the blood at a collective rate of at least 5.5 liters per minute.

730. One or more of the systems of Examples 709-726, wherein the one or more pumps are configured to pump the blood at a collective rate of at least 6 liters per minute.

731. One or more of the systems of Examples 709-726, wherein the one or more pumps are configured to pump the blood at a collective rate of at least 6.5 liters per minute.

732. One or more of the systems of Examples 709-726, wherein the one or more pumps are configured to pump the blood at a collective rate of at least 7 liters per minute.

733. One or more of the systems of Examples 709-726, wherein the one or more pumps are configured to pump the blood at a collective rate of at least 7.5 liters per minute.

734. One or more of the systems of Examples 709-726, wherein the one or more pumps are configured to pump the blood at a collective rate of at least 8 liters per minute.

735. One or more of the systems of Examples 709-726, wherein the one or more pumps are configured to pump the blood at a collective rate of at least 8.5 liters per minute.

736. One or more of the systems of Examples 709-726, wherein the one or more pumps are configured to pump the blood at a collective rate of at least 9 liters per minute.

737. One or more of the systems of Examples 709-726, wherein the one or more pumps are configured to pump the blood at a collective rate between 4 and 4.5 liters per minute.

738. One or more of the systems of Examples 709-726, wherein the one or more pumps are configured to pump the blood at a collective rate between 4 and 5 liters per minute.

739. One or more of the systems of Examples 709-726, wherein the one or more pumps are configured to pump the blood at a collective rate between 4 and 5.5 liters per minute.

740. One or more of the systems of Examples 709-726, wherein the one or more pumps are configured to pump the blood at a collective rate between 4 and 6 liters per minute.

741. One or more of the systems of Examples 709-726, wherein the one or more pumps are configured to pump the blood at a collective rate between 4 and 6.5 liters per minute.

742. One or more of the systems of Examples 709-726, wherein the one or more pumps are configured to pump the blood at a collective rate between 4 and 7 liters per minute.

743. One or more of the systems of Examples 709-726, wherein the one or more pumps are configured to pump the blood at a collective rate between 4 and 7.5 liters per minute.

744. One or more of the systems of Examples 709-726, wherein the one or more pumps are configured to pump the blood at a collective rate between 4 and 8 liters per minute.

745. One or more of the systems of Examples 709-726, wherein the one or more pumps are configured to pump the blood at a collective rate between 4 and 8.5 liters per minute.

746. One or more of the systems of Examples 709-726, wherein the one or more pumps are configured to pump the blood at a collective rate between 4 and 9 liters per minute.

747. One or more of the systems of Examples 709-726, wherein the one or more pumps are configured to pump the blood at a collective rate between 4.5 and 9 liters per minute.

748. One or more of the systems of Examples 709-726, wherein the one or more pumps are configured to pump the blood at a collective rate between 5 and 9 liters per minute.

749. One or more of the systems of Examples 709-726, wherein the one or more pumps are configured to pump the blood at a collective rate between 5.5 and 9 liters per minute.

750. One or more of the systems of Examples 709-726, wherein the one or more pumps are configured to pump the blood at a collective rate between 6 and 9 liters per minute.

751. One or more of the systems of Examples 709-726, wherein the one or more pumps are configured to pump the blood at a collective rate between 6.5 and 9 liters per minute.

752. One or more of the systems of Examples 709-726, wherein the one or more pumps are configured to pump the blood at a collective rate between 7 and 9 liters per minute.

753. One or more of the systems of Examples 709-726, wherein the one or more pumps are configured to pump the blood at a collective rate between 7.5 and 9 liters per minute.

754. One or more of the systems of Examples 709-726, wherein the one or more pumps are configured to pump the blood at a collective rate between 8 and 9 liters per minute.

755. One or more of the systems of Examples 709-726, wherein the one or more pumps are configured to pump the blood at a collective rate between 8.5 and 9 liters per minute.

756. One or more of the systems of Examples 709-755, further comprising one or more venting modules coupled to the fluid flow path, the one or more venting modules configured to remove carbon dioxide from at least a portion of the blood.

757. One or more of the systems of Examples 709-756, wherein the one or more venting modules are configured to add oxygen to at least a portion of the blood.

758. One or more of the systems of Examples 709-756, wherein the one or more venting modules are configured to cause the blood to flow through at least one membrane.

759. The system of Example 758, wherein the at least one membrane collectively has an effective surface area greater than 1.8 square meters.

760. One or more of the systems of Examples 709-759, further comprising an oxygenator coupled to the fluid flow path, the oxygenator configured to cause oxygen to be added to at least a portion of the blood.

761. One or more of the systems of Examples 709-760, further comprising a reintroduction module coupled to the fluid flow path and configured to add a substance to at least a portion of the blood that facilitates the production of reactive oxygen species within the blood.

762. The system of Example 761, wherein the substance comprises a free radical.

763. The system of Example 761, wherein the substance comprises an unstable substance.

764. The system of Example 761, wherein the substance comprises ozone.

765. The system of Example 761, wherein the substance comprises Freon.

766. The system of Example 761, wherein the substance comprises iron.

767. The system of Example 761, wherein the substance comprises copper.

768. The system of Example 761, wherein the substance comprises ozone and iron.

769. The system of Example 761, wherein the substance comprises ozone and copper.

770. One or more of the systems of Examples 709-769, further comprising one or more dialysis modules coupled to the fluid flow path and configured to perform dialysis on at least a portion of the blood at a collective rate of at least 0.5 liters per minute.

771. The system of Example 770, wherein the one or more dialysis modules are configured to perform convection dialysis.

772. The system of Example 770, wherein the one or more dialysis modules are configured to perform diffusion dialysis.

773. One or more of the systems of Examples 709-772, further comprising a reintroduction module coupled to the fluid flow path and configured to add electrolyte-balanced fluid to at least a portion of the blood at a rate of at least 7 liters per hour.

774. The system of Example 773, wherein the electrolyte-balanced fluid is at a temperature of at least 35 degrees Celsius.

775. The system of Example 770, wherein the one or more dialysis modules are configured to perform dialysis on at least a portion of the blood at a collective rate of at least 0.55 liters per minute.

776. The system of Example 770, wherein the one or more dialysis modules are configured to perform dialysis on at least a portion of the blood at a collective rate of at least 0.6 liters per minute.

777. The system of Example 770, wherein the one or more dialysis modules are configured to perform dialysis on at least a portion of the blood at a collective rate of at least 0.65 liters per minute.

778. The system of Example 770, wherein the one or more dialysis modules are configured to perform dialysis on at least a portion of the blood at a collective rate of at least 0.7 liters per minute.

779. The system of Example 770, wherein the one or more dialysis modules are configured to perform dialysis on at least a portion of the blood at a collective rate of at least 0.75 liters per minute.

780. The system of Example 770, wherein the one or more dialysis modules are configured to perform dialysis on at least a portion of the blood at a collective rate of at least 0.8 liters per minute.

781. The system of Example 770, wherein the one or more dialysis modules are configured to perform dialysis on at least a portion of the blood at a collective rate of at least 0.85 liters per minute.

782. The system of Example 770, wherein the one or more dialysis modules are configured to perform dialysis on at least a portion of the blood at a collective rate of at least 0.9 liters per minute.

783. The system of Example 770, wherein the one or more dialysis modules are configured to perform dialysis on at least a portion of the blood at a collective rate of at least 0.95 liters per minute.

784. The system of Example 770, wherein the one or more dialysis modules are configured to perform dialysis on at least a portion of the blood at a collective rate of at least 1 liter per minute.

785. The system of Example 770, wherein the one or more dialysis modules are configured to perform dialysis on at least a portion of the blood at a collective rate between 0.5 and 0.55 liters per minute.

786. The system of Example 770, wherein the one or more dialysis modules are configured to perform dialysis on at least a portion of the blood at a collective rate between 0.5 and 0.6 liters per minute.

787. The system of Example 770, wherein the one or more dialysis modules are configured to perform dialysis on at least a portion of the blood at a collective rate between 0.5 and 0.65 liters per minute.

788. The system of Example 770, wherein the one or more dialysis modules are configured to perform dialysis on at least a portion of the blood at a collective rate between 0.5 and 0.7 liters per minute.

789. The system of Example 770, wherein the one or more dialysis modules are configured to perform dialysis on at least a portion of the blood at a collective rate between 0.5 and 0.75 liters per minute.

790. The system of Example 770, wherein the one or more dialysis modules are configured to perform dialysis on at least a portion of the blood at a collective rate between 0.5 and 0.8 liters per minute.

791. The system of Example 770, wherein the one or more dialysis modules are configured to perform dialysis on at least a portion of the blood at a collective rate between 0.5 and 0.85 liters per minute.

792. The system of Example 770, wherein the one or more dialysis modules are configured to perform dialysis on at least a portion of the blood at a collective rate between 0.5 and 0.9 liters per minute.

793. The system of Example 770, wherein the one or more dialysis modules are configured to perform dialysis on at least a portion of the blood at a collective rate between 0.5 and 0.95 liters per minute.

794. The system of Example 770, wherein the one or more dialysis modules are configured to perform dialysis on at least a portion of the blood at a collective rate between 0.5 and 1 liters per minute.

795. The system of Example 770, wherein the one or more dialysis modules are configured to perform dialysis on at least a portion of the blood at a collective rate between 0.55 and 1 liters per minute.

796. The system of Example 770, wherein the one or more dialysis modules are configured to perform dialysis on at least a portion of the blood at a collective rate between 0.6 and 1 liters per minute.

797. The system of Example 770, wherein the one or more dialysis modules are configured to perform dialysis on at least a portion of the blood at a collective rate between 0.65 and 1 liters per minute.

798. The system of Example 770, wherein the one or more dialysis modules are configured to perform dialysis on at least a portion of the blood at a collective rate between 0.7 and 1 liters per minute.

799. The system of Example 770, wherein the one or more dialysis modules are configured to perform dialysis on at least a portion of the blood at a collective rate between 0.75 and 1 liters per minute.

800. The system of Example 770, wherein the one or more dialysis modules are configured to perform dialysis on at least a portion of the blood at a collective rate between 0.8 and 1 liters per minute.

801. The system of Example 770, wherein the one or more dialysis modules are configured to perform dialysis on at least a portion of the blood at a collective rate between 0.85 and 1 liters per minute.

802. The system of Example 770, wherein the one or more dialysis modules are configured to perform dialysis on at least a portion of the blood at a collective rate between 0.9 and 1 liters per minute.

803. The system of Example 770, wherein the one or more dialysis modules are configured to perform dialysis on at least a portion of the blood at a collective rate between 0.95 and 1 liters per minute.

804. One or more of the systems of Examples 770-803, wherein:
the one or more dialysis modules are configured to receive at least a portion of the blood at a location on the fluid flow path downstream from the one or more pumps; and
the one or more dialysis modules are configured to cause blood treated with dialysis to enter the fluid flow path upstream from the one or more pumps.

805. A method comprising:
pumping blood in a fluid flow path at a rate of at least 4 liters per minute; and
heating at least a portion of the blood from the fluid flow path to a temperature of at least 42 degrees Celsius for at least 15 minutes.

806. The method of Example 805, wherein at least a portion of the blood is heated to a temperature of at least 42.5 degrees Celsius.

807. The method of Example 805, wherein at least a portion of the blood is heated to a temperature of at least 43 degrees Celsius.

808. The method of Example 805, wherein at least a portion of the blood is heated to a temperature of at least 43.5 degrees Celsius.

809. The method of Example 805, wherein at least a portion of the blood is heated to a temperature of at least 44 degrees Celsius.

810. The method of Example 805, wherein at least a portion of the blood is heated to a temperature of at least 44.5 degrees Celsius.

811. The method of Example 805, wherein at least a portion of the blood is heated to a temperature of at least 45 degrees Celsius.

812. The method of Example 805, wherein at least a portion of the blood is heated to a temperature between 42 and 42.5 degrees Celsius.

813. The method of Example 805, wherein at least a portion of the blood is heated to a temperature between 42 and 43 degrees Celsius.

814. The method of Example 805, wherein at least a portion of the blood is heated to a temperature between 42 and 43.5 degrees Celsius.

815. The method of Example 805, wherein at least a portion of the blood is heated to a temperature between 42 and 44 degrees Celsius.

816. The method of Example 805, wherein at least a portion of the blood is heated to a temperature between 42 and 44.5 degrees Celsius.

817. The method of Example 805, wherein at least a portion of the blood is heated to a temperature between 42 and 45 degrees Celsius.

818. The method of Example 805, wherein at least a portion of the blood is heated to a temperature between 42.5 and 45 degrees Celsius.

819. The method of Example 805, wherein at least a portion of the blood is heated to a temperature between 43 and 45 degrees Celsius.

820. The method of Example 805, wherein at least a portion of the blood is heated to a temperature between 43.5 and 45 degrees Celsius.

821. The method of Example 805, wherein at least a portion of the blood is heated to a temperature between 44 and 45 degrees Celsius.

822. The method of Example 805, wherein at least a portion of the blood is heated to a temperature between 44.5 and 45 degrees Celsius.

823. One or more of the methods of Examples 805-822, wherein the blood is pumped at a rate of at least 4.5 liters per minute.

824. One or more of the methods of Examples 805-822, wherein the blood is pumped at a rate of at least 5 liters per minute.

825. One or more of the methods of Examples 805-822, wherein the blood is pumped at a rate of at least 5.5 liters per minute.

826. One or more of the methods of Examples 805-822, wherein the blood is pumped at a rate of at least 6 liters per minute.

827. One or more of the methods of Examples 805-822, wherein the blood is pumped at a rate of at least 6.5 liters per minute.

828. One or more of the methods of Examples 805-822, wherein the blood is pumped at a rate of at least 7 liters per minute.

829. One or more of the methods of Examples 805-822, wherein the blood is pumped at a rate of at least 7.5 liters per minute.

830. One or more of the methods of Examples 805-822, wherein the blood is pumped at a rate of at least 8 liters per minute.

831. One or more of the methods of Examples 805-822, wherein the blood is pumped at a rate of at least 8.5 liters per minute.

832. One or more of the methods of Examples 805-822, wherein the blood is pumped at a rate of at least 9 liters per minute.

833. One or more of the methods of Examples 805-822, wherein the blood is pumped at a rate between 4 and 4.5 liters per minute.

834. One or more of the methods of Examples 805-822, wherein the blood is pumped at a rate between 4 and 5 liters per minute.

835. One or more of the methods of Examples 805-822, wherein the blood is pumped at a rate between 4 and 5.5 liters per minute.

836. One or more of the methods of Examples 805-822, wherein the blood is pumped at a rate between 4 and 6 liters per minute.

837. One or more of the methods of Examples 805-822, wherein the blood is pumped at a rate between 4 and 6.5 liters per minute.

838. One or more of the methods of Examples 805-822, wherein the blood is pumped at a rate between 4 and 7 liters per minute.

839. One or more of the methods of Examples 805-822, wherein the blood is pumped at a rate between 4 and 7.5 liters per minute.

840. One or more of the methods of Examples 805-822, wherein the blood is pumped at a rate between 4 and 8 liters per minute.

841. One or more of the methods of Examples 805-822, wherein the blood is pumped at a rate between 4 and 8.5 liters per minute.

842. One or more of the methods of Examples 805-822, wherein the blood is pumped at a rate between 4 and 9 liters per minute.

843. One or more of the methods of Examples 805-822, wherein the blood is pumped at a rate between 4.5 and 9 liters per minute.

844. One or more of the methods of Examples 805-822, wherein the blood is pumped at a rate between 5 and 9 liters per minute.

845. One or more of the methods of Examples 805-822, wherein the blood is pumped at a rate between 5.5 and 9 liters per minute.

846. One or more of the methods of Examples 805-822, wherein the blood is pumped at a rate between 6 and 9 liters per minute.

847. One or more of the methods of Examples 805-822, wherein the blood is pumped at a rate between 6.5 and 9 liters per minute.

848. One or more of the methods of Examples 805-822, wherein the blood is pumped at a rate between 7 and 9 liters per minute.

849. One or more of the methods of Examples 805-822, wherein the blood is pumped at a rate between 7.5 and 9 liters per minute.

850. One or more of the methods of Examples 805-822, wherein the blood is pumped at a rate between 8 and 9 liters per minute.

851. One or more of the methods of Examples 805-822, wherein the blood is pumped at a rate between 8.5 and 9 liters per minute.

852. One or more of the methods of Examples 805-851, further comprising performing dialysis on at least a portion of the blood at a rate of at least 0.5 liters per minute.

853. The method of Example 852, wherein performing dialysis comprises performing convection dialysis.

854. The method of Example 852, wherein performing dialysis comprises performing diffusion dialysis.

855. One or more of the methods of Examples 805-854, further comprising adding electrolyte-balanced fluid to at least a portion of the blood at a rate of at least 7 liters per hour.

856. The method of Example 855, wherein the electrolyte-balanced fluid is at a temperature of at least 35 degrees Celsius.

857. The method of Example 852, wherein the dialysis is performed at a rate of at least 0.55 liters per minute.

858. The method of Example 852, wherein the dialysis is performed at a rate of at least 0.6 liters per minute.

859. The method of Example 852, wherein the dialysis is performed at a rate of at least 0.65 liters per minute.

860. The method of Example 852, wherein the dialysis is performed at a rate of at least 0.7 liters per minute.

861. The method of Example 852, wherein the dialysis is performed at a rate of at least 0.75 liters per minute.

862. The method of Example 852, wherein the dialysis is performed at a rate of at least 0.8 liters per minute.

863. The method of Example 852, wherein the dialysis is performed at a rate of at least 0.85 liters per minute.

864. The method of Example 852, wherein the dialysis is performed at a rate of at least 0.9 liters per minute.

865. The method of Example 852, wherein the dialysis is performed at a rate of at least 0.95 liters per minute.

866. The method of Example 852, wherein the dialysis is performed at a rate of at least 1 liter per minute.

867. The method of Example 852, wherein the dialysis is performed at a rate of at least 1.1 liters per minute.

868. The method of Example 852, wherein the dialysis is performed at a rate of at least 1.2 liters per minute.

869. The method of Example 852, wherein the dialysis is performed at a rate of at least 1.3 liters per minute.

870. The method of Example 852, wherein the dialysis is performed at a rate of at least 1.4 liters per minute.

871. The method of Example 852, wherein the dialysis is performed at a rate of at least 1.5 liters per minute.

872. The method of Example 852, wherein the dialysis is performed at a rate of at least 1.6 liters per minute.

873. The method of Example 852, wherein the dialysis is performed at a rate of at least 1.7 liters per minute.

874. The method of Example 852, wherein the dialysis is performed at a rate of at least 1.8 liters per minute.

875. The method of Example 852, wherein the dialysis is performed at a rate of at least 1.9 liters per minute.

876. The method of Example 852, wherein the dialysis is performed at a rate of at least 2 liters per minute.

877. The method of Example 852, wherein the dialysis is performed at a rate of at least 2.1 liters per minute.

878. The method of Example 852, wherein the dialysis is performed at a rate of at least 2.2 liters per minute.

879. The method of Example 852, wherein the dialysis is performed at a rate of at least 2.3 liters per minute.

880. The method of Example 852, wherein the dialysis is performed at a rate of at least 2.4 liters per minute.

881. The method of Example 852, wherein the dialysis is performed at a rate of at least 2.5 liters per minute.

882. The method of Example 852, wherein the dialysis is performed at a rate of at least 2.6 liters per minute.

883. The method of Example 852, wherein the dialysis is performed at a rate of at least 2.7 liters per minute.

884. The method of Example 852, wherein the dialysis is performed at a rate of at least 2.8 liters per minute.

885. The method of Example 852, wherein the dialysis is performed at a rate of at least 2.9 liters per minute.

886. The method of Example 852, wherein the dialysis is performed at a rate of at least 3 liters per minute.

887. The method of Example 852, wherein the dialysis is performed at a rate between 0.5 and 0.55 liters per minute.

888. The method of Example 852, wherein the dialysis is performed at a rate between 0.5 and 0.6 liters per minute.

889. The method of Example 852, wherein the dialysis is performed at a rate between 0.5 and 0.65 liters per minute.

890. The method of Example 852, wherein the dialysis is performed at a rate between 0.5 and 0.7 liters per minute.

891. The method of Example 852, wherein the dialysis is performed at a rate between 0.5 and 0.75 liters per minute.

892. The method of Example 852, wherein the dialysis is performed at a rate between 0.5 and 0.8 liters per minute.

893. The method of Example 852, wherein the dialysis is performed at a rate between 0.5 and 0.85 liters per minute.

894. The method of Example 852, wherein the dialysis is performed at a rate between 0.5 and 0.9 liters per minute.

895. The method of Example 852, wherein the dialysis is performed at a rate between 0.5 and 0.95 liters per minute.

896. The method of Example 852, wherein the dialysis is performed at a rate between 0.5 and 1 liters per minute.

897. The method of Example 852, wherein the dialysis is performed at a rate between 0.5 and 1.1 liters per minute.

898. The method of Example 852, wherein the dialysis is performed at a rate between 0.5 and 1.2 liters per minute.

899. The method of Example 852, wherein the dialysis is performed at a rate between 0.5 and 1.3 liters per minute.

900. The method of Example 852, wherein the dialysis is performed at a rate between 0.5 and 1.4 liters per minute.

901. The method of Example 852, wherein the dialysis is performed at a rate between 0.5 and 1.5 liters per minute.

902. The method of Example 852, wherein the dialysis is performed at a rate between 0.5 and 1.6 liters per minute.

903. The method of Example 852, wherein the dialysis is performed at a rate between 0.5 and 1.7 liters per minute.

904. The method of Example 852, wherein the dialysis is performed at a rate between 0.5 and 1.8 liters per minute.

905. The method of Example 852, wherein the dialysis is performed at a rate between 0.5 and 1.9 liters per minute.

906. The method of Example 852, wherein the dialysis is performed at a rate between 0.5 and 2 liters per minute.

907. The method of Example 852, wherein the dialysis is performed at a rate between 0.5 and 2.1 liters per minute.

908. The method of Example 852, wherein the dialysis is performed at a rate between 0.5 and 2.2 liters per minute.

909. The method of Example 852, wherein the dialysis is performed at a rate between 0.5 and 2.3 liters per minute.

910. The method of Example 852, wherein the dialysis is performed at a rate between 0.5 and 2.4 liters per minute.

911. The method of Example 852, wherein the dialysis is performed at a rate between 0.5 and 2.5 liters per minute.

912. The method of Example 852, wherein the dialysis is performed at a rate between 0.5 and 2.6 liters per minute.

913. The method of Example 852, wherein the dialysis is performed at a rate between 0.5 and 2.7 liters per minute.

914. The method of Example 852, wherein the dialysis is performed at a rate between 0.5 and 2.8 liters per minute.

915. The method of Example 852, wherein the dialysis is performed at a rate between 0.5 and 2.9 liters per minute.

916. The method of Example 852, wherein the dialysis is performed at a rate between 0.5 and 3 liters per minute.

917. The method of Example 852, wherein the dialysis is performed at a rate between 0.55 and 3 liters per minute.

918. The method of Example 852, wherein the dialysis is performed at a rate between 0.6 and 3 liters per minute.

919. The method of Example 852, wherein the dialysis is performed at a rate between 0.65 and 3 liters per minute.

920. The method of Example 852, wherein the dialysis is performed at a rate between 0.7 and 3 liters per minute.

921. The method of Example 852, wherein the dialysis is performed at a rate between 0.75 and 3 liters per minute.

922. The method of Example 852, wherein the dialysis is performed at a rate between 0.8 and 3 liters per minute.

923. The method of Example 852, wherein the dialysis is performed at a rate between 0.85 and 3 liters per minute.

924. The method of Example 852, wherein the dialysis is performed at a rate between 0.9 and 3 liters per minute.

925. The method of Example 852, wherein the dialysis is performed at a rate between 0.95 and 3 liters per minute.

926. The method of Example 852, wherein the dialysis is performed at a rate between 1 and 3 liters per minute.

927. The method of Example 852, wherein the dialysis is performed at a rate between 1.1 and 3 liters per minute.

928. The method of Example 852, wherein the dialysis is performed at a rate between 1.2 and 3 liters per minute.

929. The method of Example 852, wherein the dialysis is performed at a rate between 1.3 and 3 liters per minute.

930. The method of Example 852, wherein the dialysis is performed at a rate between 1.4 and 3 liters per minute.

931. The method of Example 852, wherein the dialysis is performed at a rate between 1.5 and 3 liters per minute.

932. The method of Example 852, wherein the dialysis is performed at a rate between 1.6 and 3 liters per minute.

933. The method of Example 852, wherein the dialysis is performed at a rate between 1.7 and 3 liters per minute.

934. The method of Example 852, wherein the dialysis is performed at a rate between 1.8 and 3 liters per minute.

935. The method of Example 852, wherein the dialysis is performed at a rate between 1.9 and 3 liters per minute.

936. The method of Example 852, wherein the dialysis is performed at a rate between 2 and 3 liters per minute.

937. The method of Example 852, wherein the dialysis is performed at a rate between 2.1 and 3 liters per minute.

938. The method of Example 852, wherein the dialysis is performed at a rate between 2.2 and 3 liters per minute.

939. The method of Example 852, wherein the dialysis is performed at a rate between 2.3 and 3 liters per minute.

940. The method of Example 852, wherein the dialysis is performed at a rate between 2.4 and 3 liters per minute.

941. The method of Example 852, wherein the dialysis is performed at a rate between 2.5 and 3 liters per minute.

942. The method of Example 852, wherein the dialysis is performed at a rate between 2.6 and 3 liters per minute.

943. The method of Example 852, wherein the dialysis is performed at a rate between 2.7 and 3 liters per minute.

944. The method of Example 852, wherein the dialysis is performed at a rate between 2.8 and 3 liters per minute.

945. The method of Example 852, wherein the dialysis is performed at a rate between 2.9 and 3 liters per minute.

946. One or more of the methods of Examples 852-945, wherein performing the dialysis comprises:
receiving at least a portion of the blood at a location on the fluid flow path downstream from one or more pumps; and
causing blood treated with dialysis to enter the fluid flow path upstream from the one or more pumps.

947. One or more of the methods of Examples 852-946, wherein the dialysis is performed on the blood for a duration of at least 1 hour.

948. One or more of the methods of Examples 852-946, wherein the dialysis is performed on the blood for a duration of at least 2 hours.

949. One or more of the methods of Examples 852-946, wherein the dialysis is performed on the blood for a duration of at least 3 hours.

950. One or more of the methods of Examples 852-946, wherein the dialysis is performed on the blood for a duration of at least 4 hours.

951. One or more of the methods of Examples 852-946, wherein the dialysis is performed on the blood for a duration of at least 5 hours.

952. One or more of the methods of Examples 852-946, wherein the dialysis is performed on the blood for a duration of at least 6 hours.

953. One or more of the methods of Examples 852-946, wherein the dialysis is performed on the blood for a duration of at least 7 hours.

954. One or more of the methods of Examples 852-946, wherein the dialysis is performed on the blood for a duration of at least 8 hours.

955. One or more of the methods of Examples 852-946, wherein the dialysis is performed on the blood for a duration of at least 12 hours.

956. One or more of the methods of Examples 852-946, wherein the dialysis is performed on the blood for a duration of at least 16 hours.

957. One or more of the methods of Examples 852-946, wherein the dialysis is performed on the blood for a duration of at least 24 hours.

958. One or more of the methods of Examples 852-946, wherein the dialysis is performed on the blood for a duration of at least 36 hours.

959. One or more of the methods of Examples 852-946, wherein the dialysis is performed on the blood for a duration of at least 48 hours.

960. One or more of the methods of Examples 805-959, further comprising removing carbon dioxide from at least a portion of the blood.

961. One or more of the methods of Examples 805-960, further comprising adding oxygen to at least a portion of the blood.

962. The method of Example 960, wherein removing carbon dioxide from at least a portion of the blood comprises causing the blood to flow through at least one membrane.

963. The method of Example 949, wherein the at least one membrane collectively has an effective surface area greater than 1.8 square meters.

964. One or more of the methods of Examples 960-963, wherein carbon dioxide is removed from at least a portion of the blood for at least 30 minutes.

965. One or more of the methods of Examples 960-963, wherein carbon dioxide is removed from at least a portion of the blood for at least 1 hour.

966. One or more of the methods of Examples 960-963, wherein carbon dioxide is removed from at least a portion of the blood for at least 1.5 hours.

967. One or more of the methods of Examples 960-963, wherein carbon dioxide is removed from at least a portion of the blood for at least 2 hours.

968. One or more of the methods of Examples 960-963, wherein carbon dioxide is removed from at least a portion of the blood for at least 2.5 hours.

969. One or more of the methods of Examples 960-963, wherein carbon dioxide is removed from at least a portion of the blood for at least 3 hours.

970. One or more of the methods of Examples 960-963, wherein carbon dioxide is removed from at least a portion of the blood for at least 3.5 hours.

971. One or more of the methods of Examples 960-963, wherein carbon dioxide is removed from at least a portion of the blood for at least 4 hours.

972. One or more of the methods of Examples 960-963, wherein carbon dioxide is removed from at least a portion of the blood for at least 4.5 hours.

973. One or more of the methods of Examples 960-963, wherein carbon dioxide is removed from at least a portion of the blood for at least 5 hours.

974. One or more of the methods of Examples 960-963, wherein carbon dioxide is removed from at least a portion of the blood for at least 5.5 hours.

975. One or more of the methods of Examples 960-963, wherein carbon dioxide is removed from at least a portion of the blood for at least 6 hours.

976. One or more of the methods of Examples 960-963, wherein carbon dioxide is removed from at least a portion of the blood for at least 6.5 hours.

977. One or more of the methods of Examples 960-963, wherein carbon dioxide is removed from at least a portion of the blood for at least 7 hours.

978. One or more of the methods of Examples 960-963, wherein carbon dioxide is removed from at least a portion of the blood for at least 7.5 hours.

979. One or more of the methods of Examples 960-963, wherein carbon dioxide is removed from at least a portion of the blood for at least 8 hours.

980. One or more of the methods of Examples 805-979, further comprising adding a substance to at least a portion of the blood that facilitates the production of reactive oxygen species within the blood.

981. The method of Example 980, wherein the substance comprises a free radical.

982. The method of Example 980, wherein the substance comprises an unstable substance.

983. The method of Example 980, wherein the substance comprises ozone.

984. The method of Example 980, wherein the substance comprises Freon.

985. The method of Example 980, wherein the substance comprises iron.

986. The method of Example 980, wherein the substance comprises copper.

987. The method of Example 980, wherein the substance comprises ozone and iron.

988. The method of Example 980, wherein the substance comprises ozone and copper.

989. One or more of the methods of Examples 805-988, wherein at least a portion of the blood is heated to a temperature of at least 42 degrees Celsius for at least 30 minutes.

990. One or more of the methods of Examples 805-988, wherein at least a portion of the blood is heated to a temperature of at least 42 degrees Celsius for at least 1 hour.

991. One or more of the methods of Examples 805-988, wherein at least a portion of the blood is heated to a temperature of at least 42 degrees Celsius for at least 1.5 hours.

992. One or more of the methods of Examples 805-988, wherein at least a portion of the blood is heated to a temperature of at least 42 degrees Celsius for at least 2 hours.

993. One or more of the methods of Examples 805-988, wherein at least a portion of the blood is heated to a temperature of at least 42 degrees Celsius for at least 2.5 hours.

994. One or more of the methods of Examples 805-988, wherein at least a portion of the blood is heated to a temperature of at least 42 degrees Celsius for at least 3 hours.

995. One or more of the methods of Examples 805-988, wherein at least a portion of the blood is heated to a temperature of at least 42 degrees Celsius for at least 3.5 hours.

996. One or more of the methods of Examples 805-988, wherein at least a portion of the blood is heated to a temperature of at least 42 degrees Celsius for at least 4 hours.

997. One or more of the methods of Examples 805-988, wherein at least a portion of the blood is heated to a temperature of at least 42 degrees Celsius for at least 4.5 hours.

998. One or more of the methods of Examples 805-988, wherein at least a portion of the blood is heated to a temperature of at least 42 degrees Celsius for at least 5 hours.

999. One or more of the methods of Examples 805-988, wherein at least a portion of the blood is heated to a temperature of at least 42 degrees Celsius for at least 5.5 hours.

1000. One or more of the methods of Examples 805-988, wherein at least a portion of the blood is heated to a temperature of at least 42 degrees Celsius for at least 6 hours.

1001. One or more of the methods of Examples 805-1000, wherein the blood is pumped in the fluid flow path at a rate of at least 4 liters per minute for a duration of at least 30 minutes.

1002. One or more of the methods of Examples 805-1000, wherein the blood is pumped in the fluid flow path at a rate of at least 4 liters per minute for a duration of at least 2 hours.

1003. One or more of the methods of Examples 805-1000, wherein the blood is pumped in the fluid flow path at a rate of at least 4 liters per minute for a duration of at least 3 hours.

1004. One or more of the methods of Examples 805-1000, wherein the blood is pumped in the fluid flow path at a rate of at least 4 liters per minute for a duration of at least 4 hours.

The following is another numbered list of examples identifying particular combinations of the techniques disclosed above. The present disclosure is not limited to the following combinations as the following combinations are only examples. The techniques and options discussed above can be combined in any suitable manner.

Further Examples

1. A system comprising:
   one or more pumps configured to draw blood from a patient into a fluid flow path at a rate above 4 liters per minute; and
   one or more heat exchangers coupled to the fluid flow path and configured to heat the blood to a temperature above 42 degrees Celsius and below 43.8 degrees Celsius, wherein the one or more heat exchangers use a liquid or gas fluid pumped at a rate of at least 1 gallon per minute. Any of the temperature ranges described in the present disclosure could be used. Any of the flow rates described in the present disclosure could be used.

2. The system of Example 1, wherein the one or more pumps are configured to draw blood from the patient into the fluid flow path at a rate equal to or above 5 liters per minute and equal to or below 7 liters per minute. The rate could be an instantaneous rate or an average rate. The rate could be sustained for a continuous or intermittent time period of any of the lengths described in the present disclosure.

3. The system of Example 1, further comprising one or more convection dialysis modules configured to perform convection dialysis on at least a portion of the blood.

4. The system of Example 1, wherein the one or more heat exchangers are configured to heat the blood to a temperature above 42 degrees Celsius and below 43.8 degrees Celsius for a period between 2 and 6 hours. Any of the temperature ranges described in the present disclosure could be used.

5. The system of Example 1, further comprising one or more support system modules configured to allow anesthesia to be administered to the patient such that the ability of the patient's brain to control the temperature of the body is substantially impaired.

6. The system of Example 1, further comprising one or more reintroduction system modules configured to allow one or more chemicals or nutrients to be added to at least a portion of the blood. Any of the rates described in the present disclosure regarding introducing chemicals or nutrients could be used.

7. The system of Example 1, further comprising one or more oxygenators configured to add oxygen to at least a portion of the blood. Any of the rates described in the present disclosure regarding introducing chemicals or nutrients could be used.

8. The system of Example 1, further comprising, one or more venting devices configured to remove carbon dioxide from at least a portion of the blood.

9. The system of Example 1, wherein the one or more heat exchangers are configured to heat the blood to a temperature above 42 degrees Celsius and below 43.8 degrees Celsius for a period greater than 1 hour.

10. A system comprising:
    one or more pumps configured to draw blood from a patient into a fluid flow path at a rate above 4 liters per minute;
    one or more heat exchangers coupled to the fluid flow path and configured to heat the blood to a temperature above 42 degrees Celsius and below 43.8 degrees Celsius; and
    one or more venting modules configured to remove carbon dioxide from at least a portion of the blood by causing the blood to flow through a membrane while passing a gas over the membrane. Any of the temperature ranges described in the present disclosure could be used. Any of the flow rates described in the present disclosure could be used.

11. The system of Example 10, wherein the heat exchanger is configured to circulate a heated fluid at a rate above 1 gallon per minute.

12. The system of Example 10, wherein the one or more venting modules are configured to add oxygen to at least a portion of the blood at a first rate at a first time and at a second rate at a second time. Any of the rates of adding oxygen to at least a portion of the blood described in the present disclosure could be used.

13. A method comprising:
    pumping blood in a fluid flow path at a rate above 4 liters per minute; and
    heating the blood to a temperature above 42 degrees Celsius and below 43.8 degrees Celsius using a heated fluid. Any of the temperature ranges described in the present disclosure could be used. Any of the flow rates associated with the blood described in the present disclosure could be used. Any of the flow rates associated with the heated fluid described in the present disclosure could be used.

14. The method of Example 13, further comprising drawing the blood from the patient into the fluid flow path at a rate equal to or above 5 liters per minute and equal to or below 7 liters per minute. The rate could be an instantaneous rate or an average rate. The rate could be sustained for a continuous or intermittent time period of any of the lengths described in the present disclosure.

15. The method of Example 13, further comprising administering anesthesia to the patient such that the ability of the patient's brain to control the temperature of the body is substantially impaired.

16. The method of Example 13, further comprising adding oxygen to at least a portion of the blood. Any of the rates of adding oxygen to the blood described in the present disclosure could be used.

17. The method of Example 16, wherein:
    adding oxygen to at least a portion of the blood comprises adding oxygen to at least a portion of the blood at a first rate at a first time and at a second rate at a second time;
    the second time occurs after the first time; and
    the second time beginning at least thirty minutes after heating the blood.

18. A method of treating blood outside of a body of a patient, comprising:
    circulating blood through a fluid flow path at a rate above 4 liters per minute for at least one hour;
    heating the blood to a temperature above 42 degrees Celsius and below 43.8 degrees Celsius; and
    adding chemicals or nutrients to the blood at a rate of at least 7 liters per hour. Any of the temperature ranges described in the present disclosure could be used. Any of the blood flow rates described in the present disclosure could be used.

19. The method of Example 18, further comprising drawing the blood from the patient into the fluid flow path at a rate equal to or above 5 liters per minute and equal to or below 7 liters per minute. The rate could be an instantaneous rate or an average rate. The rate could be sustained for a continuous or intermittent time period of any of the lengths described in the present disclosure.

20. A method of treating blood outside of a body of a patient, comprising:
    heating blood in a fluid flow path to a temperature above 42 degrees Celsius and below 43.8 degrees Celsius using a heated fluid pumped at a rate of at least one gallon per minute; and performing convection dialysis on at least a portion of the blood. Any of the temperature ranges described in the present disclosure could be used.

21. The method of Example 21, further comprising:
ceasing to heat the blood in the fluid flow path; and
after ceasing to heat the blood, continuing to perform convection dialysis on at least a portion of the blood.

22. A method of treating blood outside of a body of a patient, comprising:
heating blood in a fluid flow path to a temperature above 42 degrees Celsius and below 43.8 degrees Celsius;
removing carbon dioxide from at least a portion of the blood using one or more venting modules; and
adding oxygen to at least a portion of the blood at a first rate during a first time period and at a second rate during a second time period. Any of the temperature ranges described in the present disclosure could be used.

23. A method of treating blood outside of a body of a patient, comprising:
heating blood in a fluid flow path to a temperature above 42 degrees Celsius and below 43.8 degrees Celsius; and
adding oxygen to at least a portion of the blood using one or more oxygenators at a first rate during a first time period and at a second rate during a second time period. Any of the temperature ranges described in the present disclosure could be used.

24. A system for treating blood outside of a body of a patient, comprising:
a fluid flow path located outside of a body of a patient;
one or more pumps configured to circulate the blood in the fluid flow path at a rate above 4 liters per minute; and
one or more heat exchangers coupled to the fluid flow path and configured to heat the blood to a temperature above 42 degrees Celsius and below 43.8 degrees Celsius using a heated fluid pumped at a rate of at least one gallon per minute. Any of the temperature ranges described in the present disclosure could be used. Any of the flow rates described in the present disclosure could be used.

25. The system of Example 24, wherein the one or more pumps are configured to circulate the blood in the fluid flow path at a rate equal to or above 5 liters per minute and equal to or below 7 liters per minute. The rate could be an instantaneous rate or an average rate. The rate could be sustained for a continuous or intermittent time period of any of the lengths described in the present disclosure.

26. A method of treating blood outside of a body of a patient, comprising:
heating blood in a fluid flow path to a temperature above 42 degrees Celsius and below 43.8 degrees Celsius using a heated fluid pumped at a rate of at least one gallon per minute;
performing convection dialysis on at least a portion of the blood; and
administering medication configured to treat edema. Any of the temperature ranges described in the present disclosure could be used.

27. A system comprising:
one or more pumps configured to draw blood from a patient into a fluid flow path at a rate above 4 liters per minute;
one or more heat exchangers coupled to the fluid flow path and configured to heat the blood to a temperature above 42 degrees Celsius and below 43.8 degrees Celsius, at least one of the one or more heat exchangers comprising channels formed from a block of solid material; and
one or more venting modules configured to remove carbon dioxide from at least a portion of the blood by causing the blood to flow through a membrane while passing a gas over the membrane. Any of the temperature ranges described in the present disclosure could be used. Any of the flow rates described in the present disclosure could be used.

28. A system comprising:
one or more pumps configured to draw blood from a patient into a fluid flow path at a rate above 4 liters per minute;
at least two heat exchangers arranged in parallel coupled to the fluid flow path and configured to heat the blood to a temperature above 42 degrees Celsius and below 43.8 degrees Celsius; and
one or more venting modules configured to remove carbon dioxide from at least a portion of the blood by causing the blood to flow through a membrane while passing a gas over the membrane. Any of the temperature ranges described in the present disclosure could be used. Any of the flow rates described in the present disclosure could be used.

29. A system comprising:
one or more pumps configured to draw blood from a patient into a fluid flow path at a rate above 4 liters per minute;
at least two heat exchangers arranged in series coupled to the fluid flow path and configured to heat the blood to a temperature above 42 degrees Celsius and below 43.8 degrees Celsius; and
one or more venting modules configured to remove carbon dioxide from at least a portion of the blood by causing the blood to flow through a membrane while passing a gas over the membrane. Any of the temperature ranges described in the present disclosure could be used. Any of the flow rates described in the present disclosure could be used.

30. A system comprising:
one or more pumps configured to draw blood from a patient into a fluid flow path at a rate above 4 liters per minute;
a heat exchanger coupled to the fluid flow path and configured to heat the blood to a temperature above 42 degrees Celsius and below 43.8 degrees Celsius, the heat exchanger comprising a membrane with an effective surface area greater than 1.8 square meters. Any of the temperature ranges described in the present disclosure could be used. Any of the flow rates described in the present disclosure could be used.

31. A method of treating blood outside of a body of a patient, comprising:
heating blood in a fluid flow path to a temperature above 42 degrees Celsius and below 43.8 degrees Celsius using a heated fluid pumped at a rate of at least one gallon per minute;
removing carbon dioxide or carbon monoxide by causing the blood to flow through a membrane while passing a gas over the membrane; and
administering a free radical or unstable substance to the blood that facilitates the production of reactive oxygen species within the blood. Any of the temperature ranges described in the present disclosure could be used. Any amount of the substance that facilitates the production of reactive oxygen species within the blood described in the present disclosure could be used.

32. The method of Example 31, wherein the free radical or unstable substance that facilitates the production of reactive oxygen species within the blood comprises ozone.

33. The method of Example 31, wherein the free radical or unstable substance that facilitates the production of reactive oxygen species within the blood comprises Freon.

34. The method of Example 31, further comprising removing carbon monoxide from the blood by causing the blood to flow through a membrane while passing a gas over the membrane.

35. The method of Example 31, wherein the free radical or unstable substance that facilitates the production of reactive oxygen species within the blood comprises iron.

36. The method of Example 31, wherein the free radical or unstable substance that facilitates the production of reactive oxygen species within the blood comprises copper.

37. The method of Example 31, wherein administering the free radical or unstable substance to the blood that facilitates the production of reactive oxygen species within the blood comprises administering a combination of substances, the combination of substances comprising ozone and iron.

38. The method of Example 31, wherein administering the free radical or unstable substance to the blood that facilitates the production of reactive oxygen species within the blood comprises administering a combination of substances, the combination of substances comprising ozone and copper.

39. A system comprising:
one or more pumps configured to draw blood from a patient into a fluid flow path at a rate above 4 liters per minute;
one or more heat exchangers coupled to the fluid flow path and configured to heat the blood to a temperature above 42 degrees Celsius and below 43.8 degrees Celsius, at least one of the one or more heat exchangers comprising channels formed from a block of solid material; and
one or more modules configured to administer a free radical or unstable substance to the blood that facilitates the production of reactive oxygen species within the blood.

Any of the temperature ranges described in the present disclosure could be used. Any amount of the substance that facilitates the production of reactive oxygen species within the blood described in the present disclosure could be used.

40. The system of Example 39, wherein the free radical or unstable substance that facilitates the production of reactive oxygen species within the blood comprises ozone.

41. The system of Example 39, wherein the free radical or unstable substance that facilitates the production of reactive oxygen species within the blood comprises Freon.

42. The system of Example 39, further comprising one or more venting modules configured to remove carbon monoxide from the blood by causing the blood to flow through a membrane while passing a gas over the membrane.

43. The system of Example 39, wherein the free radical or unstable substance that facilitates the production of reactive oxygen species within the blood comprises iron.

44. The system of Example 39, wherein the free radical or unstable substance that facilitates the production of reactive oxygen species within the blood comprises copper.

45. The system of Example 39, wherein the one or more modules configured to administer the free radical or unstable substance to the blood that facilitates the production of reactive oxygen species within the blood comprises the one or more modules configured to administer a combination of substances, the combination of substances comprising ozone and iron.

46. The system of Example 39, wherein the one or more modules configured to administer the free radical or unstable substance to the blood that facilitates the production of reactive oxygen species within the blood comprises the one or more modules configured to administer a combination of substances, the combination of substances comprising ozone and copper.

47. A system comprising:
one or more pumps configured to draw blood from a patient into a fluid flow path at a rate above 4 liters per minute;
at least two heat exchangers arranged in parallel coupled to the fluid flow path and configured to heat the blood to a temperature above 42 degrees Celsius and below 43.8 degrees Celsius; and
one or more modules configured to administer a free radical or unstable substance to the blood that facilitates the production of reactive oxygen species within the blood.

Any of the temperature ranges described in the present disclosure could be used. Any amount of the substance that facilitates the production of reactive oxygen species within the blood described in the present disclosure could be used.

48. The system of Example 47, wherein the free radical or unstable substance that facilitates the production of reactive oxygen species within the blood comprises ozone.

49. The system of Example 47, wherein the free radical or unstable substance that facilitates the production of reactive oxygen species within the blood comprises Freon.

50. The system of Example 47, further comprising one or more venting modules configured to remove carbon monoxide from the blood by causing the blood to flow through a membrane while passing a gas over the membrane.

51. The system of Example 47, wherein the free radical or unstable substance that facilitates the production of reactive oxygen species within the blood comprises iron.

52. The system of Example 47, wherein the free radical or unstable substance that facilitates the production of reactive oxygen species within the blood comprises copper.

53. The system of Example 47, wherein the one or more modules configured to administer the free radical or unstable substance to the blood that facilitates the production of reactive oxygen species within the blood comprises the one or more modules configured to administer a combination of substances, the combination of substances comprising ozone and iron.

54. The system of Example 47, wherein the one or more modules configured to administer the free radical or unstable substance to the blood that facilitates the production of reactive oxygen species within the blood comprises the one or more modules configured to administer a combination of substances, the combination of substances comprising ozone and copper.

55. A system comprising:
one or more pumps configured to draw blood from a patient into a fluid flow path at a rate above 4 liters per minute;
at least two heat exchangers arranged in series coupled to the fluid flow path and configured to heat the blood to a temperature above 42 degrees Celsius and below 43.8 degrees Celsius; and
one or more modules configured to administer a free radical or unstable substance to the blood that facilitates the production of reactive oxygen species within the blood.

Any of the temperature ranges described in the present disclosure could be used. Any amount of the substance that facilitates the production of reactive oxygen species within the blood described in the present disclosure could be used.

56. The system of Example 55, wherein the free radical or unstable substance that facilitates the production of reactive oxygen species within the blood comprises ozone.

57. The system of Example 55, wherein the free radical or unstable substance that facilitates the production of reactive oxygen species within the blood comprises Freon.

58. The system of Example 55, further comprising one or more venting modules configured to remove carbon monoxide from the blood by causing the blood to flow through a membrane while passing a gas over the membrane.

59. The system of Example 55, wherein the free radical or unstable substance that facilitates the production of reactive oxygen species within the blood comprises iron.

60. The system of Example 55, wherein the free radical or unstable substance that facilitates the production of reactive oxygen species within the blood comprises copper.

61. The system of Example 55, wherein the one or more modules configured to administer the free radical or unstable substance to the blood that facilitates the production of reactive oxygen species within the blood comprises the one or more modules configured to administer a combination of substances, the combination of substances comprising ozone and iron.

62. The system of Example 55, wherein the one or more modules configured to administer the free radical or unstable substance to the blood that facilitates the production of reactive oxygen species within the blood comprises the one or more modules configured to administer a combination of substances, the combination of substances comprising ozone and copper.

63. A system comprising:
one or more pumps configured to draw blood from a patient into a fluid flow path at a rate above 4 liters per minute;
a heat exchanger coupled to the fluid flow path and configured to heat the blood to a temperature above 42 degrees Celsius and below 43.8 degrees Celsius, the heat exchanger comprising having an effective surface area greater than or equal to six square inches.
Any of the temperature ranges described in the present disclosure could be used. Any of the flow rates described in the present disclosure could be used.

64. Apparatus for treating blood outside of a body of a patient, comprising:
one or more heat exchangers configured to be coupled to a fluid flow path located outside of a body of a patient and configured to heat blood in the fluid flow path circulating at a rate above 4 liters per minute to a temperature above 42 degrees Celsius and below 43.8 degrees Celsius using a heated fluid pumped at a rate of at least one gallon per minute.

65. Apparatus for treating blood outside of a body of a patient, comprising:
one or more modules configured to administer a free radical or unstable substance to blood circulating in a fluid flow path located outside the body of a patient, the blood circulating in at least part of the fluid flow path at a rate above 4 liters per minute and at a temperature above 42 degrees Celsius and below 43.8 degrees Celsius, the free radical or unstable substance facilitating the production of reactive oxygen species within the blood.

66. Apparatus for treating blood outside of a body of a patient, comprising:
one or more venting modules configured to remove carbon dioxide from blood circulating in a fluid flow path located outside the body of a patient by causing the blood to flow through a membrane while passing a gas over the membrane, the blood circulating in at least part of the fluid flow path at a rate above 4 liters per minute and at a temperature above 42 degrees Celsius and below 43.8 degrees Celsius.

67. The system of Example 47, wherein the free radical or unstable substance that facilitates the production of reactive oxygen species within the blood comprises a chemotherapeutic agent.

68. A system comprising:
one or more pumps configured to draw blood from a patient into a fluid flow path at a rate above 4 liters per minute; and
one or more dialysis modules coupled to the fluid flow path and configured to treat at least a portion of the blood at a rate of at least 0.5 liters per minute.

69. The system of Example 68, where in the one more dialysis modules are configured to perform convection dialysis.

70. The system of Example 68, where in the one more dialysis modules are configured to perform diffusion dialysis.

71. The system of Example 68, wherein:
the one or more pumps comprise a first side, the first side configured to draw blood from the patient;
the one or more pumps comprise a second side, the second side configured to cause blood to return to the patent;
the one or more dialysis modules are configured to receive the portion of the blood from the second side of the pump; and
the one or more dialysis modules are configured to cause treated blood to enter the first side of the one or more pumps.

72. The system of Example 68, wherein the one or more dialysis modules are configured to treat the portion of the blood at a rate of at least 0.9 liters per minute.

73. The system of Example 68, further comprising one or more reintroduction modules configured to add chemicals or nutrients to the blood at a rate of at least 6.5 liters per hour.

74. A system comprising:
one or more pumps configured to draw blood from a patient into a fluid flow path at a rate above 4 liters per minute;
one or more venting modules configured to remove carbon dioxide from at least a portion of the blood by causing the blood to flow through a membrane while passing a gas over the membrane. Any of the flow rates of the venting modules described in the present disclosure could be used.

75. The system of Example 74, wherein the one or more venting modules are further configured to add oxygen to at least a portion of the blood.

The following is another numbered list of examples identifying particular combinations of the techniques disclosed above. The present disclosure is not limited to the following combinations as the following combinations are only examples. The techniques and options discussed above can be combined in any suitable manner.

Further Examples

1. A system comprising:
   one or more pumps configured to pump blood in a fluid flow path at a collective rate of at least 4 liters per minute; and
   one or more dialysis modules coupled to the fluid flow path and configured to perform dialysis on at least a portion of the blood at a collective rate of at least 0.5 liters per minute.
2. The system of Example 1, wherein the one or more dialysis modules are configured to perform convection dialysis.
3. The system of Example 1, wherein the one or more dialysis modules are configured to perform diffusion dialysis.
4. The system of Example 1, wherein the one or more pumps are configured to pump the blood at a collective rate of at least 5 liters per minute.
5. The system of Example 1, wherein the one or more pumps are configured to pump the blood at a collective rate between 4 and 7 liters per minute.
6. The system of Example 1, wherein the one or more dialysis modules are configured to perform the dialysis on at least a portion of the blood at a collective rate of at least 0.6 liters per minute.
7. The system of Example 1, wherein the one or more dialysis modules are configured to perform the dialysis on at least a portion of the blood at a collective rate of at least 1 liter per minute.
8. The system of Example 1, wherein the one or more dialysis modules are configured to perform the dialysis on at least a portion of the blood at a collective rate of at least 1.5 liters per minute.
9. The system of Example 1, wherein the one or more dialysis modules are configured to perform the dialysis on at least a portion of the blood at a collective rate of between 0.6 to 1.5 liters per minute.
10. The system of Example 1, further comprising one or more heat exchangers coupled to the fluid flow path and configured to heat the blood to a temperature of at least 42 degrees Celsius.
11. The system of Example 10, further comprising one or more venting modules coupled to the fluid flow path, the one or more venting modules configured to remove carbon dioxide from at least a portion of the blood.
12. The system of Example 1, further comprising a reintroduction module configured to add electrolyte-balanced fluid to at least a portion of the blood at a rate above 7 liters per hour.
13. The system of Example 1, further comprising a reintroduction module coupled to the fluid flow path and configured to add a substance to at least a portion of the blood, the substance facilitating the production of reactive oxygen species within the blood.
14. The system of Example 1, wherein:
   the one or more dialysis modules are configured to perform convection dialysis at a collective rate of between 0.75 and 1.5 liters per minute;
   the one or more pumps configured to pump the blood in the fluid flow path at a collective rate of between 4 and 7 liters per minute.
15. The system of Example 14, further comprising:
   one or more heat exchangers configured to heat the blood to a temperature of at least 42 degrees Celsius; and
   one or more venting modules coupled to the fluid flow path, the one or more venting modules configured to remove carbon dioxide from at least a portion of the blood.
16. The system of Example 15, further comprising a reintroduction module configured to add a substance to at least a portion of the blood, the substance facilitating the production of reactive oxygen species within the blood.
17. A method comprising:
   pumping blood in a fluid flow path at a rate of at least 4 liters per minute; and
   performing dialysis on at least a portion of the blood at a rate of at least 0.5 liters per minute.
18. The method of Example 17, wherein performing dialysis comprises performing convection dialysis.
19. The method of Example 17, wherein performing dialysis comprises performing diffusion dialysis.
20. The method of Example 17, wherein the blood is pumped at a rate of at least 5 liters per minute.
21. The method of Example 17, wherein the blood is pumped at a rate between 4 and 7 liters per minute.
22. The method of Example 17, wherein the dialysis is performed on at least the portion of the blood at a rate of at least 0.6 liters per minute.
23. The method of Example 17, wherein the dialysis is performed on at least the portion of the blood at a rate of at least 1 liter per minute.
24. The method of Example 17, wherein the dialysis is performed on at least the portion of the blood at a rate of at least 1.5 liters per minute.
25. The method of Example 17, wherein the dialysis is performed on at least the portion of the blood at a rate of between 0.6 to 1.5 liters per minute.
26. The method of Example 17, further comprising heating the blood in the fluid flow path to a temperature of at least 42 degrees Celsius.
27. The system of Example 26, further comprising removing carbon dioxide from at least a portion of the blood.
28. The method of Example 17, further comprising adding electrolyte-balanced fluid to at least a portion of the blood at a rate above 7 liters per hour.
29. The method of Example 17, further comprising adding a substance to at least a portion of the blood, the substance facilitating the production of reactive oxygen species within the blood.
30. The method of Example 17, wherein:
   the dialysis is performed on at least the portion of the blood by performing convection dialysis at a collective rate of between 0.75 and 1.5 liters per minute;
   the blood is pumped in the fluid flow path at a collective rate of between 4 and 7 liters per minute.
31. The method of Example 30, further comprising:
   heating at least a portion of the blood to a temperature of at least 42 degrees Celsius; and
   removing carbon dioxide from at least a portion of the blood.
32. The method of Example 31, further comprising adding a substance to at least a portion of the blood, the substance facilitating the production of reactive oxygen species within the blood.
33. The method of Example 17, wherein the blood is pumped in the fluid flow path at the rate of at least 4 liters per minute for at least 30 minutes.
34. The method of Example 17, wherein the dialysis is performed on at least a portion of the blood at the rate of at least 4 liters per minute for between 30 minutes and 48 hours.

35. The method of Example 26, wherein the blood is heated to a temperature of at least 42 degrees Celsius for at least 30 minutes.

36. The method of Example 27, wherein carbon dioxide is removed from at least a portion of the blood for at least 30 minutes.

37. The method of Example 28, wherein the electrolyte-balanced fluid is added to at least a portion of the blood at a rate above 7 liters per hour for at least 30 minutes.

38. The method of Example 33, wherein the blood is pumped in the fluid flow path at the rate of at least 4 liters per minute substantially continuously for at least 30 minutes.

39. The method of Example 34, wherein the dialysis is performed on at least a portion of the blood at the rate of at least 4 liters per minute substantially continuously for between 30 minutes and 48 hours.

40. The method of Example 35, wherein at least a portion of the blood is heated to a temperature of at least 42 degrees Celsius substantially continuously for at least 30 minutes.

41. The method of Example 36, wherein carbon dioxide is removed from at least a portion of the blood substantially continuously for at least 30 minutes.

42. The method of Example 37, wherein the electrolyte-balanced fluid is added to at least a portion of the blood at a rate above 7 liters per hour substantially continuously for at least 30 minutes.

43. A method for treating cancer comprising:
pumping blood from a human body into a fluid flow path at a collective rate of at least 4 liters per minute;
performing dialysis on at least a portion of the blood at a collective rate of at least 0.5 liters per minute; and
returning the blood in the fluid flow path to the human body after performing dialysis on at least a portion of the blood.

44. The method of Example 43, wherein performing dialysis comprises performing convection dialysis.

45. The method of Example 43, further comprising heating the human body to a temperature of at least 42 degrees Celsius.

46. The method of Example 45, further comprising removing carbon dioxide from at least a portion of the blood.

47. The method of Example 43, further comprising adding electrolyte-balanced fluid to the human body at a rate above 7 liters per hour.

48. The method of Example 43, further comprising causing an increase in the production of reactive oxygen species within the human body.

49. The method of Example 43, wherein:
the dialysis is performed on at least the portion of the blood by performing convection dialysis at a collective rate of between 0.75 and 1.5 liters per minute;
the blood is pumped in the fluid flow path at a collective rate of between 4 and 7 liters per minute.

50. The method of Example 49, further comprising:
heating the human body to a temperature of at least 42 degrees Celsius; and
removing carbon dioxide from at least a portion of the blood.

51. The method of Example 50, further comprising causing an increase in reactive oxygen species in the human body by adding a substance to at least a portion of the blood outside the human body.

52. The method of Example 43, wherein the blood is pumped in the fluid flow path at the rate of at least 4 liters per minute for at least 30 minutes.

53. The method of Example 43, wherein the dialysis is performed on at least a portion of the blood at the rate of at least 0.75 liters per minute for between 30 minutes and 48 hours.

54. The method of Example 45, wherein the human body is heated to a temperature of at least 42 degrees Celsius for at least 30 minutes.

55. The method of Example 46, wherein carbon dioxide is removed from at least a portion of the blood for at least 30 minutes.

56. The method of Example 47, wherein the electrolyte-balanced fluid is added to the human body at a rate above 7 liters per hour for at least 30 minutes.

57. The method of Example 52, wherein the blood is pumped in the fluid flow path at the rate of at least 4 liters per minute substantially continuously for at least 30 minutes.

58. The method of Example 53, wherein the dialysis is performed on at least a portion of the blood at the rate of at least 0.75 liters per minute substantially continuously for between 30 minutes and 48 hours.

59. The method of Example 54, wherein the human body is heated to a temperature of at least 42 degrees Celsius substantially continuously for at least 30 minutes.

60. The method of Example 55, wherein carbon dioxide is removed from at least a portion of the blood substantially continuously for at least 30 minutes.

61. The method of Example 56, wherein the electrolyte-balanced fluid is added to the human body at a rate above 7 liters per hour substantially continuously for at least 30 minutes.

62. The methods of Examples 46 and 50, further comprising adding a chemotherapeutic agent to the human body.

63. The method of Example 51, wherein the substance comprises at least one of: iron, copper, Freon, and ozone.

64. The method of Example 43, further comprising:
heating the human body to a temperature of at least 42 degrees Celsius for at least 30 minutes;
adding electrolyte-balanced fluid at a rate above 7 liters per hour for at least 30 minutes;
causing the production of reactive oxygen species within the human body by adding a substance to at least a portion of the blood outside of the human body, the substance comprising at least one of: iron, copper, Freon, and ozone; and
wherein the dialysis is performed on at least a portion of the blood at the rate of at least 0.75 liters per minute by performing convection dialysis for between 30 minutes and 48 hours.

65. The method of Example 43, further comprising:
heating the human body to a temperature of at least 42 degrees Celsius for at least 30 minutes;
adding electrolyte-balanced fluid at a rate above 7 liters per hour for at least 30 minutes;
adding a chemotherapeutic agent to the human body; and
wherein the dialysis is performed on at least a portion of the blood at the rate of at least 0.75 liters per minute by performing convection dialysis for between 30 minutes and 48 hours.

66. A system comprising:
one or more pumps configured to pump blood in a fluid flow path at a collective rate of at least 4 liters per minute; and
one or more heat exchangers coupled to the fluid flow path and configured to heat the blood to a temperature of at least 42 degrees Celsius.

67. The system of Example 66, wherein the one or more heat exchangers are configured to heat the blood to a temperature between 42 and 45 degrees Celsius.

68. The system of Example 66, wherein the one or more heat exchangers are configured to heat the blood to a temperature of at least 42.5 degrees Celsius.

69. The system of Example 66, wherein the one or more pumps are configured to pump the blood at a collective rate of at least 5 liters per minute.

70. The system of Example 66, wherein the one or more pumps are configured to pump the blood at a collective rate between 4 and 7 liters per minute.

71. The system of Example 66, further comprising a reintroduction module coupled to the fluid flow path and configured to add a substance to at least a portion of the blood, the substance facilitating the production of reactive oxygen species within the blood.

72. The system of Example 71, wherein the substance comprises at least one of: iron, copper, and ozone.

73. The system of Example 66, further comprising a reintroduction module coupled to the fluid flow path and configured to add a chemotherapeutic substance to at least a portion of the blood.

74. The system of Example 66, further comprising one or more venting modules coupled to the fluid flow path and configured to:
   remove carbon dioxide from at least a portion of the blood; and
   add oxygen to at least a portion of the blood.

75. The system of Example 66, further comprising one or more convection dialysis modules coupled to the fluid flow path and configured to perform dialysis on at least a portion of the blood at a collective rate of at least 0.5 liters per minute.

76. The system of Example 75, further comprising a reintroduction module coupled to the fluid flow path and configured to add electrolyte-balanced fluid to at least a portion of the blood at a rate above 7 liters per hour.

77. A method comprising:
   pumping blood in a fluid flow path at a rate of at least 4 liters per minute; and
   heating at least a portion of the blood to a temperature of at least 42 degrees Celsius.

78. The method of Example 77, wherein at least a portion of the blood is heated to a temperature between 42 and 45 degrees Celsius.

79. The method of Example 77, wherein at least a portion of the blood is heated to a temperature of at least 42.5 degrees Celsius.

80. The method of Example 77, wherein the blood is pumped at a rate of at least 5 liters per minute.

81. The method of Example 77, wherein the blood is pumped at a rate between 4 and 7 liters per minute.

82. The method of Example 77, further comprising adding a substance to at least a portion of the blood in the fluid flow path, the substance facilitating the production of reactive oxygen species within the blood.

83. The method of Example 82, wherein the substance comprises at least one of: iron, copper, and ozone.

84. The method of Example 77, further comprising adding a chemotherapeutic substance to at least a portion of the blood.

85. The method of Example 77, further comprising removing carbon dioxide from at least a portion of the blood.

86. The method of Example 77, further comprising performing dialysis on at least a portion of the blood at a rate of at least 0.5 liters per minute.

87. The method of Example 86, further comprising adding electrolyte-balanced fluid to at least a portion of the blood at a rate above 7 liters per hour.

88. The method of Example 77, wherein the blood is pumped in the fluid flow path at the rate of at least 4 liters per minute for at least 30 minutes.

89. The method of Example 86, wherein the dialysis is performed on at least a portion of the blood at the rate of at least 4 liters per minute for between 30 minutes and 48 hours.

90. The method of Example 77, wherein the blood is heated to a temperature of at least 42 degrees Celsius for at least 30 minutes.

91. The method of Example 85, wherein carbon dioxide is removed from at least a portion of the blood for at least 30 minutes.

92. The method of Example 87, wherein the electrolyte-balanced fluid is added to at least a portion of the blood at a rate above 7 liters per hour for at least 30 minutes.

93. The method of Example 88, wherein the blood is pumped in the fluid flow path at the rate of at least 4 liters per minute substantially continuously for at least 30 minutes.

94. The method of Example 89, wherein dialysis is performed on at least a portion of the blood at the rate of at least 4 liters per minute substantially continuously for between 30 minutes and 48 hours.

95. The method of Example 90, wherein the blood is heated to a temperature of at least 42 degrees Celsius substantially continuously for at least 30 minutes.

96. The method of Example 91, wherein carbon dioxide is removed from at least a portion of the blood substantially continuously for at least 30 minutes.

97. The method of Example 92, wherein the electrolyte-balanced fluid is added to at least a portion of the blood in the fluid flow path at a rate above 7 liters per hour substantially continuously for at least 30 minutes.

98. A method for treating cancer comprising:
   removing blood from a human body into a fluid flow path at a rate of at least 4 liters per minute;
   heating the blood outside of the human body;
   returning the blood to the human body after heating the blood outside of the human body; and
   wherein the human body is heated to a temperature of at least 42 degrees Celsius for at least 30 minutes.

99. The method of Example 98, further comprising causing the production of reactive oxygen species within the human body by adding a substance to at least a portion of the blood outside the human body.

100. The method of Example 99, wherein the substance comprises at least one of: iron, copper, Freon, and ozone.

101. The method of Example 98, further comprising adding a chemotherapeutic substance to the human body.

102. The method of Example 98, further comprising removing carbon dioxide from at least a portion of the blood outside of the human body.

103. The method of Example 98, further comprising performing dialysis on at least a portion of the blood at a rate of at least 0.5 liters per minute.

104. The method of Example 103, further comprising adding electrolyte-balanced fluid to the human body at a rate above 7 liters per hour.

105. The method of Example 98, further comprising pumping the blood in the fluid flow path at a rate of at least 4 liters per minute for at least 30 minutes.

106. The method of Example 103, wherein the dialysis is performed on at least a portion of the blood at the rate of at least 4 liters per minute for between 30 minutes and 48 hours.

107. The method of Example 102, wherein carbon dioxide is removed from at least a portion of the blood for at least 30 minutes.

108. The method of Example 104, wherein the electrolyte-balanced fluid is added to the human body at a rate above 7 liters per hour for at least 30 minutes.

109. The method of Example 105, wherein the blood is pumped in the fluid flow path at the rate of at least 4 liters per minute substantially continuously for at least 30 minutes.

110. The method of Example 106, wherein the dialysis is performed on at least a portion of the blood at the rate of at least 4 liters per minute substantially continuously for between 30 minutes and 48 hours.

111. The method of Example 98, wherein the human body is heated to the temperature of at least 42 degrees Celsius substantially continuously for at least 30 minutes.

112. The method of Example 107, wherein carbon dioxide is removed from at least a portion of the blood substantially continuously for at least 30 minutes.

113. The method of Example 108, wherein the electrolyte-balanced fluid is added to the human body at a rate above 7 liters per hour substantially continuously for at least 30 minutes.

114. The method of Example 98, further comprising:
adding electrolyte-balanced fluid at a rate above 7 liters per hour for at least 30 minutes;
causing the production of reactive oxygen species within the human body by adding a substance to at least a portion of the blood outside of the human body, the substance comprising at least one of: iron, copper, Freon, and ozone; and
wherein the blood is heated outside of the body to a temperature of at least 42 degrees Celsius.

115. The method of Example 98, further comprising:
adding electrolyte-balanced fluid at a rate above 7 liters per hour for at least 30 minutes;
adding a chemotherapeutic agent to the human body; and
wherein the blood is heated outside of the body to a temperature of at least 42 degrees Celsius.

116. A system comprising:
one or more heat exchangers configured to heat blood in a fluid flow path to a temperature of at least 42 degrees Celsius; and
one or more venting modules coupled to the fluid flow path, the one or more venting modules configured to remove carbon dioxide from at least a portion of the blood.

117. The system of Example 116, wherein the one or more venting modules are configured to add oxygen to at least a portion of the blood.

118. The system of Example 116, further comprising an oxygenator coupled to the fluid flow path and configured to add oxygen to at least a portion of the blood.

119. The system of Example 116, wherein the one or more venting modules are configured to cause at least a portion of the blood to flow through at least one membrane.

120. The system of Example 119, wherein the at least one membrane collectively has an effective surface area greater than 1.8 square meters.

121. The system of Example 116, further comprising a reintroduction module coupled to the fluid flow path and configured to add a substance to at least a portion of the blood, the substance facilitating the production of reactive oxygen species within the blood.

122. The system of Example 116, wherein the one or more heat exchangers are configured to heat the blood to a temperature between 42 and 45 degrees Celsius.

123. The system of Example 116, wherein the one or more heat exchangers are configured to heat the blood to a temperature of at least 42.5 degrees Celsius.

124. The system of Example 116, wherein the one or more heat exchangers are configured to heat the blood to a temperature of at least 43 degrees Celsius.

125. The system of Example 116, further comprising one or more dialysis modules coupled to the fluid flow path and configured to perform dialysis on at least a portion of the blood at a collective rate of at least 0.5 liters per minute.

126. The system of Example 116, further comprising one or more pumps configured to pump the blood in the fluid flow path at a collective rate of at least 4 liters per minute.

127. The system of Example 116, further comprising a heated enclosure enclosing the one or more heat exchangers and the one or more venting modules, the area inside the heated enclosure being at a temperature of at least 43 degrees Celsius.

128. A method comprising:
heating blood in a fluid flow path to a temperature of at least 42 degrees Celsius; and
removing carbon dioxide from at least a portion of the blood.

129. The method of Example 128, further comprising adding oxygen to at least a portion of the blood.

130. The method of Example 128, wherein carbon dioxide is removed from the blood by causing at least a portion of the blood to flow through at least one membrane.

131. The method of Example 130, wherein the at least one membrane collectively has an effective surface area greater than 1.8 square meters.

132. The method of Example 128, further comprising adding a substance to at least a portion of the blood, the substance facilitating the production of reactive oxygen species within the blood.

133. The method of Example 128, wherein the blood is heated to a temperature between 42 and 45 degrees Celsius.

134. The method of Example 128, wherein the blood is heated to a temperature of at least 42.5 degrees Celsius.

135. The method of Example 128, wherein the blood is heated to a temperature of at least 43 degrees Celsius.

136. The method of Example 128, further comprising performing dialysis on at least a portion of the blood at a rate of at least 0.5 liters per minute.

137. The method of Example 128, further comprising pumping the blood in the fluid flow path at a rate of at least 4 liters per minute.

138. The method of Example 137, wherein the blood is pumped in the fluid flow path at the rate of at least 4 liters per minute for at least 30 minutes.

139. The method of Example 136, wherein the dialysis is performed on at least a portion of the blood at the rate of at least 0.5 liters per minute for between 30 minutes and 48 hours.

140. The method of Example 128, wherein the blood in the fluid flow path is heated to a temperature of at least 42 degrees Celsius for at least 30 minutes.

141. The method of Example 128, wherein carbon dioxide is removed from at least a portion of the blood for at least 30 minutes.

142. The method of Example 138, wherein the blood is pumped in the fluid flow path at the rate of at least 4 liters per minute substantially continuously for at least 30 minutes.

143. The method of Example 139, wherein the dialysis is performed on at least a portion of the blood at the rate of at least 0.5 liters per minute substantially continuously for between 30 minutes and 48 hours.

144. The method of Example 140, wherein the blood in the fluid flow path is heated to a temperature of at least 42 degrees Celsius substantially continuously for at least 30 minutes.

145. The method of Example 141, wherein carbon dioxide is removed from at least a portion of the blood substantially continuously for at least 30 minutes.

146. A method for treating cancer, comprising:
heating a human body to a temperature of at least 42 degrees Celsius, wherein blood of the human body is flowing outside of the human body in a fluid flow path; and
removing carbon dioxide from at least a portion of the blood.

147. The method of Example 146, further comprising adding oxygen to at least a portion of the blood.

148. The method of Example 146, wherein carbon dioxide is removed from at least a portion of the blood by causing at least a portion of the blood to flow through at least one membrane.

149. The method of Example 148, wherein the at least one membrane collectively has an effective surface area greater than 1.8 square meters.

150. The method of Example 146, further comprising causing the production of reactive oxygen species within the human body by adding a substance to at least a portion of the blood outside of the human body.

151. The method of Example 146, further comprising performing dialysis on at least a portion of the blood at a rate of at least 0.5 liters per minute.

152. The method of Example 146, further comprising pumping blood from the human body into the fluid flow path at a rate of at least 4 liters per minute.

153. The method of Example 152, wherein the blood is pumped in the fluid flow path at the rate of at least 4 liters per minute for at least 30 minutes.

154. The method of Example 151, wherein the dialysis is performed on at least a portion of the blood at the rate of at least 0.5 liters per minute for between 30 minutes and 48 hours.

155. The method of Example 146, wherein the human body is heated to a temperature of at least 42 degrees Celsius for at least 30 minutes.

156. The method of Example 146, wherein carbon dioxide is removed from at least a portion of the blood for at least 30 minutes.

157. The method of Example 153, wherein the blood is pumped in the fluid flow path at the rate of at least 4 liters per minute substantially continuously for at least 30 minutes.

158. The method of Example 154, wherein the dialysis is performed on at least a portion of the blood at the rate of at least 0.5 liters per minute substantially continuously for between 30 minutes and 48 hours.

159. The method of Example 155, wherein the human body is heated to a temperature of at least 42 degrees Celsius substantially continuously for at least 30 minutes.

160. The method of Example 156, wherein carbon dioxide is removed from at least a portion of the blood substantially continuously for at least 30 minutes.

161. The method of Example 152, further comprising adding a chemotherapeutic agent to the human body.

162. The method of Example 150, wherein the substance comprises at least one of: iron, copper, Freon, and ozone.

163. The method of Example 146, further comprising:
adding a chemotherapeutic agent to the human body;
pumping blood from the human body into the fluid flow path at a rate of at least 4 liters per minute for at least 30 minutes; and
wherein the human body is heated to a temperature of at least 42 degrees Celsius for at least 30 minutes.

164. The method of Example 146, further comprising:
causing the production of reactive oxygen species within the human body by adding a substance to at least a portion of the blood outside of the human body, the substance comprising at least one of: iron, copper, Freon, and ozone;
pumping blood from the human body into the fluid flow path at a rate of at least 4 liters per minute for at least 30 minutes; and
wherein the human body is heated to a temperature of at least 42 degrees Celsius for at least 30 minutes.

This disclosure discusses various flow rates regarding the components and steps of FIGS. 1-14. In various embodiments, any of the discussed flow rates can refer to sustained flow rates rather than mere short spikes in a flow rate (e.g., the flow is at a particular rate for less than a second or a few seconds).

In various embodiments, any of the discussed flow rates can refer to collective flow rates. The steps and components discussed above with respect to FIGS. 1-14 discuss, in certain examples, the use of more than one component or module to accomplish a function. For example, pump 104 can be implemented using multiple pumps in parallel or in series. As another example, toxin removal system 106 can be implemented using multiple modules in series or in parallel. Collective flow rates of such systems can refer to the flow rate through the path that results from such multiple components or modules working together. For example, two pumps 104 operating at 2.5 liters per minute can have a collective flow rate of 5 liters per minute."

The disclosure above discusses embodiments of performing actions for durations of time (e.g., the durations discussed above with respect to the actions performed by components of system 100 of FIG. 1). A time duration may occur continuously or substantially continuously (e.g., with temporary pauses that last a few seconds or a few minutes). The time durations disclosed herein do not need to be performed continuously in various embodiments. The time durations disclosed herein may occur continuously or in multiple periods of time that add up to the stated duration; any suitable time period can be used and different time periods can be combined such that they sum to the stated duration. For example, a disclosure that a component performs an action on blood in a path for an hour can refer to performing the action for an hour continuously, in four 15-minute periods, or in a combination of a 10-minute, 20-minute, and 30-minute periods. In some embodiments, when the time duration is not performed continuously but in multiple periods, all of the time periods may occur within, e.g., a 24 to 72 hour timeframe. Other suitable timeframes may be used, such as 4-, 5-, 6-, 7-, 8-, and 9-day timeframes. Multiple time periods may follow one another consecutively or substantially consecutively (e.g., within seconds or minutes) in various embodiments. In some embodiments, multiple time periods may not proceed consecutively.

The disclosure above discusses embodiments of performing actions on "at least a portion" of blood (e.g., flowing in a path outside of the human body). In some embodiments, such a portion can refer to all or substantially all (e.g., 80%, 85%, 90%, 95%, 97%, or 99%) of the blood.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the scope of the appended claims.

What is claimed is:

1. A system comprising:
   one or more heat exchangers configured to heat blood in a fluid flow path to a temperature between 42 and 45 degrees Celsius, wherein the blood was received from a patient with a core body temperature, as measured inside of the bladder, of between 42 and 43.2 degrees Celsius; and
   one or more venting modules coupled to the fluid flow path, the one or more venting modules configured to receive the blood heated by the one or more heat exchangers and to remove carbon dioxide from at least a portion of the heated blood by causing the heated blood to flow across one side of a filter while passing a fluid over an opposite side of the filter.

2. The system of claim 1, wherein the one or more venting modules are configured to add oxygen to at least a portion of the heated blood.

3. The system of claim 1, further comprising an oxygenator coupled to the fluid flow path and configured to add oxygen to at least a portion of the blood.

4. The system of claim 1, wherein the one or more venting modules are configured to cause at least a portion of the heated blood to flow through at least one membrane.

5. The system of claim 4, wherein the at least one membrane collectively has an effective surface area greater than 1.8 square meters.

6. The system of claim 1, further comprising a reintroduction module coupled to the fluid flow path and configured to add a substance to at least a portion of the blood, the substance facilitating the production of reactive oxygen species within the blood.

7. The system of claim 1, further comprising one or more dialysis modules coupled to the fluid flow path and configured to perform dialysis on at least a portion of the blood at a collective rate of between 0.5 and 1.8 liters per minute.

8. The system of claim 1, further comprising one or more pumps configured to pump the blood in the fluid flow path at a collective rate of between 4 and 7 liters per minute.

9. The system of claim 1, further comprising a heated enclosure enclosing the one or more heat exchangers and the one or more venting modules, the area inside the heated enclosure being at a temperature of between 42 and 45 degrees Celsius.

10. The system of claim 1, wherein the filter comprises:
    a membrane filter; or
    an absorptive filter.

11. The system of claim 1, wherein the fluid passed over the opposite side of the filter comprises:
    a gas; or
    a liquid.

12. The system of claim 1, wherein the fluid passed over the opposite side of the filter is passed in:
    a cross-flowing flow from the blood; or
    a reverse-flowing flow from the blood.

13. A system comprising:
    one or more heat exchangers configured to heat blood in a fluid flow path to a temperature between 42 and 43.9 degrees Celsius wherein the blood was received from a patient with a core body temperature of between 42 and 43.2 degrees Celsius; and
    one or more venting modules coupled to the fluid flow path, the one or more venting modules configured to receive the blood heated by the one or more heat exchangers and to remove carbon dioxide from at least a portion of the heated blood.

14. The system of claim 13, further comprising an oxygenator coupled to the fluid flow path and configured to add oxygen to at least a portion of the blood.

15. The system of claim 13, wherein removing carbon dioxide from at least a portion of the heated blood comprises causing the heated blood to flow across one side of a filter while passing a fluid over an opposite side of the filter.

16. A system comprising:
    one or more heat exchangers configured to heat blood in a fluid flow path to a temperature in a range of 42 to 45 degrees Celsius wherein the blood was received from a patient with a core body temperature of between 42 and 43.2 degrees Celsius; and
    one or more venting modules coupled to the fluid flow path, the one or more venting modules configured to remove carbon dioxide from at least a portion of the blood, wherein the one or more venting modules are configured for the blood to flow through the one or more venting modules at a rate of 4 to 7 liters per minute.

17. The system of claim 16, wherein removing carbon dioxide from at least a portion of the blood comprises causing the blood to flow across one side of a filter while passing a fluid over an opposite side of the filter.

* * * * *